(12) United States Patent
Davidowitz et al.

(10) Patent No.: US 11,306,075 B2
(45) Date of Patent: Apr. 19, 2022

(54) BENZOFURAN, BENZOTHIOPHENE, AND INDOLE ANALOGS THAT INHIBIT THE FORMATION OF TAU OLIGOMERS AND THEIR METHOD OF USE

(71) Applicant: OLIGOMERIX INC., Bronx, NY (US)

(72) Inventors: Eliot J. Davidowitz, West Hempstead, NY (US); James G. Moe, Stamford, CT (US); Allen B. Reitz, Lansdale, PA (US); Haiyan Bian, Princeton, NJ (US); Charles Gluchowski, Danville, CA (US); James Hendrix, Hillsborough, NJ (US); Albert S. Yehaskel, Great Neck, NY (US); Mark E. McDonnell, Lansdale, PA (US); H. Marie Loughran, Perkasie, PA (US)

(73) Assignee: Oligomerix, Inc., White Plains, NY (US)

( * ) Notice: Subject to any disclaimer, the term of this patent is extended or adjusted under 35 U.S.C. 154(b) by 0 days.

(21) Appl. No.: 16/471,424

(22) PCT Filed: Dec. 18, 2017

(86) PCT No.: PCT/US2017/067032
§ 371 (c)(1),
(2) Date: Jun. 19, 2019

(87) PCT Pub. No.: WO2018/118782
PCT Pub. Date: Jun. 28, 2018

(65) Prior Publication Data
US 2021/0130335 A1    May 6, 2021

Related U.S. Application Data

(60) Provisional application No. 62/436,787, filed on Dec. 20, 2016.

(51) Int. Cl.
| | | |
|---|---|---|
| C07D 409/14 | (2006.01) | |
| C07D 307/80 | (2006.01) | |
| C07D 405/14 | (2006.01) | |

(52) U.S. Cl.
CPC ......... *C07D 409/14* (2013.01); *C07D 307/80* (2013.01); *C07D 405/14* (2013.01)

(58) Field of Classification Search
CPC .................................................. C07D 409/14
See application file for complete search history.

(56) References Cited

U.S. PATENT DOCUMENTS

| | | |
|---|---|---|
| 6,479,499 B1 | 11/2002 | Kuo et al. |
| 8,455,687 B2 | 6/2013 | Snow et al. |
| 2007/0015813 A1 | 1/2007 | Carter et al. |
| 2013/0108672 A1 | 5/2013 | Shenoy |
| 2016/0038455 A1 | 2/2016 | Gill et al. |

FOREIGN PATENT DOCUMENTS

| | | |
|---|---|---|
| JP | 1973062775 A | 6/1973 |
| JP | 2012-514631 A | 6/2012 |
| RU | 2138492 C1 | 9/1999 |
| WO | 2008092231 A1 | 8/2008 |
| WO | 2014100767 A1 | 6/2014 |
| WO | 2018118791 A2 | 6/2018 |

OTHER PUBLICATIONS

Preuss, J., et al. "High-Throughput Screening for Small-Molecule Inhibitors of Plasmodium falciparum Glucose-6-Phosphate Dehydrogenase 6-Phosphogluconolactonase" Journal of Biomolecular Screening. Apr. 11, 2012. vol. 17, pp. 738-751; p. 745, Table 2.
International Search Report of the International Searching Authority (ISA/US) dated Jul. 2, 2018 of International PCT Application No. PCT/US2017/067047 filed on Dec. 18, 2017.
Written Opinion of the International Searching Authority (ISA/US) dated Jul. 2, 2018 of International PCT Application No. PCT/US2017/067047 filed on Dec. 18, 2017.
International Search Report of the International Searching Authority (ISA/US) dated Jul. 2, 2018 of International PCT Application No. PCT/US2017/067032 filed on Dec. 18, 2017.
Written Opinion of the International Searching Authority (ISA/US) dated Jul. 2, 2018 of International PCT Application No. PCT/US2017/067032 filed on Dec. 18, 2017.
Pubchem 114733145 Deposited on Jan. 29, 2016, pp. 1-9, p. 3.
Ono, et al. "Novel 18F-Labeled Benzofuran Derivatives with Improved Properties for Positron Emission Tomography (PET) Imaging of Beta-Amyloid Plaques in Alzheimer's Brains" J. Med. Chem. 2011, vol. 54, pp. 2971-2979, abstract, p. 2972, Figure 1.
Soto, et al. "Plaque busters: strategies to inhibit amyloid formation in Alzheimer's Disease" Molecular Medicine Today, 1999, vol. 5, pp. 343-350, p. 343, col. 1 para 2 to col. 2, para 1; p. 346, col. 2, para 2, Figure 3.
Pubchem 799488 Deposited on Jul. 8, 2005, pp. 1-12, p. 3.
Helen Sneddon et al.: 11 An Acid-Catalysed Conversion of 2-(4-Quinazolinylamino)benzoic Acid into 2-(2-Am inophenyl) -4(1H)-Qui nazoli none 11 , SYNLETT, vol. 2011, No. 04, Mar. 1, 2011 (Mar. 1, 2011), pp. 573-575.
Xiuling Chen et al.: 11 Meta I-free aerobic oxidative C—N bond cleavage of tertiary amines for the synthesis of N-heterocycles with high atom efficiency11 , Organic & Biomolecular Chemistry,vol. 12, No. 23, Jan. 1, 2014 (Jan. 1, 2014), p. 3802.

(Continued)

*Primary Examiner* — Golam M Shameem
(74) *Attorney, Agent, or Firm* — Sorell, Lenna & Schmidt LLP; William D. Schmidt, Esq.

(57) ABSTRACT

Novel benzofurans, benzothiophenes and indoles useful as inhibitors of tau oligomer formation, useful for the treatment of neurodegenerative diseases and related conditions are disclosed. The invention also relates to the pharmaceutically acceptable salts of said compounds, processes for the preparation of said compounds, intermediates used in the preparation of said compounds, and pharmaceutical compositions containing said compounds. The invention further relates to methods of use of said compounds, salts of said compounds, and said compositions in treating neurodegenerative diseases and related conditions.

9 Claims, No Drawings

Specification includes a Sequence Listing.

(56) References Cited

OTHER PUBLICATIONS

Ahmad F Eweas et al.: 11 Design, synthesis, anti-inflammatory, analgesic screening, and molecular docking of some novel 2-pyridyl (3)-quinazolin-4-one der i vat i ves 11 , Medicinal Chemistry Research, Birkhauser-Verlag, Boston, vol. 22, No. 2, May 27, 2012 (May 27, 2012), pp. 1011-1020, XP035165609.
Atul Kumar et al.: 11 Nanoparti cle mediated organic synthesis (NAMO-synthesis): CuI-NP catalyzed Tigand free amidation of aryl ha li des 11 ,RSC Advances, vol. 4, No. 78, Jan. 1, 2014 (Jan. 1, 2014), pp. 41631-41635, XP055719130.
Yadav MR et al.: "Synthesis and anti-inflammatory activity of 2,3-diaryl-4(3H)-quinazolinones", Chemistry of Heterocyclic Compounds, Kluwer Academic Publishers-Plenum Publishers, NL, vol. 42, No. 8, Aug. 1, 2006 (Aug. 1, 2006), pp. 1038-1045, XP019448301.
Susan M. Westaway et al.: "Cell Penetrant Inhibitors of the KDM4 and KDM5 Families of Histone Lysine Demethylases. 2. Pyrido[3,4-d ]pyrimidin-4(3 H )-one Derivatives", Journal of Medicinal Chemistry,vol. 59, No. 4, Jan. 15, 2016 (Jan. 15, 2016), pp. 1370-1387, XP055719181.
Crespo MI et al.: "Design, Synthesis, and Biological Activities of New Thieno[3,2-d]pyrimidines as Selective Type 4 Phosphodiesterase Inhibitors", Journal of Medicinal Chemistry, American Chemical Society, US, vol. 41, Jan. 1, 1998 (Jan. 1, 1998), pp. 4021-4035, XP002173938.
Extended European Search Report issued by the European Patent Office in European Application No. 17884336.3 dated Dec. 4, 2020.
Preuss et al.: "High-Throughput Screening for Small-Molecule Inhibitors of Plasmodium falciparum Glucose-6-Phosphate Dehydrogenase 6-Phosphogluconolactonase", Journal of Biomolecular Screening, vol. 17, No. 6, Apr. 11, 2012 (Apr. 11, 2012), pp. 738-751.
Database GNPD [Online] MINTEL; Jul. 8, 2005 (Jul. 8, 2005), anonymous: 11 Compound Summary for CID 79948811 , XP055531226, retrieved from www.gnpd.com Database accession No. 799488 * p. 3 *.
Anonymus 114-[5-Ch loro-3-(5-methylfuran-2-yl) -1-ben z ofuran-2-yl]butan-2-one : C17H15CI03—PubChem 11 , • Jul. 8, 2005 (Jul. 8, 2005), XP055686676, Retrieved from the Internet: URL:https://pubchem.ncbi.nlm.nih.gov/compound/799485. Retrieved on Apr. 17, 2020] * p. 2 *.

V.T. Abaev et al: 11 Polyfuryl( aryl) al kanes and their derivatives 16. Convenient path to benzofuran ketones 11 , Chemistry of Heterocyclic Compounds, vol. 34, No. 5, May 1, 1998 (May 1, 1998), pp. 529-532, XP055686719, New York. ISSN: 0009-3122, DOI: 10.1007/BF02290932. *abstract*.
P. Cermakova et al.: 11 Heart failure and Alzheimer's disease 11, Journal of Internal Medicine, vol. 277, No. 4, Jul. 15, 2014 (Jul. 15, 2014) pp. 406-425, XP055687154, GB ISSN: 0954-6820, DOI: 10.1111/joim.12287 *pp. 406, 409 *.
Ono Masahiro et al.: 11 Novel benzofuran derivatives for PET imaging of beta.-amyloid plaques in Alzheimer's disease brains 11, Journal of Medicinal Chemistry, American Chemical Society, US, vol. 49, No. 9, Apr. 4, 2006 (Apr. 4, 2006), pp. 2725-2730, XP002419265, ISSN: 0022-2623, DOI: 10.1021/JM051176K *abstract* *p. 2727; figure 5*.
Supplementary European Search Report of the European Patent Office dated May 4, 2020 in EP 17 88 4772.
Hisano, T., et al. "Studies on Organosulfur Compounds. XII. Syntheses and Pharmacological Activities of 2-Heterocyclic Substituted 4(3H)-Quinazolinones," Chern. Pharm. Bull. 21 (9) 1975 pp. 1910-1916.
He, F., et al. "Asperterrestide A, a Cytotoxic Cyclic Tetrapeptide from the Marine-Derived Fungus Aspergillus terreus SCSGAF0162" Journal of Natural Products, 76, 2013.
Wang, Yi, et al. "Three New Compounds from Aspergillus terreus PT06-2 Grown in a High Salt Medium" Marine Drugs 2011,9,1368-1378.
Ammar, YA, et al. "Synthesis of Some Biologically Active 4(3H)-Quinazolinones Derived from 2,3-Pyridine Dicarboxylic Anhydride" Chemical Sciences Journal, vol. 2011.
Kalusa, A. et al., An efficient synthesis of 2,3-diaryl-(3H)-quinazolin-4-ones via imidoyl chlorides, Tetrahedron Letters, 2008, vol. 49, No. 41, pp. 5840-5842.
Butin, A.V., et al. "Polyfuryl(aryl)alkanes and their derivatives. 17. Synthesis of Compounds of the oxazulene series" Chemistry of Heterocyclic Compounds, vol. 34, No. 7, 1998.
Abaev, V.T., et al. "Polyfuryl(aryl)alkanes and their derivatives. 16. Convenient path to benzofuran ketones" Chemistry of Heterocyclic Compounds, vol. 34, No. 5, 1998.
Deorha, Daleep Singh; Gupta, Padma, Modified synthesis of several [3-(2-benzofuryl)propionic acids, Chemische Berichte, 1966, vol. 99, No. 6, pp. 2063-2065. (Reference in German) English translation provided.
Office Action issued by the US Patent and Trademark Office in corresponding U.S. Appl. No. 16/471,363 dated Feb. 11, 2022.

BENZOFURAN, BENZOTHIOPHENE, AND INDOLE ANALOGS THAT INHIBIT THE FORMATION OF TAU OLIGOMERS AND THEIR METHOD OF USE

STATEMENT OF FEDERALLY FUNDED RESEARCH

The U.S. Government has a paid-up license in this invention and the right in limited circumstances to require the patent owner to license others on reasonable terms as provided for by the terms of grant number 5R44AG029777-05, 2R44AG029777-04, 5R44AG029777-03, 2R44AG029777-02A1, 1R43AG029777-01, 1R44AG053150-01, and 5R44AG053150-02 awarded by the National Institute On Aging of the National Institutes of Health.

FIELD OF INVENTION

The present invention describes novel benzofurans, benzothiophenes and indoles useful as inhibitors of tau oligomer formation, useful for the treatment of neurodegenerative diseases and related conditions. The invention also relates to the pharmaceutically acceptable salts of said compounds, processes for the preparation of said compounds, intermediates used in the preparation of said compounds, and pharmaceutical compositions containing said compounds. The invention further relates to methods of use of said compounds, salts of said compounds, and said compositions in treating neurodegenerative diseases and related conditions.

BACKGROUND OF THE INVENTION

There is a large and growing unmet need for disease-modifying drugs for Alzheimer's disease (AD). The prevalence of AD is increasing worldwide due to demographic shifts resulting from an aging population, and ending AD would save 500,000 lives a year. It is the most costly disease in the US with a financial burden of over $259 billion in 2017 direct costs that is estimated to increase to $1.1 trillion per year by 2050. Women are much more likely to develop AD and to bear the burden of caregiving (Alzheimer's Association, Facts and Figures 2017). Accordingly, the primary goal of the National Alzheimer's Project is to prevent and effectively treat AD by 2025. As all Phase 3 drug development programs to date based on the amyloid hypothesis have failed to meet their clinical endpoints, there is a need for alternative approaches for the development of AD therapeutics such as targeting tau (Giacobini and Gold, Nature Reviews Neurology, 2013, 9:677; Li and Gotz J. Nat Rev Drug Discov. 2017, 16:863).

An alternative approach to treating AD focuses on developing disease-modifying therapeutics (DMTs) that inhibit tau self-association into oligomers and larger tau aggregates. Neurofibrillary tangles are pathological hallmarks associated with AD and related tauopathies, but their role in causing neurodegeneration is questionable. See Gerson and Kayed, Front Neurol. 2013, 17, 93. Multiple studies have shown that tau oligomers, not fibrils or tangles, are closely correlated with neuronal loss and memory impairment. See: Patterson et al., J. Biol Chem. 2011, 286, 23063 and Lasagna-Reeves et al., FASEB J. 2012, 26, 1946. Significantly, Oligomerix has shown that tau oligomers cause disruption of neuronal signaling and inhibit the formation of memory in mice. Memory formation was impaired following administration of oligomeric tau to hippocampi, areas of the brain involved in short-term memory formation. But similar treatment with tau monomer (tau that did not self-associate) did not have an effect. This impairment of memory was also found using oligomers formed from tau purified from human AD brain specimens using a method that preserved tau modifications associated with AD. Memory-specific mechanisms involved in gene regulation were shown to be disrupted by these extracellular tau oligomers. See Moe, et al., Alzheimer's & Dementia 2010, S277 and Fá, et al., Sci. Rep. 2016, 6, 19393. Subsequent studies have corroborated our findings showing that tau oligomers caused impairment of memory formation and induced synaptic and mitochondrial dysfunction in wild-type mice (Lasagna-Reeves, et al., Mol Neurodegener. 2011, 6, 39), and in a mouse model reproducing the spread of tau pathology in AD (Polydoro et al., Acta Neuropathol. 2014, 127, 257). Oligomerix has also found, in collaboration with Dr. Michael Sierks' laboratory at Arizona State University, that specific forms of tau oligomers are toxic when applied to cultured neurons, whereas tau monomer was not toxic at the same concentrations. See Tian et al., Int J Cell Biol., 2013, 2013. The tau oligomer target for the development of therapeutics has been validated in htau (human tau) by treatment with curcumin (Ma et al., J Biol Chem. 2013, 288, 4056) and by a passive immunotherapeutic approach directed at tau oligomers (Castillo-Carranza et al., J Alzheimers Dis. 2014, 40 Suppl 1, S97).

The pattern of the spread of tau pathology in AD is very consistent and thus can be used to stage the disease (Alafuzoff et al., Brain Pathol. 2008, 18, 484). The observation that tau pathology progresses to synaptically connected regions of the brain led to the hypothesis that tau can transmit its own pathology from a diseased to a healthy neuron. Recent studies show that tau aggregates and specifically tau oligomers isolated from AD brain may act as templates for the misfolding and aggregation of native tau, thereby seeding the spread of the toxic forms of the protein. See Funk et al., J Biol Chem. 2015, 290, 21652 and Mirbaha et al., J Biol Chem. 2015, 290, 14893. These studies, taken together, strongly suggest that targeting tau oligomers should improve learning and memory and inhibit disease progression in AD, related tauopathies, and neurodegenerative diseases. Immunotherapeutic approaches targeting extracellular aggregated tau are in clinical development for AD and other tauopathies (West et al. J Prev Alzheimers Dis. 2017, 4:236). However, a small molecule approach would be more economical in view of the chronic course of the disease and the cost-differential between antibody infusions and an orally available drug. Also, small molecule drugs can more readily cross the plasma membrane and thus can directly target tau self-association intracellularly.

There are currently no Disease-Modifying Therapies (DMTs) for AD and the commercially available symptom modifying drugs are not very effective. However, several strategies are being used to develop drugs targeting tau including mechanisms of hyperphosphorylation, fibrillar aggregation, clearance of tau aggregates by macroautophagy, HSP90 inhibitors and immunotherapeutic approaches (Gruninger, Neuropathology and applied neurobiology 2015, 41, 81; Boutajangout et al., Gerontology 2014, 381; Moe, et al., Alzheimer's & Dementia 2012, P 458). However, there are no clinically approved therapies useful for the inhibition of tau oligomer formation, useful for the treatment of neurodegenerative diseases and related conditions.

There is a long-felt need for new therapies that inhibit the formation of tau oligomers that are useful for the treatment of Alzheimer's disease (AD) that are disease-modifying. The present invention addresses the need to inhibit the formation of tau oligomers that are useful for the treatment of Alzheimer's disease (AD). The present invention also addresses the long felt need for new treatments for and means of preventing diseases caused by or associated with tau based aggregates such as Amyotrophic lateral sclerosis/parkinsonism-dementia complex, argyrophilic grain dementia, corticobasal degeneration, Creutzfeldt-Jakob disease, dementia pugilistica/chronic traumatic encephalopathy, diffuse neurofibrillary tangles with calcification, Down's syndrome, frontotemporal dementia with parkinsonism linked to chromosome 17, Gerstmann-Sträussler-Scheinker disease, Hallervorden-Spatz disease, myotonic dystrophy, Niemann-Pick disease, type C, non-Guamanian motor neuron disease with neurofibrillary tangles, Pick's disease, postencephalitic parkinsonism, prion protein cerebral amyloid angiopathy, progressive subcortical gliosis, progressive supranuclear palsy, subacute sclerosing panencephalitis, and tangle only dementia.

SUMMARY OF THE INVENTION

The present invention relates to compounds of formula (I),

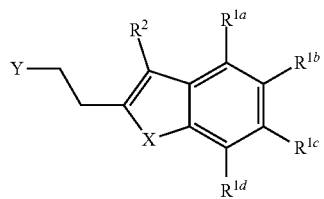

Including enantiomers, diastereomers, hydrates, solvates, pharmaceutically acceptable salts, and complexes thereof, wherein $R^{1a}$ and $R^{1d}$ are each independently selected from the group consisting of hydrogen, halogen, $C_{1-6}$ alkyl, $C_{1-6}$ alkoxy, $C_{1-6}$ haloalkyl, and $C_{1-6}$ haloalkoxy.

$R^{1b}$ and $R^{1c}$ are selected from the group consisting of hydrogen, halogen, optionally substituted aryl and optionally substituted heteroaryl;

When $R^{1b}$ is hydrogen, $R^{1c}$ is not hydrogen;
When $R^{1c}$ is hydrogen, $R^{1b}$ is not hydrogen;
$R^2$ is selected from the group consisting of $C_{1-6}$ alkyl, $C_{3-7}$ branched alkyl, $C_{1-6}$ alkylaryl, optionally substituted aryl and optionally substituted heteroaryl;
X is selected from the group consisting of oxygen, sulfur, NH, and $NR^5$;
$R^5$ is $C_{1-6}$ alkyl;
Y is selected from the group consisting of

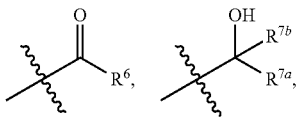

and optionally substituted 2-benzimidazole;
$R^6$ is selected from the group consisting of hydrogen, OH, $OR^{7c}$, optionally substituted $C_{1-6}$ alkyl, $NR^{3a}R^{3b}$, optionally substituted aryl, and optionally substituted heteroaryl;

$R^{3a}$ and $R^{3b}$ are independently selected from the group consisting of hydrogen and $C_{1-6}$ alkyl;
$R^{3a}$ and $R^{3b}$ are taken together with the atom to which they are bound to form an three to six membered saturated ring optionally substituted with a group selected from OH, $C_{1-6}$ alkyl, $NR^{8a}R^{8b}$ optionally including a member selected from the group consisting of O, $NR^8$, and S;
$R^8$ is selected from the group consisting of hydrogen, $C_{1-6}$ alkyl, and $CO(C_{1-6}alkyl)$;
$R^{8a}$ and $R^{8b}$ are independently selected from of hydrogen and $C_{1-6}$ alkyl.
$R^{7a}$ is selected from the group consisting of hydrogen and $C_{1-6}$ alkyl;
$R^{7b}$ is selected from the group consisting of $C_{1-6}$ alkyl, aryl, and heteroaryl;
and $R^{7c}$ is selected from the group consisting of $C_{1-6}$ alkyl and $C_{3-7}$ branched alkyl.

The compounds of the present invention include compounds having formula (II):

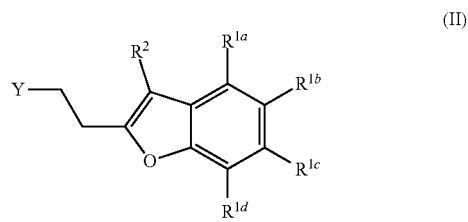

including enantiomers, diastereomers, hydrates, solvates, pharmaceutically acceptable salts, and complexes thereof, wherein, $R^{1a}$, $R^{1b}$, $R^{1c}$, $R^{1d}$, $R^2$, and Y are as defined for formula I.

The compounds of the present invention include compounds having formula (III):

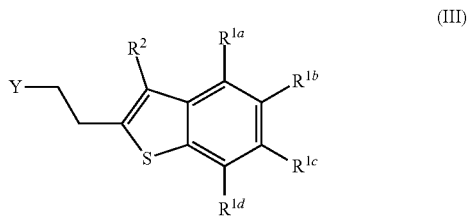

including enantiomers, diastereomers, hydrates, solvates, pharmaceutically acceptable salts, and complexes thereof, wherein $R^{1a}$, $R^{1b}$, $R^{1c}$, $R^{1d}$, $R^2$, and Y are as defined for formula I.

The compounds of the present invention include compounds having formula (IV):

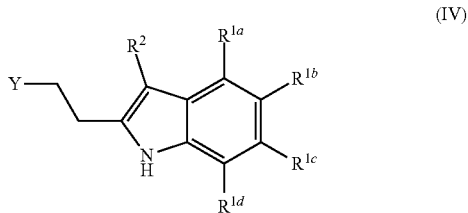

including enantiomers, diastereomers, hydrates, solvates, pharmaceutically acceptable salts, and complexes thereof, wherein $R^{1a}$, $R^{1b}$, $R^{1c}$, $R^{1d}$, $R^2$, and Y are as defined for formula I.

The compounds of the present invention include compounds having formula (V):

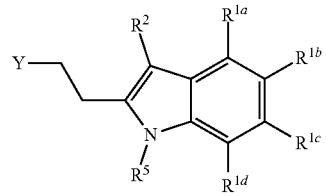

(V)

including enantiomers, diastereomers, hydrates, solvates, pharmaceutically acceptable salts, and complexes thereof, wherein $R^{1a}$, $R^{1b}$, $R^{1c}$, $R^{1d}$, $R^2$, $R^5$ and Y are as defined for formula I.

The compounds of the present invention include compounds having formula (VI):

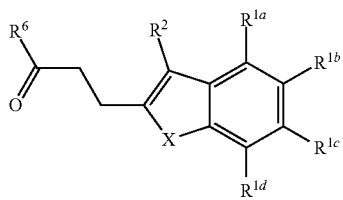

(VI)

including enantiomers, diastereomers, hydrates, solvates, pharmaceutically acceptable salts, and complexes thereof, wherein $R^{1a}$, $R^{1b}$, $R^{1c}$, $R^{1d}$, $R^2$, $R^5$, and X are as defined for formula I.

The compounds of the present invention include compounds having formula (VII):

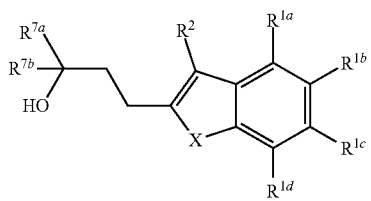

(VII)

including enantiomers, diastereomers, hydrates, solvates, pharmaceutically acceptable salts, and complexes thereof, wherein $R^{1a}$, $R^{1b}$, $R^{1c}$, $R^{1d}$, $R^2$, $R^{7a}$, $R^{7b}$ and X are as defined for formula I.

The compounds of the present invention include compounds having formula (VIII):

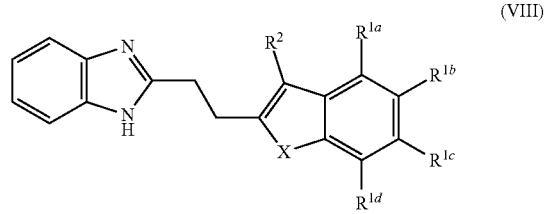

(VIII)

including enantiomers, diastereomers, hydrates, solvates, pharmaceutically acceptable salts, and complexes thereof, wherein $R^{1a}$, $R^{1b}$, $R^{1c}$, $R^{1d}$, $R^2$ and X are as defined for formula I.

The compounds of the present invention include compounds having formula (IX):

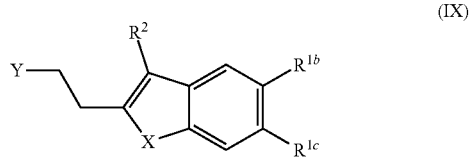

(IX)

including enantiomers, diastereomers, hydrates, solvates, pharmaceutically acceptable salts, and complexes thereof, wherein $R^{1b}$, $R^{1c}$, $R^2$, X and Y are as defined for formula I.

The compounds of the present invention include compounds having formula (X):

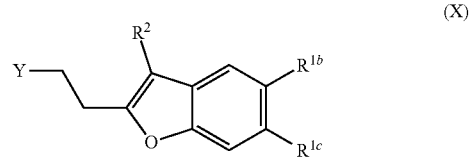

(X)

including enantiomers, diastereomers, hydrates, solvates, pharmaceutically acceptable salts, and complexes thereof, wherein $R^{1b}$, $R^{1c}$, $R^2$, and Y are as defined for formula I.

The compounds of the present invention include compounds having formula (XI):

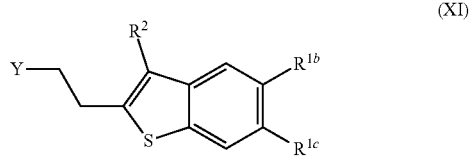

(XI)

including enantiomers, diastereomers, hydrates, solvates, pharmaceutically acceptable salts, and complexes thereof, wherein $R^{1b}$, $R^{1c}$, $R^2$, and Y are as defined for formula I.

The compounds of the present invention include compounds having formula (XII):

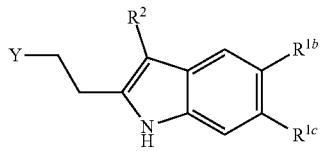

(XII)

including enantiomers, diastereomers, hydrates, solvates, pharmaceutically acceptable salts, and complexes thereof, wherein $R^{1b}$, $R^{1c}$, $R^2$, and Y are as defined for formula I.

The compounds of the present invention include compounds having formula (XIII):

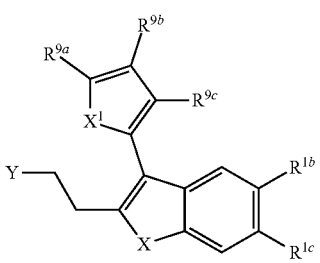

(XIII)

including enantiomers, diastereomers, hydrates, solvates, pharmaceutically acceptable salts, and complexes thereof wherein $R^{1b}$, $R^{1c}$, X and Y are as defined for formula I; $R^{9a}$, $R^{9b}$, and $R^{9c}$ are independently selected from the group consisting of hydrogen, halogen, and $C_{1-6}$ alkyl;

and $X^1$ is selected from the group consisting of oxygen and sulfur.

The compounds of the present invention include compounds having formula (XIV):

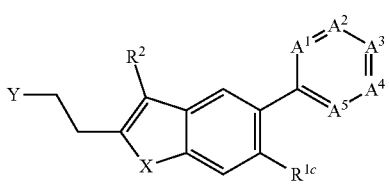

(XIV)

including enantiomers, diastereomers, hydrates, solvates, pharmaceutically acceptable salts, and complexes thereof wherein $R^{1c}$, $R^2$, X and Y are as defined for formula I;

$A^1$, $A^2$, $A^3$, $A^4$, and $A^5$ are selected from the group consisting of nitrogen and $CR^{10}$;

No more than two of $A^1$, $A^2$, $A^3$, $A^4$, and $A^5$ may be nitrogen;

$R^{10}$ is selected from the group consisting of hydrogen, $C_{1-6}$ alkyl, $C_{1-6}$ haloalkyl, $C_{1-6}$ haloalkoxy, $C_{1-6}$ alkoxy, halogen, hydroxy, and $NHSO_2R^{11}$;

and $R^{11}$ is independently selected from the group consisting of hydrogen and $C_{1-6}$ alkyl.

The compounds of the present invention include compounds having formula (XIVa):

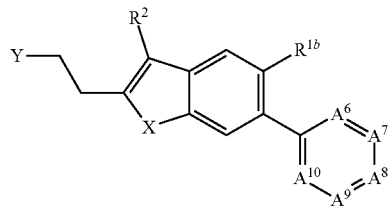

(XIVa)

including enantiomers, diastereomers, hydrates, solvates, pharmaceutically acceptable salts, and complexes thereof wherein $R^{1b}$, $R^2$, X and Y are as defined for formula I;

$A^6$, $A^7$, $A^8$, $A^9$, and $A^{10}$ are selected from the group consisting of nitrogen and $CR^{10}$;

No more than two of $A^6$, $A^7$, $A^8$, $A^9$, and $A^{10}$ may be nitrogen;

$R^{10}$ is selected from the group consisting of hydrogen, $C_{1-6}$ alkyl, $C_{1-6}$ haloalkyl, $C_{1-6}$ haloalkoxy, $C_{1-6}$ alkoxy, halogen, hydroxy, and $NHSO_2R^{11}$;

and $R^{11}$ is independently selected from the group consisting of hydrogen and $C_{1-6}$ alkyl.

The compounds of the present invention include compounds having formula (XIVb):

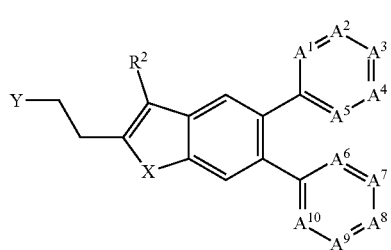

(XIVb)

including enantiomers, diastereomers, hydrates, solvates, pharmaceutically acceptable salts, and complexes thereof wherein $R^2$, X and Y are as defined for formula I;

$A^1$, $A^2$, $A^3$, $A^4$, $A^5$, $A^6$, $A^7$, $A^8$, $A^9$, and $A^{10}$ are selected from the group consisting of nitrogen and $CR^{10}$;

No more than two of $A^1$, $A^2$, $A^3$, $A^4$, and $A^5$ may be nitrogen; No more than two of $A^6$, $A^7$, $A^8$, $A^9$, and $A^{10}$ may be nitrogen;

$R^{10}$ is selected from the group consisting of hydrogen, $C_{1-6}$ alkyl, $C_{1-6}$ haloalkyl, $C_{1-6}$ haloalkoxy, $C_{1-6}$ alkoxy, halogen, hydroxy, and $NHSO_2R^{11}$;

and $R^{11}$ is independently selected from the group consisting of hydrogen and $C_{1-6}$ alkyl.

The compounds of the present invention include compounds having formula (XV):

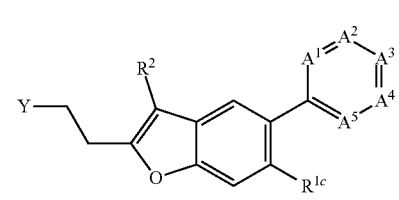

(XV)

including enantiomers, diastereomers, hydrates, solvates, pharmaceutically acceptable salts, and complexes thereof wherein $R^{1c}$, $R^2$ and Y are as defined for formula I;
$A^1, A^2, A^3, A^4$, and $A^5$ are selected from the group consisting of nitrogen and $CR^{10}$;
No more than two of $A^1, A^2, A^3, A^4$, and $A^5$ may be nitrogen;
$R^{10}$ is selected from the group consisting of hydrogen, $C_{1-6}$ alkyl, $C_{1-6}$ haloalkyl, $C_{1-6}$ haloalkoxy, $C_{1-6}$ alkoxy, halogen, hydroxy, and $NHSO_2R^{11}$;
and $R^{11}$ is independently selected from the group consisting of hydrogen and $C_{1-6}$ alkyl.

The compounds of the present invention include compounds having formula (XVa):

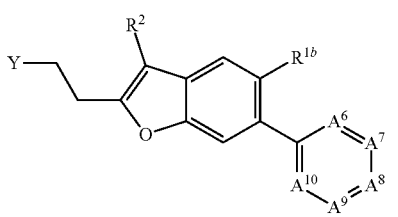

(XVa)

including enantiomers, diastereomers, hydrates, solvates, pharmaceutically acceptable salts, and complexes thereof wherein $R^{1b}$, $R^2$ and Y are as defined for formula I;
$A^6, A^7, A^8, A^9$, and $A^{10}$ are selected from the group consisting of nitrogen and $CR^{10}$;
No more than two of $A^6, A^7, A^8, A^9$, and $A^{10}$ may be nitrogen;
$R^{10}$ is selected from the group consisting of hydrogen, $C_{1-6}$ alkyl, $C_{1-6}$ haloalkyl, $C_{1-6}$ haloalkoxy, $C_{1-6}$ alkoxy, halogen, hydroxy, and $NHSO_2R^{11}$;
and $R^{11}$ is independently selected from the group consisting of hydrogen and $C_{1-6}$ alkyl.

The compounds of the present invention include compounds having formula (XVb):

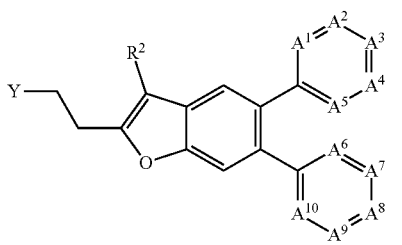

(XIVb)

including enantiomers, diastereomers, hydrates, solvates, pharmaceutically acceptable salts, and complexes thereof wherein $R^2$ and Y are as defined for formula I;
$A^1, A^2, A^3, A^4, A^5, A^6, A^7, A^8, A^9$, and $A^{10}$ are selected from the group consisting of nitrogen and $CR^{10}$;
No more than two of $A^1, A^2, A^3, A^4$, and $A^5$ may be nitrogen;
No more than two of $A^6, A^7, A^8, A^9$, and $A^{10}$ may be nitrogen;
$R^{10}$ is selected from the group consisting of hydrogen, $C_{1-6}$ alkyl, $C_{1-6}$ haloalkyl, $C_{1-6}$ haloalkoxy, $C_{1-6}$ alkoxy, halogen, hydroxy, and $NHSO_2R^{11}$;
and $R^{11}$ is independently selected from the group consisting of hydrogen and $C_{1-6}$ alkyl.

The compounds of the present invention include compounds having formula (XVI):

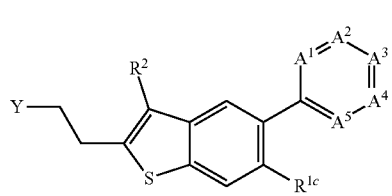

(XVI)

including enantiomers, diastereomers, hydrates, solvates, pharmaceutically acceptable salts, and complexes thereof wherein $R^{1c}$, $R^2$ and Y are as defined for formula I;
$A^1, A^2, A^3, A^4$, and $A^5$ are selected from the group consisting of nitrogen and $CR^{10}$;
No more than one of $A^1, A^2, A^3, A^4$, and $A^5$ may be nitrogen;
$R^{10}$ is selected from the group consisting of hydrogen, $C_{1-6}$ alkyl, $C_{1-6}$ haloalkyl, $C_{1-6}$ haloalkoxy, $C_{1-6}$ alkoxy, halogen, hydroxy, and $NHSO_2R^{11}$;
and $R^{11}$ is independently selected from the group consisting of hydrogen and $C_{1-6}$ alkyl.

The compounds of the present invention include compounds having formula (XVIa):

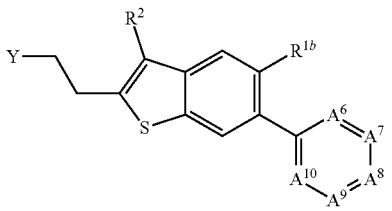

(XVIa)

including enantiomers, diastereomers, hydrates, solvates, pharmaceutically acceptable salts, and complexes thereof wherein $R^{1b}$, $R^2$ and Y are as defined for formula I;
$A^6, A^7, A^8, A^9$, and $A^{10}$ are selected from the group consisting of nitrogen and $CR^{10}$;
No more than two of $A^6, A^7, A^8, A^9$, and $A^{10}$ may be nitrogen;
$R^{10}$ is selected from the group consisting of hydrogen, $C_{1-6}$ alkyl, $C_{1-6}$ haloalkyl, $C_{1-6}$ haloalkoxy, $C_{1-6}$ alkoxy, halogen, hydroxy, and $NHSO_2R^{11}$;
and $R^{11}$ is independently selected from the group consisting of hydrogen and $C_{1-6}$ alkyl.

The compounds of the present invention include compounds having formula (XVIb):

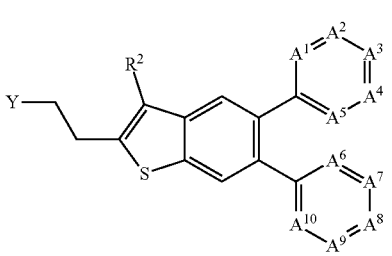

(XVIb)

including enantiomers, diastereomers, hydrates, solvates, pharmaceutically acceptable salts, and complexes thereof wherein $R^2$ and Y are as defined for formula I;

$A^1, A^2, A^3, A^4, A^5, A^6, A^7, A^8, A^9$, and $A^{10}$ are selected from the group consisting of nitrogen and $CR^{10}$;

No more than two of $A^1, A^2, A^3, A^4$, and $A^5$ may be nitrogen;

No more than two of $A^6$, $A^7$, $A^8$, $A^9$, and $A^{10}$ may be nitrogen;

$R^{10}$ is selected from the group consisting of hydrogen, $C_{1-6}$ alkyl, $C_{1-6}$ haloalkyl, $C_{1-6}$ haloalkoxy, $C_{1-6}$ alkoxy, halogen, hydroxy, and $NHSO_2R^{11}$;

and $R^{11}$ is independently selected from the group consisting of hydrogen and $C_{1-6}$ alkyl.

The compounds of the present invention include compounds having formula (XVII):

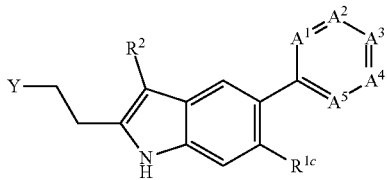

(XVII)

including enantiomers, diastereomers, hydrates, solvates, pharmaceutically acceptable salts, and complexes thereof wherein $R^{1c}$, $R^2$ and Y are as defined for formula I;

$A^1, A^2, A^3, A^4$, and $A^5$ are selected from the group consisting of nitrogen and $CR^{10}$;

No more than one of $A^1, A^2, A^3, A^4$, and $A^5$ may be nitrogen;

$R^{10}$ is selected from the group consisting of hydrogen, $C_{1-6}$ alkyl, $C_{1-6}$ haloalkyl, $C_{1-6}$ haloalkoxy, $C_{1-6}$ alkoxy, halogen, hydroxy, and $NHSO_2R^{11}$;

and $R^{11}$ is independently selected from the group consisting of hydrogen and $C_{1-6}$ alkyl.

The compounds of the present invention include compounds having formula (XVIIa):

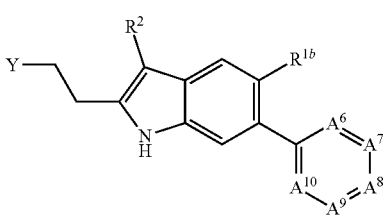

(XVIIa)

including enantiomers, diastereomers, hydrates, solvates, pharmaceutically acceptable salts, and complexes thereof wherein $R^2$, $R^{1b}$ and Y are as defined for formula I;

$A^6, A^7, A^8, A^9$, and $A^{10}$ are selected from the group consisting of nitrogen and $CR^{10}$;

No more than two of $A^6$, $A^7$, $A^8$, $A^9$, and $A^{10}$ may be nitrogen;

$R^{10}$ is selected from the group consisting of hydrogen, $C_{1-6}$ alkyl, $C_{1-6}$ haloalkyl, $C_{1-6}$ haloalkoxy, $C_{1-6}$ alkoxy, halogen, hydroxy, and $NHSO_2R^{11}$;

and $R^{11}$ is independently selected from the group consisting of hydrogen and $C_{1-6}$ alkyl.

The compounds of the present invention include compounds having formula (XVIIb):

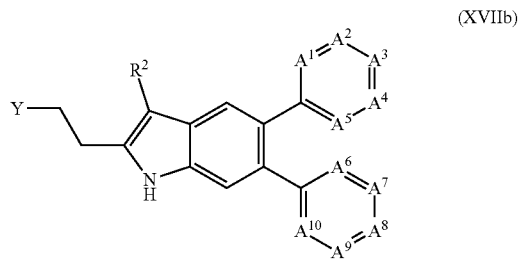

(XVIIb)

including enantiomers, diastereomers, hydrates, solvates, pharmaceutically acceptable salts, and complexes thereof wherein $R^2$ and Y are as defined for formula I;

$A^1, A^2, A^3, A^4, A^5, A^6, A^7, A^8, A^9$, and $A^{10}$ are selected from the group consisting of nitrogen and $CR^{10}$;

No more than two of $A^1, A^2, A^3, A^4$, and $A^5$ may be nitrogen;

No more than two of $A^6$, $A^7$, $A^8$, $A^9$, and $A^{10}$ may be nitrogen;

$R^{10}$ is selected from the group consisting of hydrogen, $C_{1-6}$ alkyl, $C_{1-6}$ haloalkyl, $C_{1-6}$ haloalkoxy, $C_{1-6}$ alkoxy, halogen, hydroxy, and $NHSO_2R^{11}$;

and $R^{11}$ is independently selected from the group consisting of hydrogen and $C_{1-6}$ alkyl.

The compounds of the present invention include compounds having formula (XVIII):

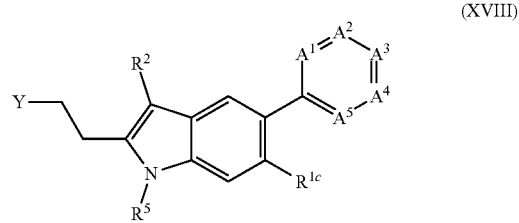

(XVIII)

including enantiomers, diastereomers, hydrates, solvates, pharmaceutically acceptable salts, and complexes thereof wherein $R^{1c}$, $R^2$, $R^5$ and Y are as defined for formula I;

$A^1, A^2, A^3, A^4$, and $A^5$ are selected from the group consisting of nitrogen and $CR^{10}$;

No more than one of $A^1, A^2, A^3, A^4$, and $A^5$ may be nitrogen;

$R^{10}$ is selected from the group consisting of hydrogen, $C_{1-6}$ alkyl, $C_{1-6}$ haloalkyl, $C_{1-6}$ haloalkoxy, $C_{1-6}$ alkoxy, halogen, hydroxy, and $NHSO_2R^{11}$;

and $R^{11}$ is independently selected from the group consisting of hydrogen and $C_{1-6}$ alkyl.

The compounds of the present invention include compounds having formula (XVIIIa):

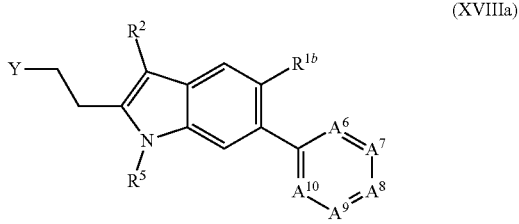

(XVIIIa)

including enantiomers, diastereomers, hydrates, solvates, pharmaceutically acceptable salts, and complexes thereof wherein $R^{1b}$, $R^2$, $R^5$ and Y are as defined for formula I;
$A^6$, $A^7$, $A^8$, $A^9$, and $A^{10}$ are selected from the group consisting of nitrogen and $CR^{10}$;
No more than two of $A^6$, $A^7$, $A^8$, $A^9$, and $A^{10}$ may be nitrogen;
$R^{10}$ is selected from the group consisting of hydrogen, $C_{1-6}$ alkyl, $C_{1-6}$ haloalkyl, $C_{1-6}$ haloalkoxy, $C_{1-6}$ alkoxy, halogen, hydroxy, and $NHSO_2R^{11}$;
and $R^{11}$ is independently selected from the group consisting of hydrogen and $C_{1-6}$ alkyl.

The compounds of the present invention include compounds having formula (XVIIIb):

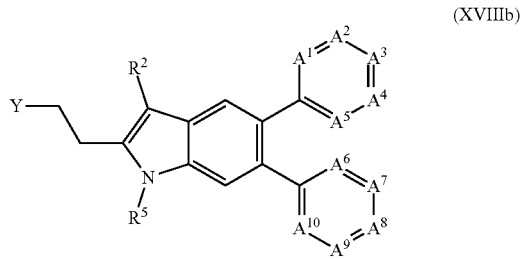

(XVIIIb)

including enantiomers, diastereomers, hydrates, solvates, pharmaceutically acceptable salts, and complexes thereof wherein $R^2$, $R^1$ and Y are as defined for formula I;
$A^1$, $A^2$, $A^3$, $A^4$, $A^5$, $A^6$, $A^7$, $A^8$, $A^9$, and $A^{10}$ are selected from the group consisting of nitrogen and $CR^{10}$;
No more than two of $A^1$, $A^2$, $A^3$, $A^4$, and $A^5$ may be nitrogen;
No more than two of $A^6$, $A^7$, $A^8$, $A^9$, and $A^{10}$ may be nitrogen;
$R^{10}$ is selected from the group consisting of hydrogen, $C_{1-6}$ alkyl, $C_{1-6}$ haloalkyl, $C_{1-6}$ haloalkoxy, $C_{1-6}$ alkoxy, halogen, hydroxy, and $NHSO_2R^{11}$;
and $R^{11}$ is independently selected from the group consisting of hydrogen and $C_{1-6}$ alkyl.

The present invention further relates to compositions comprising: an effective amount of one or more compounds according to the present invention and an excipient.

The present invention also relates to a method for treating or preventing diseases that involve the formation of tau oligomers, including, for example, Alzheimer's disease, Amyotrophic lateral sclerosis/parkinsonism-dementia complex, argyrophilic grain dementia, corticobasal degeneration, Creutzfeldt-Jakob disease, dementia pugilistica/chronic traumatic encephalopathy, diffuse neurofibrillary tangles with calcification, Down's syndrome, frontotemporal dementia with parkinsonism linked to chromosome 17, Gerstmann-Sträussler-Scheinker disease, Hallervorden-Spatz disease, myotonic dystrophy, Niemann-Pick disease, type C, non-Guamanian motor neuron disease with neurofibrillary tangles, Pick's disease, postencephalitic parkinsonism, prion protein cerebral amyloid angiopathy, progressive subcortical gliosis, progressive supranuclear palsy, subacute sclerosing panencephalitis, and tangle only dementia, said method comprising administering to a subject an effective amount of a compound or composition according to the present invention.

The present invention yet further relates to a method for treating or preventing diseases that involve the formation of tau oligomers, including, for example, Alzheimer's disease, Amyotrophic lateral sclerosis/parkinsonism-dementia complex, argyrophilic grain dementia, corticobasal degeneration, Creutzfeldt-Jakob disease, dementia pugilistica/chronic traumatic encephalopathy, diffuse neurofibrillary tangles with calcification, Down's syndrome, frontotemporal dementia with parkinsonism linked to chromosome 17, Gerstmann-Sträussler-Scheinker disease, Hallervorden-Spatz disease, myotonic dystrophy, Niemann-Pick disease, type C, non-Guamanian motor neuron disease with neurofibrillary tangles, Pick's disease, postencephalitic parkinsonism, prion protein cerebral amyloid angiopathy, progressive subcortical gliosis, progressive supranuclear palsy, subacute sclerosing panencephalitis, and tangle only dementia, wherein said method comprises administering to a subject a composition comprising an effective amount of one or more compounds according to the present invention and an excipient.

The present invention also relates to a method for treating or preventing disease or conditions associated with Alzheimer's disease, Amyotrophic lateral sclerosis/parkinsonism-dementia complex, argyrophilic grain dementia, corticobasal degeneration, Creutzfeldt-Jakob disease, dementia pugilistica/chronic traumatic encephalopathy, diffuse neurofibrillary tangles with calcification, Down's syndrome, frontotemporal dementia with parkinsonism linked to chromosome 17, Gerstmann-Sträussler-Scheinker disease, Hallervorden-Spatz disease, myotonic dystrophy, Niemann-Pick disease, type C, non-Guamanian motor neuron disease with neurofibrillary tangles, Pick's disease, postencephalitic parkinsonism, prion protein cerebral amyloid angiopathy, progressive subcortical gliosis, progressive supranuclear palsy, subacute sclerosing panencephalitis, and tangle only dementia, and diseases that involve the formation of tau oligomers. Said methods comprise administering to a subject an effective amount of a compound or composition according to the present invention.

One embodiment of the present invention relates to a method for treating or preventing disease or conditions associated with Alzheimer's disease, Amyotrophic lateral sclerosis/parkinsonism-dementia complex, argyrophilic grain dementia, corticobasal degeneration, Creutzfeldt-Jakob disease, dementia pugilistica/chronic traumatic encephalopathy, diffuse neurofibrillary tangles with calcification, Down's syndrome, frontotemporal dementia with parkinsonism linked to chromosome 17, Gerstmann-Sträussler-Scheinker disease, Hallervorden-Spatz disease, myotonic dystrophy, Niemann-Pick disease, type C, non-Guamanian motor neuron disease with neurofibrillary tangles, Pick's disease, postencephalitic parkinsonism, prion protein cerebral amyloid angiopathy, progressive subcortical gliosis, progressive supranuclear palsy, subacute sclerosing panencephalitis, and tangle only dementia, and diseases that involve the formation of tau oligomers, wherein said method comprises administering to a subject a composition comprising an effective amount of one or more compounds according to the present invention and a pharmaceutically acceptable carrier.

The present invention also relates to a method for treating or preventing disease or conditions associated with the formation of tau oligomers. Said method comprises administering to a subject an effective amount of a compound or composition according to the present invention.

The present invention yet further relates to a method for treating or preventing disease or conditions associated with the formation of tau oligomers, wherein said method comprises administering to a subject a pharmaceutical composition comprising an effective amount of one or more compounds according to the present invention and an excipient.

The present invention further relates to a method for heating or preventing diseases that involve the formation of tau oligomers, including, for example, Alzheimer's disease, Amyotrophic lateral sclerosis/parkinsonism-dementia complex, argyrophilic grain dementia, corticobasal degeneration, Creutzfeldt-Jakob disease, dementia pugilistica/chronic traumatic encephalopathy, diffuse neurofibrillary tangles with calcification, Down's syndrome, frontotemporal dementia with parkinsonism finked to chromosome 17, Gerstmann-Sträussler-Scheinker disease, Hallervorden-Spatz disease, myotonic dystrophy, Niemann-Pick disease, type C, non-Guamanian motor neuron disease with neurofibrillary tangles, Pick's disease, postencephalitic parkinsonism, prion protein cerebral amyloid angiopathy, progressive subcortical gliosis, progressive supranuclear palsy, subacute sclerosing panencephalitis, and tangle only dementia, said method comprising administering to a subject an effective amount of a compound or composition according to the present invention and an effective amount of another compound, believed to be helpful in treating Alzheimer's disease when administered in conjunction with a compound of the present invention, such as Donepezil (Aricept®), Galantamine (Razadyne®), Memantine (Namenda®), Rivastigmine (Exelon®), Donepezil/Memantine (Namzaric®), AC-1204 (caprylic triglyceride), ACI-35, AD-4833/TOMM40, aducanumab (BIIB037), ALZ-801, ANAVEX 2-73/donepezil, AVN-101, AVN-322, AVP-786, AVP-923, AZD3293, azeliragon (TTP488), BAN2401, BI 409306, bisnorcymserine, bryostatin-1, CAD106, CPC-201, crenezumab, E2609, ELND005, encenicline, gantenerumab, GC021109, idalopirdine, Immune globulin, JNJ-54861911, LMTX, Lu-AF20513, LY3002813 (N3pG-Aβ mAb), MEDI1814, mGlu2 agonist, MK-7622, MK-8931, MSDC-0160, NIC-515, PF-05212377, PF-06648671, Posiphen® (R-phenserine), PTI-80, RG1577, RG7345, rilapladib, RVT-101, RVX208, SAR228810, sGC 1061 (nomethiazole), solanezumab, SUVN-502, SUVN-G3031, T-817MA, T3D-959, TPI287 (abeotaxane), UB-311, and VX-745.

The present invention further relates to a method of diagnosing diseases that involve the formation of tau oligomers using Positron Emission Technology (PET) or Single Photon Emission Computed Tomography (SPECT) imaging probes. Diseases including, for example, Alzheimer's disease, Amyotrophic lateral sclerosis/parkinsonism-dementia complex, argyrophilic grain dementia, corticobasal degeneration, Creutzfeldt-Jakob disease, dementia pugilistica/chronic traumatic encephalopathy, diffuse neurofibrillary tangles with calcification, Down's syndrome, frontotemporal dementia with parkinsonism linked to chromosome 17, Gerstmann-Sträussler-Scheinker disease, Hallervorden-Spatz disease, myotonic dystrophy, Niemann-Pick disease, type C, non-Guamanian motor neuron disease with neurofibrillary tangles. Pick's disease, postencephalitic parkinsonism, prion protein cerebral amyloid angiopathy, progressive subcortical gliosis, progressive supranuclear palsy, subacute sclerosing panencephalitis, and tangle only dementia, said method comprising administering to a subject an effective amount of a PET or SPECT compound or composition according to the present invention and scanning the patient with a (PET) or SPECT imaging system.

The present invention further relates to a process for preparing the inhibitors of tau oligomer formation of the present invention.

These and other objects, features, and advantages will become apparent to those of ordinary skill in the art from a reading of the following detailed description and the appended claims. All percentages, ratios and proportions herein are by weight, unless otherwise specified. All temperatures are in degrees Celsius (° C.) unless otherwise specified. All documents cited are in relevant part, incorporated herein by reference; the citation of any document is not to be construed as an admission that it is prior art with respect to the present invention.

DETAILED DESCRIPTION OF THE INVENTION

The inhibitors of tau oligomer formation of the present invention are capable of treating and preventing diseases associated with the formation of tau oligomers, for example Alzheimer's disease, Amyotrophic lateral sclerosis/parkinsonism-dementia complex, argyrophilic grain dementia, corticobasal degeneration, Creutzfeldt-Jakob disease, dementia pugilistica/chronic traumatic encephalopathy, diffuse neurofibrillary tangles with calcification, Down's syndrome, frontotemporal dementia with parkinsonism linked to chromosome 17, Gerstmann-Sträussler-Scheinker disease, Hallervorden-Spatz disease, myotonic dystrophy, Niemann-Pick disease, type C, non-Guamanian motor neuron disease with neurofibrillary tangles. Pick's disease, postencephalitic parkinsonism, prion protein cerebral amyloid angiopathy, progressive subcortical gliosis, progressive supranuclear palsy, subacute sclerosing panencephalitis, and tangle only dementia. Further, without wishing to be limited by theory, it is believed that inhibitors of tau oligomer formation of the present disclosure can ameliorate, abate, otherwise cause to be controlled, diseases associated with the formation of tau oligomers.

Throughout the description, where compositions are described as having, including, or comprising specific components, or where processes are described as having, including, or comprising specific process steps, it is contemplated that certain compositions of the present teachings also consist essentially of, or consist of, the recited components, and that the processes of the present teachings also consist essentially of, or consist of, the recited processing steps.

In the application, where an element or component is said to be included in and/or selected from a list of recited elements or components, it should be understood that the element or component can be any one of the recited elements or components and can be selected from a group consisting of two or more of the recited elements or components.

The use of the singular herein includes the plural (and vice versa) unless specifically stated otherwise. In addition, where the use of the term "about" is before a quantitative value, the present teachings also include the specific quantitative value itself, unless specifically stated otherwise.

It should be understood that the order of steps or order for performing certain actions is immaterial so long as the present teachings remain operable. Moreover, two or more steps or actions can be conducted simultaneously As used herein, the term "halogen" shall mean chlorine, bromine, fluorine and iodine. The term "halo shall mean chloro, bromo, fluoro and iodo.

As used herein, unless otherwise noted, "alkyl" and/or "aliphatic" whether used alone or as part of a substituent group refers to straight and branched carbon chains having 1 to 20 carbon atoms or any number within this range, for example 1 to 6 carbon atoms or 1 to 4 carbon atoms. Designated numbers of carbon atoms (e.g. $C_{1-6}$) shall refer independently to the number of carbon atoms in an alkyl moiety or to the alkyl portion of a larger alkyl-containing substituent. Non-limiting examples of alkyl groups include methyl, ethyl, n-propyl, No-propyl, n-butyl, sec-butyl, No-butyl, tert-butyl, and the like. Alkyl groups can be optionally substituted. Non-limiting examples of substituted alkyl groups include hydroxymethyl, chloromethyl, trifluoromethyl, aminomethyl, 1-chloroethyl, 2-hydroxyethyl, 1,2-difluoroethyl, 3-carboxypropyl, and the like. In substituent groups with multiple alkyl groups such as ($C_{1-6}$ alkyl)$_2$amino, the alkyl groups may be the same or different.

As used herein, the terms "alkenyl" and "alkynyl" groups, whether used alone or as part of a substituent group, refer to straight and branched carbon chains having 2 or more carbon atoms, preferably 2 to 20, wherein an alkenyl chain has at least one double bond in the chain and an alkynyl chain has at least one triple bond in the chain. Alkenyl and alkynyl groups can be optionally substituted. Nonlimiting examples of alkenyl groups include ethenyl, 3-propenyl, 1-propenyl (also 2-methylethenyl), isopropenyl (also 2-methylethen-2-yl), buten-4-yl, and the like. Nonlimiting examples of substituted alkenyl groups include 2-chloroethenyl (also 2-chlorovinyl), 4-hydroxybuten-1-yl, 7-hydroxy-7-methyloct-4-en-2-yl, 7-hydroxy-7-methyloct-3,5-dien-2-yl, and the like. Nonlimiting examples of alkynyl groups include ethynyl, prop-2-ynyl (also propargyl), propyn-1-yl, and 2-methyl-hex-4-yn-1-yl. Nonlimiting examples of substituted alkynyl groups include, 5-hydroxy-5-methylhex-3-ynyl, 6-hydroxy-6-methylhept-3-yn-2-yl, 5-hydroxy-5-ethylhept-3-ynyl, and the like.

As used herein, "cycloalkyl," whether used alone or as part of another group, refers to a non-aromatic carbon-containing ring including cyclized alkyl, alkenyl, and alkynyl groups, e.g., having from 3 to 14 ring carbon atoms, preferably from 3 to 7 or 3 to 6 ring carbon atoms, or even 3 to 4 ring carbon atoms, and optionally containing one or more (e.g., 1, 2, or 3) double or triple bond. Cycloalkyl groups can be monocyclic (e.g., cyclohexyl) or polycyclic (e.g., containing fused, bridged, and/or spiro ring systems), wherein the carbon atoms are located inside or outside of the ring system. Any suitable ring position of the cycloalkyl group can be covalently linked to the defined chemical structure. Cycloalkyl rings can be optionally substituted. Nonlimiting examples of cycloalkyl groups include: cyclopropyl, 2-methyl-cyclopropyl, cyclopropenyl, cyclobutyl, 2,3-dihydroxycyclobutyl, cyclobutenyl, cyclopentyl, cyclopentenyl, cyclopentadienyl, cyclohexyl, cyclohexenyl, cycloheptyl, cyclooctanyl, decalinyl, 2,5-dimethylcyclopentyl, 3,5-dichlorocyclohexyl, 4-hydroxycyclohexyl, 3,3,5-trimethylcyclohex-1-yl, octahydropentalenyl, octahydro-1H-indenyl, 3a,4,5,6,7,7a-hexahydro-3H-inden-4-yl, decahydroazulenyl; bicyclo[6.2.0]decanyl, decahydronaphthalenyl, and dodecahydro-1H-fluorenyl. The term "cycloalkyl" also includes carbocyclic rings which are bicyclic hydrocarbon rings, non-limiting examples of which include, bicyclo-[2.1.1]hexanyl, bicyclo[2.2.1]heptanyl, bicyclo[3.1.1]heptanyl, 1,3-dimethyl[2.2.1]heptan-2-yl, bicyclo[2.2.2]octanyl, and bicyclo[3.3.3]undecanyl.

"Haloalkyl" is intended to include both branched and straight-chain saturated aliphatic hydrocarbon groups having the specified number of carbon atoms, substituted with 1 or more halogen. Haloalkyl groups include perhaloalkyl groups, wherein all hydrogens of an alkyl group have been replaced with halogens (e.g., —$CF_3$, —$CF_2CF_3$). Haloalkyl groups can optionally be substituted with one or more substituents in addition to halogen. Examples of haloalkyl groups include, but are not limited to, fluoromethyl, dichloroethyl, trifluoromethyl, trichloromethyl, pentafluoroethyl, and pentachloroethyl groups.

The term "alkoxy" refers to the group —O-alkyl, wherein the alkyl group is as defined above. Alkoxy groups optionally may be substituted. The term $C_3$-$C_6$ cyclic alkoxy refers to a ring containing 3 to 6 carbon atoms and at least one oxygen atom (e.g., tetrahydrofuran, tetrahydro-2H-pyran). $C_3$-$C_6$ cyclic alkoxy groups optionally may be substituted.

The term "aryl," wherein used alone or as part of another group, is defined herein as a an unsaturated, aromatic monocyclic ring of 6 carbon members or to an unsaturated, aromatic polycyclic ring of from 10 to 14 carbon members. Aryl rings can be, for example, phenyl or naphthyl ring each optionally substituted with one or more moieties capable of replacing one or more hydrogen atoms. Non-limiting examples of aryl groups include: phenyl, naphthylen-1-yl, naphthylen-2-yl, 4-fluorophenyl, 2-hydroxyphenyl, 3-methylphenyl, 2-amino-4-fluorophenyl, 2-(N,N-diethylamino) phenyl, 2-cyanophenyl, 2,6-di-tert-butylphenyl, 3-methoxyphenyl, 8-hydroxynaphthylen-2-yl 4,5-dimethoxynaphthylen-1-yl, and 6-cyano-naphthylen-1-yl. Aryl groups also include, for example, phenyl or naphthyl rings fused with one or more saturated or partially saturated carbon rings (e.g., bicyclo[4.2.0]octa-1,3,5-trienyl, indanyl), which can be substituted at one or more carbon atoms of the aromatic and/or saturated or partially saturated rings.

The term "arylalkyl" or "aralkyl" refers to the group-alkyl-aryl, where the alkyl and aryl groups are as defined herein. Aralkyl groups of the present invention are optionally substituted. Examples of arylalkyl groups include, for example, benzyl (abbreviated as "Bn"), 1-phenylethyl, 2-phenylethyl, 3-phenylpropyl, 2-phenylpropyl, fluorenylmethyl and the like.

The terms "heterocyclic", "heterocycle", "heterocyclyl," whether used alone or as part of another group, are defined herein as one or more ring having from 3 to 20 atoms wherein at least one atom in at least one ring is a heteroatom selected from nitrogen (N), oxygen (O), or sulfur (S), and wherein further the ring that includes the heteroatom is non-aromatic. In heterocycle groups that include 2 or more fused rings, the non-heteroatom bearing ring may be aryl (e.g., indolinyl, tetrahydroquinolinyl, chromanyl). Exemplary heterocycle groups have from 3 to 14 ring atoms of which from 1 to 5 are heteroatoms independently selected from nitrogen (N), oxygen (O), or sulfur (S). One or more N or S atoms in a heterocycle group can be oxidized. Heterocycle groups can be optionally substituted.

Non-limiting examples of heterocyclic units having a single ring include: diazirinyl, aziridinyl, urazolyl, azetidinyl, pyrazolidinyl, imidazolidinyl, oxazolidinyl, isoxazolinyl, isoxazolyl, thiazolidinyl, isothiazolyl, isothiazolinyl oxathiazolidinonyl, oxazolidinonyl, hydantoinyl, tetrahydrofuranyl, pyrrolidinyl, morpholinyl, piperazinyl, piperidinyl, dihydropyranyl, tetrahydropyranyl, piperidin-2-onyl (valerolactam), 2,3,4,5-tetrahydro-1H-azepinyl, 2,3-dihydro-1H-indole, and 1,2,3,4-tetrahydro-quinoline. Non-limiting examples of heterocyclic units having 2 or more rings include: hexahydro-1H-pyrrolizinyl, 3a,4,5,6,7,7a-hexahydro-1H-benzo[d]imidazolyl, 3a,4,5,6,7,7a-hexahydro-1H-indolyl, 1,2,3,4-tetrahydroquinolinyl, chromanyl, isochromanyl, indolinyl, isoindolinyl, and decahydro-1H-cycloocta[b]pyrrolyl.

The term "heteroaryl," whether used alone or as part of another group, is defined herein as one or more rings having from 5 to 20 atoms wherein at least one atom in at least one ring is a heteroatom chosen from nitrogen (N), oxygen (O), or sulfur (S), and wherein further at least one of the rings that includes a heteroatom is aromatic. In heteroaryl groups that include 2 or more fused rings, the non-heteroatom bearing ring may be a carbocycle (e.g., 6,7-Dihydro-5H-cyclopentapyrimidine) or aryl (e.g., benzofuranyl, benzothiophenyl, indolyl). Exemplary heteroaryl groups have from 5 to 14 ring atoms and contain from 1 to 5 ring heteroatoms independently selected from nitrogen (N), oxygen (O), or sulfur (S). One or more N or S atoms in a heteroaryl group can be oxidized. Heteroaryl groups can be substituted. Non-limiting examples of heteroaryl rings containing a single ring include: 1,2,3,4-tetrazolyl, [1,2,3]triazolyl, [1,2,4]triazolyl, triazinyl, thiazolyl, 1H-imidazolyl, oxazolyl, furanyl, thiophenyl, pyrimidinyl, 2-phenylpyrimidinyl, pyridinyl, 3-methylpyridinyl, and 4-dimethylaminopyridinyl. Non-limiting examples of heteroaryl rings containing 2 or more fused rings include: benzofuranyl, benzothiophenyl, benzoxazolyl, benzthiazolyl, benztriazolyl, cinnolinyl, naphthyridinyl, phenanthridinyl, 7H-purinyl, 9H-purinyl, 6-amino-9H-purinyl, 5H-pyrrolo[3,2-ii]pyrimidinyl, 7H-pyrrolo[2,3-d]pyrimidinyl, pyrido[2,3-d]pyrimidinyl, 2-phenylbenzo[d]thiazolyl, 1H-indolyl, 4,5,6,7-tetrahydro-1-H-indolyl, quinoxalinyl, 5-methylquinoxalinyl, quinazolinyl, quinolinyl, 8-hydroxy-quinolinyl, and isoquinolinyl.

One non-limiting example of a heteroaryl group as described above is $C_1$-$C_5$ heteroaryl, which has 1 to 5 carbon ring atoms and at least one additional ring atom that is a heteroatom (preferably 1 to 4 additional ring atoms that are heteroatoms) independently selected from nitrogen (N), oxygen (O), or sulfur (S). Examples of $C_1$-$C_5$ heteroaryl include, but are not limited to, triazinyl, thiazol-2-yl, thiazol-4-yl, imidazol-1-yl, 1H-imidazol-2-yl, 1H-imidazol-4-yl, isoxazolin-5-yl, furan-2-yl, furan-3-yl, thiophen-2-yl, thiophen-4-yl, pyrimidin-2-yl, pyrimidin-4-yl, pyrimidin-5-yl, pyridin-2-yl, pyridin-3-yl, and pyridin-4-yl.

Unless otherwise noted, when two substituents are taken together to form a ring having a specified number of ring atoms (e.g., $R^2$ and $R^3$ taken together with the nitrogen (N) to which they are attached to form a ring having from 3 to 7 ring members), the ring can have carbon atoms and optionally one or more (e.g., 1 to 3) additional heteroatoms independently selected from nitrogen (N), oxygen (O), or sulfur (S). The ring can be saturated or partially saturated and can be optionally substituted.

For the purposed of the present invention fused ring units, as well as spirocyclic rings, bicyclic rings and the like, which comprise a single heteroatom will be considered to belong to the cyclic family corresponding to the heteroatom containing ring. For example, 1,2,3,4-tetrahydroquinoline having the formula:

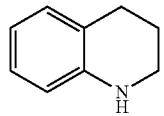

is, for the purposes of the present invention, considered a heterocyclic unit. 6,7-Dihydro-5H-cyclopentapyrimidine having the formula:

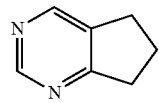

is, for the purposes of the present invention, considered a heteroaryl unit. When a fused ring unit contains heteroatoms in both a saturated and an aryl ring, the aryl ring will predominate and determine the type of category to which the ring is assigned. For example, 1,2,3,4-tetrahydro-[1,8]naphthyridine having the formula:

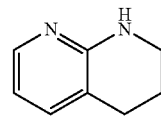

is, for the purposes of the present invention, considered a heteroaryl unit.

Whenever a term or either of their prefix roots appear in a name of a substituent the name is to be interpreted as including those limitations provided herein. For example, whenever the term "alkyl" or "aryl" or either of their prefix roots appear in a name of a substituent (e.g., arylalkyl, alkylamino) the name is to be interpreted as including those limitations given above for "alkyl" and "aryl."

The term "substituted" is used throughout the specification. The term "substituted" is defined herein as a moiety, whether acyclic or cyclic, which has one or more hydrogen atoms replaced by a substituent or several (e.g., 1 to 10) substituents as defined herein below. The substituents are capable of replacing one or two hydrogen atoms of a single moiety at a time. In addition, these substituents can replace two hydrogen atoms on two adjacent carbons to form said substituent, new moiety or unit. For example, a substituted unit that requires a single hydrogen atom replacement includes halogen, hydroxyl, and the like. A two hydrogen atom replacement includes carbonyl, oximino, and the like. A two hydrogen atom replacement from adjacent carbon atoms includes epoxy, and the like. The term "substituted" is used throughout the present specification to indicate that a moiety can have one or more of the hydrogen atoms replaced by a substituent. When a moiety is described as "substituted" any number of the hydrogen atoms may be replaced. For example, difluoromethyl is a substituted $C_1$ alkyl; trifluoromethyl is a substituted $C_1$ alkyl; 4-hydroxyphenyl is a substituted aromatic ring; (N,N-dimethyl-5-amino)octanyl is a substituted $C_8$ alkyl; 3-guanidinopropyl is a substituted $C_3$ alkyl; and 2-carboxypyridinyl is a substituted heteroaryl.

The variable groups defined herein, e.g., alkyl, alkenyl, alkynyl, cycloalkyl, alkoxy, aryloxy, aryl, heterocycle and heteroaryl groups defined herein, whether used alone or as part of another group, can be optionally substituted. Optionally substituted groups will be so indicated.

The following are non-limiting examples of substituents which can substitute for hydrogen atoms on a moiety: halogen (chlorine (Cl), bromine (Br), fluorine (F) and iodine (I)), —CN, —$NO_2$, oxo (=O), —$OR^{12}$, —$SR^{12}$, —$N(R^{12})_2$, —$NR^{12}C(O)R^{12}$, —$SO_2R^{12}$, —$SO_2OR^{12}$, —$SO_2N(R^{12})_2$, —$C(O)R^{12}$, —$C(O)OR^{12}$, —$C(O)N(R^{12})_2$, $C_{1-6}$ alkyl, $C_{1-6}$ haloalkyl, $C_{1-6}$ alkoxy, $C_{2-8}$ alkenyl, $C_{2-8}$ alkynyl, $C_{3-14}$ cycloalkyl, aryl, heterocycle, or heteroaryl, wherein each of the alkyl, haloalkyl, alkenyl, alkynyl, alkoxy, cycloalkyl, aryl, heterocycle, and heteroaryl groups is optionally substituted with 1-10 (e.g., 1-6 or 1-4) groups selected independently from halogen, —CN, —$NO_2$, oxo, and $R^{12}$; wherein $R^{12}$, independently is hydrogen, —$OR^{13}$, —$SR^{13}$, —$C(O)R^{13}$, —$C(O)OR^{13}$, —$C(O)N(R^{13})_2$, —$SO_2R^{13}$, —$S(O)_2OR^{13}$, —$N(R^{13})_2$, —$NR^{13}C(O)R^{13}$, $C_{1-6}$ alkyl, $C_{1-6}$ haloalkyl, $C_{2-8}$ alkenyl, $C_{2-8}$ alkynyl, cycloalkyl (e.g., $C_{3-6}$ cycloalkyl), aryl, heterocycle, or heteroaryl, or two $R^{12}$ units taken together with the atom(s) to which they are bound form an optionally substituted carbocycle or heterocycle wherein said carbocycle or heterocycle has 3 to 7 ring atoms; wherein $R^{13}$, independently is hydrogen, $C_{1-6}$ alkyl, $C_{1-6}$ haloalkyl, $C_{2-8}$ alkenyl, $C_{2-8}$ alkynyl, cycloalkyl (e.g., $C_{3-6}$ cycloalkyl), aryl, heterocycle, or heteroaryl, or two $R^{13}$ units taken together with the atom(s) to which they are bound form an optionally substituted carbocycle or heterocycle wherein said carbocycle or heterocycle preferably has 3 to 7 ring atoms.

In some embodiments, the substituents are selected from
i) —$OR^{14}$; for example, —OH, —$OCH_3$, —$OCH_2CH_3$, —$OCH_2CH_2CH_3$;
ii) —$C(O)R^{14}$; for example, —$COCH_3$, —$COCH_2CH_3$, —$COCH_2CH_2CH_3$;
iii) —$C(O)OR^{14}$; for example, —$CO_2CH_3$, —$CO_2CH_2CH_3$, —$CO_2CH_2CH_2CH_3$;
iv) —$C(O)N(R^{14})_2$; for example, —$CONH_2$, —$CONHCH_3$, —$CON(CH_3)_2$;
v) —$N(R^{14})_2$; for example, —$NH_2$, —$NHCH_3$, —$N(CH_3)_2$, —$NH(CH_2CH_3)$;
vi) halogen: —F, —Cl, —Br, and —I;
vii) —$CH_eX_g$; wherein X is halogen, m is from 0 to 2, e+g=3; for example, —$CH_2F$, —$CHF_2$, —$CF_3$, —$CCl_3$, or —$CBr_3$;
viii) —$SO_2R^{14}$; for example, —$SO_2H$; —$SO_2CH_3$; —$SO_2C_6H_5$;
ix) $C_1$-$C_6$ linear, branched, or cyclic alkyl;
x) Cyano
xi) Nitro;
xii) $N(R^{14})C(O)R^{14}$;
xiii) Oxo (=O);
xiv) Heterocycle; and
xv) Heteroaryl.
wherein each $R^{14}$ is independently hydrogen, optionally substituted $C_1$-$C_6$ linear or branched alkyl (e.g., optionally substituted $C_1$-$C_4$ linear or branched alkyl), or optionally substituted $C_3$-$C_6$ cycloalkyl (e.g optionally substituted $C_3$-$C_4$ cycloalkyl); or two $R^{14}$ units can be taken together to form a ring comprising 3-7 ring atoms. In certain aspects, each $R^{14}$ is independently hydrogen, $C_1$-$C_6$ linear or branched alkyl optionally substituted with halogen or $C_3$-$C_6$ cycloalkyl or $C_3$-$C_6$ cycloalkyl.

At various places in the present specification, substituents of compounds are disclosed in groups or in ranges. It is specifically intended that the description include each and every individual subcombination of the members of such groups and ranges. For example, the term "$C_{1-6}$ alkyl" is specifically intended to individually disclose $C_1$, $C_2$, $C_3$, $C_4$, $C_5$, $C_6$, $C_1$-$C_6$, $C_1$-$C_5$, $C_1$-$C_4$, $C_1$-$C_3$, $C_1$-$C_2$, $C_2$-$C_6$, $C_2$-$C_5$, $C_2$-$C_4$, $C_2$-$C_3$, $C_3$-$C_6$, $C_3$-$C_5$, $C_3$-$C_4$, $C_4$-$C_6$, $C_4$-$C_5$, and $C_5$-$C_6$, alkyl.

For the purposes of the present invention the terms "compound," "analog," and "composition of matter" stand equally well for the inhibitors of tau oligomer formation described herein, including all enantiomeric forms, diastereomeric forms, salts, and the like, and the terms "compound," "analog," and "composition of matter" are used interchangeably throughout the present specification.

Compounds described herein can contain an asymmetric atom (also referred as a chiral center), and some of the compounds can contain one or more asymmetric atoms or centers, which can thus give rise to optical isomers (enantiomers) and diastereomers. The present teachings and compounds disclosed herein include such enantiomers and diastereomers, as well as the racemic and resolved, enantiomerically pure R and S stereoisomers, as well as other mixtures of the R and S stereoisomers and pharmaceutically acceptable salts thereof. Optical isomers can be obtained in pure form by standard procedures known to those skilled in the art, which include, but are not limited to, diastereomeric salt formation, kinetic resolution, and asymmetric synthesis. The present teachings also encompass cis and trans isomers of compounds containing alkenyl moieties (e.g., alkenes and imines). It is also understood that the present teachings encompass all possible regioisomers, and mixtures thereof, which can be obtained in pure form by standard separation procedures known to those skilled in the art, and include, but are not limited to, column chromatography, thin-layer chromatography, and high-performance liquid chromatography. Where the compounds described herein contains, for example, a keto or oxime group or an aromatic moiety, tautomeric isomerism ('tautomerism') can occur. It follows that a single compound may exhibit more than one type of isomerism.

Included within the scope of the compounds of the disclosure are all stereoisomers, geometric isomers and tautomeric forms of the compounds of the disclosure including compounds exhibiting more than one type of isomerism, and mixtures of one or more thereof. Also included are acid addition or base salts wherein the counterion is optically active, for example, D-lactate or L-lysine, or racemic, for example, DL-tartrate or DL-arginine.

Pharmaceutically acceptable salts of compounds of the present teachings, which can have an acidic moiety, can be formed using organic and inorganic bases. Both mono and polyanionic salts are contemplated, depending on the number of acidic hydrogens available for deprotonation. Suitable salts formed with bases include metal salts, such as alkali metal or alkaline earth metal salts, for example sodium, potassium, or magnesium salts; ammonia salts and organic amine salts, such as those formed with morpholine, thiomorpholine, piperidine, pyrrolidine, a mono-, di- or tri-lower alkylamine (e.g., ethyl-tert-butyl-, diethyl-, diisopropyl-, triethyl-, tributyl- or dimethylpropylamine), or a mono-, di-, or trihydroxy lower alkylamine (e.g., mono-, di- or triethanolamine). Specific non-limiting examples of inorganic bases include $NaHCO_3$, $Na_2CO_3$, $KHCO_3$, $K_2CO_3$, $Cs_2CO_3$, LiOH, NaOH, KOH, $NaH_2PO_4$, $Na_2HPO_4$, and $Na_3PO_4$. Internal salts also can be formed. Similarly, when a compound disclosed herein contains a basic moiety, salts can be formed using organic and inorganic acids. For example, salts can be formed from the following acids: acetic, aspartic, boric, glucoheptonic, glucuronic, hexafluorophosphoric, 2-(4-hydroxybenzoyl)benzoic, hydroiodic, ethanedisulfonic, isethionic, nicotinic, orotic, palmitic, saccharic, stearic, trifluoroacetic, propionic, lactic, benzenesulfonic, benzoic, camphorsulfonic, citric, tartaric, succinic, dichloroacetic, ethenesulfonic, formic, fumaric, gluconic, glutamic, hippuric, hydrobromic, hydrochloric, isethionic, lactic, maleic, malic, malonic, mandelic, methanesulfonic, mucic, napthalenesulfonic, nitric, oxalic, pamoic, pantothenic, phosphoric, phthalic, propionic, succinic, sulfuric, tartaric, toluenesulfonic, and camphorsulfonic as well as other known pharmaceutically acceptable acids. Additional suitable base salts are formed from bases which form pharmaceutically acceptable salts. Examples include the aluminium, arginine, benzathine, calcium, choline, diethylamine, diolamine, glycine, lysine, magnesium, meglumine, olamine, potassium, sodium, tromethamine and zinc salts. For a review on suitable salts, see "Handbook of Pharmaceutical Salts: Properties, Selection, and Use" by Stahl and Wermuth (Wiley-VCH, Weinheim, Germany, 2002).

A pharmaceutically acceptable salt of a compound of formula (I) may be readily prepared by mixing together solutions of the compound of formula (I) and the desired acid or base, as appropriate. The salt may precipitate from solution and be collected by filtration or may be recovered by evaporation of the solvent. The degree of ionisation in the salt may vary from completely ionised to almost non-ionised.

The compounds of the invention may exist in both unsolvated and solvated forms. The term 'solvate' is used herein to describe a molecular complex comprising the compound of the invention and one or more pharmaceutically acceptable solvent molecules, for example, ethanol. The term 'hydrate' is employed when said solvent is water. Pharmaceutically acceptable solvates include hydrates and other solvates wherein the solvent of crystallization may be isotopically substituted, e.g. $D_2O$, $d_6$-acetone, $d_6$-DMSO. The compounds of the present invention (including, those in the form of salts, free bases, free acids and neutral compounds) may form hydrates and other solvates.

The compounds of the present invention may exist as clathrates or other complexes, such as drug-host inclusion complexes wherein, in contrast to the aforementioned solvates, the drug and host are present in stoichiometric or non-stoichiometric amounts. The compounds may also exist as complexes of the drug containing two or more organic and/or inorganic components which may be in stoichiometric or non-stoichiometric amounts. The resulting complexes may be ionised, partially ionised, or non-ionised. For a review of such complexes, see J Pharm Sci, 64 (8), 1269-1288 by Haleblian (August 1975). The compounds of the of the present invention may also exist as polymorphs and isomers thereof (including optical, geometric and tautomeric isomers) and isotopically-labelled compounds. In the solid state, the compounds of the present invention may exist in crystalline or amorphous form.

The compounds of the present invention may be administered as prodrugs. Thus certain derivatives of compounds of the disclosure which may have little or no pharmacological activity themselves can, when administered into or onto the body, be converted into compounds having the desired activity, for example, by hydrolytic cleavage. Such derivatives are referred to as 'prodrugs'. Further information on the use of prodrugs may be found in 'Pro-drugs as Novel Delivery Systems, Vol. 14, ACS Symposium Series (T Higuchi and W Stella) and 'Bioreversible Carriers in Drug Design', Pergamon Press, 1987 (ed. E B Roche, American Pharmaceutical Association).] Prodrugs can, for example, be produced by replacing appropriate functionalities present in the compounds of the disclosure with certain moieties known to those skilled in the art as 'pro-moieties' as described, for example, in "Design of Prodrugs" by H Bundgaard (Elsevier, 1985). Some examples of such prodrugs include:

(i) where the compound of formula (I) contains a carboxylic acid functionality (—COOH), an ester thereof, for example, replacement of the hydrogen with ($C_1$-$C_8$) alkyl;

(ii) where the compound of formula (I) contains an alcohol functionality (—OH), an ether thereof, for example, replacement of the hydrogen with ($C_1$-C6) alkanoyloxymethyl; and (iii) where the compound of formula (I) contains a primary or secondary amino functionality (—$NH_2$ or —NHR where R≠H), an amide thereof, for example, replacement of one or both hydrogens with ($C_1$-$C_{10}$) alkanoyl. [Further examples of replacement groups in accordance with the foregoing examples and examples of other prodrug types may be found in the aforementioned references.] Finally, certain compounds of the disclosure may themselves act as prodrugs of other compounds of the disclosure respectively.

The present invention includes all pharmaceutically acceptable isotopically-labelled compounds of the disclosure wherein one or more atoms are replaced by atoms having the same atomic number, but an atomic mass or mass number different from the atomic mass or mass number usually found in nature.

Examples of isotopes suitable for inclusion in the compounds of the invention include isotopes of hydrogen, such as $^2H$ and $^3H$, carbon, such as $^{11}C$, $^{13}C$ and $^{14}C$, chlorine, such as $^{36}Cl$, fluorine, such as $^{18}F$, iodine, such as $^{123}I$ and $^{125}I$, nitrogen, such as $^{13}N$ and $^{15}N$, oxygen, such as $^{15}O$, $^{17}O$ and $^{18}O$, phosphorus, such as $^{32}P$, and sulphur, such as $^{35}S$.

Certain isotopically-labelled compounds of the disclosure, for example, those incorporating a radioactive isotope, are useful in drug and/or substrate tissue distribution studies. The radioactive isotopes tritium, i.e. $^3H$, and carbon-14, i.e. $^{14}C$, are particularly useful for this purpose in view of their ease of incorporation and ready means of detection.

Substitution with heavier isotopes such as deuterium, i.e. $^2H$, may afford certain therapeutic advantages resulting from greater metabolic stability, for example, increased in vivo half-life or reduced dosage requirements, and hence may be preferred in some circumstances.

Substitution with positron emitting isotopes, such as $^{11}C$, $^{18}F$, $^{15}O$ and $^{13}N$, can be useful in Positron Emission Tomography (PET) studies for examining substrate receptor occupancy and as diagnostic agents in patients and animals.

Isotopically-labelled compounds of the disclosure can generally be prepared by conventional techniques known to those skilled in the art or by processes analogous to those described in the accompanying Examples and Preparations using an appropriate isotopically-labelled reagents in place of the non-labelled reagent previously employed.

When any variable occurs more than one time in any constituent or in any formula, its definition in each occurrence is independent of its definition at every other occurrence (e.g., in $N(R^x)_2$, each $R^x$ may be the same or different than the other). Combinations of substituents and/or variables are permissible only if such combinations result in stable compounds.

The terms "treat" and "treating" and "treatment" as used herein, refer to partially or completely alleviating, inhibiting, ameliorating and/or relieving or preventing a condition from which a patient is suspected to suffer.

As used herein, "therapeutically effective" and "effective dose" refer to a substance or an amount that elicits a desirable biological activity or effect.

Except when noted, the terms "subject" or "patient" are used interchangeably and refer to mammals such as human patients and non-human primates, as well as experimental animals such as rabbits, rats, and mice, and other animals. Accordingly, the term "subject" or "patient" as used herein means any mammalian patient or subject to which the compounds of the invention can be administered. In an exemplary embodiment of the present invention, to identify subject patients for treatment according to the methods of the invention, accepted screening methods are employed to determine risk factors associated with a targeted or suspected disease or condition or to determine the status of an existing disease or condition in a subject. These screening methods include, for example, conventional work-ups to determine risk factors that may be associated with the targeted or suspected disease or condition. These and other routine methods allow the clinician to select patients in need of therapy using the methods and compounds of the present invention.

An embodiment of the invention includes compounds having formula (XIX):

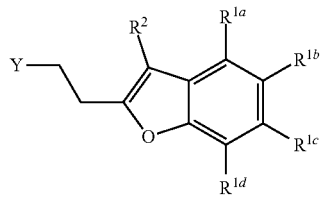

(XIX)

including enantiomers, diastereomers, hydrates, solvates, pharmaceutically acceptable salts, and complexes thereof, wherein $R^{1a}$ and $R^{1d}$ are each independently selected from the group consisting of hydrogen, halogen, $C_{1-6}$ alkyl, $C_{1-6}$ alkoxy, $C_{1-6}$ haloalkyl, and $C_{1-6}$ haloalkoxy;
$R^{1b}$ and $R^{1c}$ are selected from the group consisting of hydrogen, halogen, optionally substituted aryl and optionally substituted heteroaryl;
When $R^{1b}$ is hydrogen, $R^{1c}$ is not hydrogen;
When $R^{1c}$ is hydrogen, $R^{1b}$ is not hydrogen;
$R^2$ is selected from the group consisting of $C_{1-6}$ alkyl, $C_{3-7}$ branched alkyl, $C_{1-6}$ alkylaryl, optionally substituted aryl and optionally substituted heteroaryl;
X is selected from the group consisting of oxygen, sulfur, NH, and $NR^5$;
Wherein $R^5$ is $C_{1-6}$ alkyl;
Y is selected from the group consisting of

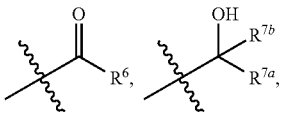

and optionally substituted 2-benzimidazole;
Wherein $R^6$ is selected from the group consisting of hydrogen, OH, $OR^{7c}$, optionally substituted $C_{1-6}$ alkyl, $NR^{3a}R^{3b}$, optionally substituted aryl, and optionally substituted heteroaryl;
$R^{3a}$ and $R^{3b}$ are independently selected from the group consisting of hydrogen and $C_{1-6}$ alkyl;
$R^{3a}$ and $R^{3b}$ are taken together with the atom to which they are bound to form a three to six membered saturated ring optionally substituted with a group selected from OH, $C_{1-6}$ alkyl, $NR^{8a}R^{8b}$ optionally including a member selected from the group consisting of O, $NR^8$, and S;
$R^8$ is selected from the group consisting of hydrogen, $C_{1-6}$ alkyl, and CO ($C_{1-6}$alkyl;
$R^{8a}$ and $R^{8b}$ are at each occurrence independently selected from of hydrogen and $C_{1-6}$ alkyl.
$R^{7a}$ is selected from the group consisting of hydrogen and $C_{1-6}$ alkyl;
$R^{7b}$ is selected from the group consisting of $C_{1-6}$ alkyl, aryl, and heteroaryl; and $R^{7c}$ is selected from the group consisting of $C_{1-6}$ alkyl and $C_{3-7}$ branched alkyl.

Another embodiment of the invention includes compounds having formula (XX):

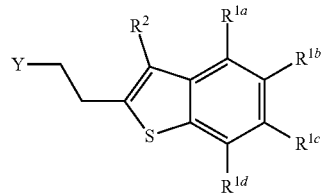

(XX)

including enantiomers, diastereomers, hydrates, solvates, pharmaceutically acceptable salts, and complexes thereof, wherein $R^{1a}$, $R^{1b}$, $R^{1c}$, $R^{1d}$, $R^2$, and Y are as defined for formula XIX;

Another embodiment of the invention includes compounds having formula (XXI):

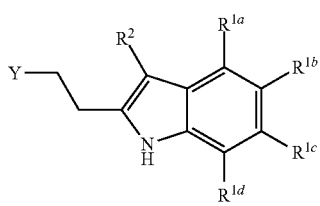

(XXI)

including enantiomers, diastereomers, hydrates, solvates, pharmaceutically acceptable salts, and complexes thereof, wherein $R^{1a}$, $R^{1b}$, $R^{1c}$, $R^{1d}$, $R^2$, and Y are as defined for formula XIX; compounds having formula (XXII):

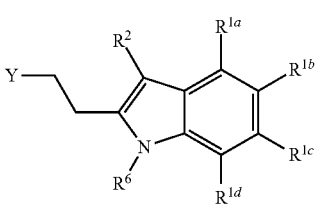

(XXII)

including enantiomers, diastereomers, hydrates, solvates, pharmaceutically acceptable salts, and complexes thereof, wherein $R^{1a}$, $R^{1b}$, $R^{1c}$, $R^{1d}$, $R^2$, $R^5$ and Y are as defined for formula XIX.

Another embodiment of the invention includes compounds having formula (XXIII):

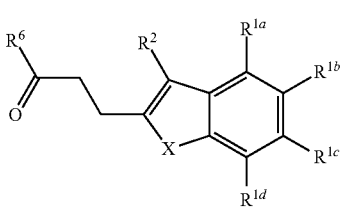

(XXIII)

including enantiomers, diastereomers, hydrates, solvates, pharmaceutically acceptable salts, and complexes thereof, wherein $R^{1a}$, $R^{1b}$, $R^{1c}$, $R^{1d}$, $R^2$, $R^6$, and X are as defined for formula XIX.

Another embodiment of the invention includes compounds having formula (XXIV):

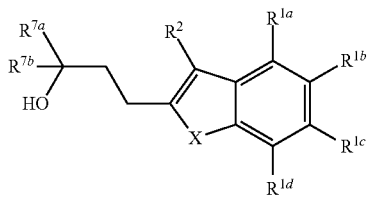

including enantiomers, diastereomers, hydrates, solvates, pharmaceutically acceptable salts, and complexes thereof, wherein $R^{1a}$, $R^{1b}$, $R^{1c}$, $R^{1d}$, $R^2$, $R^{7a}$, $R^{7b}$ and X are as defined for formula XIX.

Another embodiment of the invention includes compounds having formula (VII):

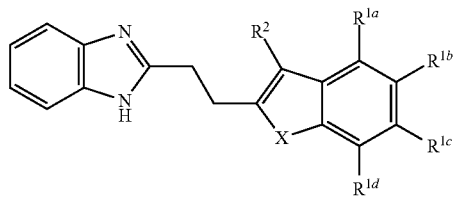

including enantiomers, diastereomers, hydrates, solvates, pharmaceutically acceptable salts, and complexes thereof, wherein $R^{1a}$, $R^{1b}$, $R^{1c}$, $R^{1d}$, $R^2$ and X are as defined for formula XIX.

Another embodiment of the invention includes compounds having formula (XXVI):

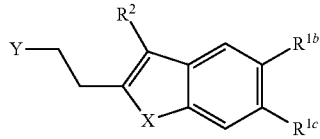

including enantiomers, diastereomers, hydrates, solvates, pharmaceutically acceptable salts, and complexes thereof, wherein $R^{1b}$, $R^{1c}$, $R^2$, X and Y are as defined for formula XIX.

Another embodiment of the invention includes compounds having formula (XXVII):

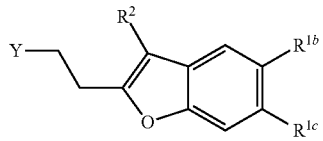

including enantiomers, diastereomers, hydrates, solvates, pharmaceutically acceptable salts, and complexes thereof, wherein $R^{1b}$, $R^{1c}$, $R^2$, and Y are as defined for formula I.

Another embodiment of the invention includes compounds having formula (XXVIII):

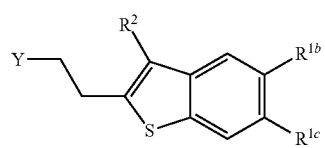

including enantiomers, diastereomers, hydrates, solvates, pharmaceutically acceptable salts, and complexes thereof, wherein $R^{1b}$, $R^{1c}$, $R^2$, and Y are as defined for formula XIX.

Another embodiment of the invention includes compounds having formula (XXIX):

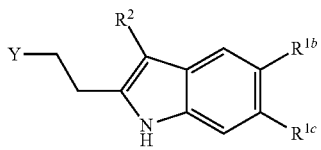

including enantiomers, diastereomers, hydrates, solvates, pharmaceutically acceptable salts, and complexes thereof, wherein $R^{1b}$, $R^{1c}$, $R^2$, and Y are as defined for formula XIX.

Another embodiment of the invention includes compounds having formula (XXX):

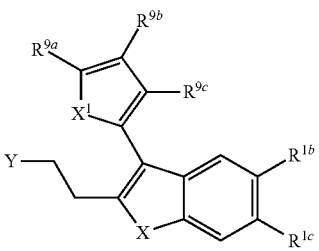

including enantiomers, diastereomers, hydrates, solvates, pharmaceutically acceptable salts, and complexes thereof, wherein $R^{1b}$, $R^{1c}$, X and Y are as defined for formula XIX; $R^{9a}$, $R^{9b}$, and $R^{9c}$ are independently selected from the group consisting of hydrogen, halogen, and $C_{1-6}$ alkyl; and $X^1$ is selected from the group consisting of oxygen and sulfur.

Another embodiment of the invention includes compounds having formula (XXXI):

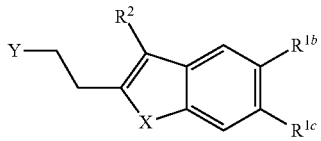

including enantiomers, diastereomers, hydrates, solvates, pharmaceutically acceptable salts, and complexes thereof, wherein $R^{1a}$ and $R^{1d}$ are each independently selected from the group consisting of hydrogen, halogen, $C_{1-6}$ alkyl, $C_{1-6}$ alkoxy, $C_{1-6}$ haloalkyl, and $C_{1-6}$ haloalkoxy;

$R^{1b}$ and $R^{1c}$ are selected from the group consisting of hydrogen, halogen, optionally substituted aryl and optionally substituted heteroaryl;

When $R^{1b}$ is hydrogen, $R^{1c}$ is not hydrogen;

When $R^{1c}$ is hydrogen, $R^{1b}$ is not hydrogen;

$R^2$ is selected from the group consisting of $C_{1-6}$ alkyl, $C_{3-7}$ branched alkyl, $C_{1-6}$ alkylaryl, optionally substituted aryl and optionally substituted heteroaryl;

X is selected from the group consisting of oxygen, sulfur, NH, and $NR^3$;

Wherein $R^5$ is $C_{1-6}$ alkyl;

Y is selected from the group consisting of

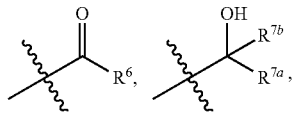

and optionally substituted 2-benzimidazole;

Wherein $R^6$ is selected from the group consisting of hydrogen, OH, $OR^{7c}$, optionally substituted $C_{1-6}$ alkyl, $NR^{3a}R^{3b}$, optionally substituted aryl, and optionally substituted heteroaryl;

$R^{3a}$ and $R^{3b}$ are independently selected from the group consisting of hydrogen and $C_{1-6}$ alkyl;

$R^{3a}$ and $R^{3b}$ are taken together with the atom to which they are bound to form an three to six membered saturated ring optionally substituted with a group selected from OH, $C_{1-6}$ alkyl, $NR^{8a}R^{8b}$ optionally including a member selected from the group consisting of O, $NR^8$, and S;

$R^8$ is selected from the group consisting of hydrogen, $C_{1-6}$ alkyl, and CO ($C_{1-6}$ alkyl;

$R^{8a}$ and $R^{8b}$ are independently selected from of hydrogen and $C_{1-6}$ alkyl.

$R^{7a}$ is selected from the group consisting of hydrogen and $C_{1-6}$ alkyl;

$R^{7b}$ is selected from the group consisting of $C_{1-6}$ alkyl, aryl, and heteroaryl;

and $R^{7C}$ is selected from the group consisting of $C_{1-6}$ alkyl and $C_{3-7}$ branched alkyl.

Another embodiment of the invention includes compounds having formula (XXXII):

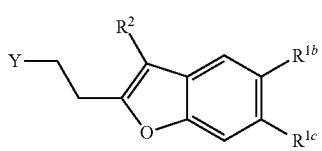

(XXXII)

including enantiomers, diastereomers, hydrates, solvates, pharmaceutically acceptable salts, and complexes thereof, wherein $R^{1b}$, $R^{1c}$, $R^2$, and Y are as defined for formula XXXI; compounds having formula (XXXIII):

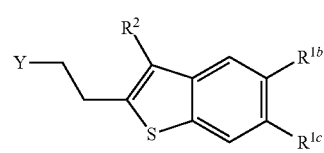

(XXXIII)

including enantiomers, diastereomers, hydrates, solvates, pharmaceutically acceptable salts, and complexes thereof, wherein $R^{1b}$, $R^{1c}$, $R^2$, and Y are as defined for formula XXXI.

Another embodiment of the invention includes compounds having formula (XXXIV):

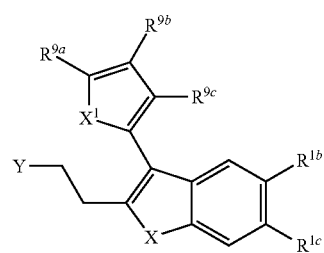

(XXXIV)

including enantiomers, diastereomers, hydrates, solvates, pharmaceutically acceptable salts, and complexes thereof, wherein $R^{1b}$, $R^{1c}$, X and Y are as defined for formula XXXI;

$R^{9a}$, $R^{9b}$, and $R^{9c}$ are independently selected from the group consisting of hydrogen, halogen, and $C_{1-6}$ alkyl;

and $X^1$ is selected from the group consisting of oxygen and sulfur.

Another embodiment of the invention includes compounds having formula (XXXV):

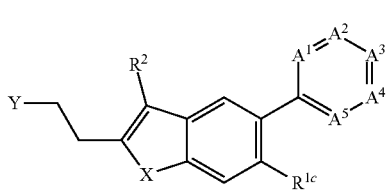

(XXXV)

including enantiomers, diastereomers, hydrates, solvates, pharmaceutically acceptable salts, and complexes thereof, wherein $R^{1c}$, $R^2$, X and Y are as defined for formula XXXI;

$A^1$, $A^2$, $A^3$, $A^4$, and $A^5$ are selected from the group consisting of nitrogen and $CR^{10}$;

No more than two of $A^1$, $A^2$, $A^3$, $A^4$, and $A^5$ may be nitrogen;

$R^{10}$ is selected from the group consisting of hydrogen, $C_{1-6}$ alkyl, $C_{1-6}$ haloalkyl, $C_{1-6}$ haloalkoxy, $C_{1-6}$ alkoxy, halogen, hydroxy, and $NHSO_2R^{11}$;

and $R^{11}$ is independently selected from the group consisting of hydrogen and $C_{1-6}$ alkyl.

Another embodiment of the invention includes compounds having formula (XXXVI):

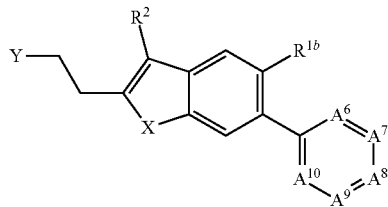

(XXXVI)

including enantiomers, diastereomers, hydrates, solvates, pharmaceutically acceptable salts, and complexes thereof, wherein $R^{1b}$, $R^2$, X and Y are as defined for formula XXXI;
$A^6$, $A^7$, $A^8$, $A^9$, and $A^{10}$ are selected from the group consisting of nitrogen and $CR^{10}$;
No more than two of $A^6$, $A^7$, $A^8$, $A^9$, and $A^{10}$ may be nitrogen;
$R^{10}$ is selected from the group consisting of hydrogen, $C_{1-6}$ alkyl, $C_{1-6}$ haloalkyl, $C_{1-6}$ haloalkoxy, $C_{1-6}$ alkoxy, halogen, hydroxy, and $NHSO_2R^{11}$;
and $R^{11}$ is independently selected from the group consisting of hydrogen and $C_{1-6}$ alkyl.

Another embodiment of the invention includes compounds having formula (XXXVII):

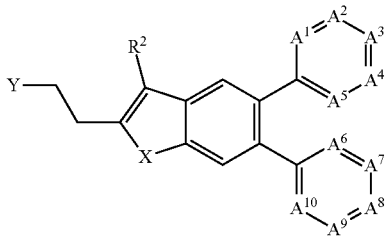

(XXXVII)

including enantiomers, diastereomers, hydrates, solvates, pharmaceutically acceptable salts, and complexes thereof, wherein $R^2$, X and Y are as defined for formula XXXI;
$A^1$, $A^2$, $A^3$, $A^4$, $A^5$, $A^6$, $A^7$, $A^8$, $A^9$, and $A^{10}$ are selected from the group consisting of nitrogen and $CR^{10}$;
No more than two of $A^1$, $A^2$, $A^3$, $A^4$, and $A^5$ may be nitrogen;
No more than two of $A^6$, $A^7$, $A^8$, $A^9$, and $A^{10}$ may be nitrogen;
$R^{10}$ is selected from the group consisting of hydrogen, $C_{1-6}$ alkyl, $C_{1-6}$ haloalkyl, $C_{1-6}$ haloalkoxy, $C_{1-6}$ alkoxy, halogen, hydroxy, and $NHSO_2R^{11}$;
and $R^{11}$ is independently selected from the group consisting of hydrogen and $C_{1-6}$ alkyl.

Another embodiment of the invention includes compounds having formula (XXXVIII):

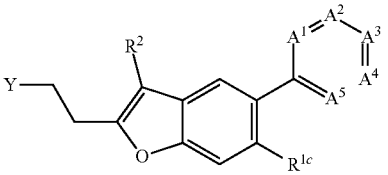

(XXXVIII)

including enantiomers, diastereomers, hydrates, solvates, pharmaceutically acceptable salts, and complexes thereof, wherein $R^{1c}$, $R^2$ and Y are as defined for formula XXXI;
$A^1$, $A^2$, $A^3$, $A^4$, and $A^5$ are selected from the group consisting of nitrogen and $CR^{10}$;
No more than two of $A^1$, $A^2$, $A^3$, $A^4$, and $A^5$ may be nitrogen;
$R^{10}$ is selected from the group consisting of hydrogen, $C_{1-6}$ alkyl, $C_{1-6}$ haloalkyl, $C_{1-6}$ haloalkoxy, $C_{1-6}$ alkoxy, halogen, hydroxy, and $NHSO_2R^{11}$;
and $R^{11}$ is independently selected from the group consisting of hydrogen and $C_{1-6}$ alkyl.

Another embodiment of the invention includes compounds having formula (XXXIX):

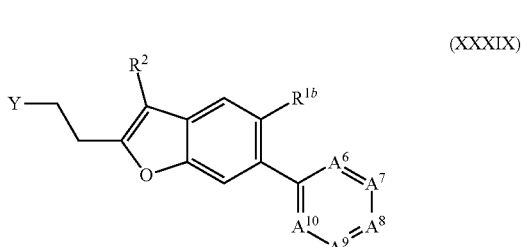

(XXXIX)

including enantiomers, diastereomers, hydrates, solvates, pharmaceutically acceptable salts, and complexes thereof, wherein $R^{1b}$, $R^2$ and Y are as defined for formula XXXI;
$A^6$, $A^7$, $A^8$, $A^9$, and $A^{10}$ are selected from the group consisting of nitrogen and $CR^{10}$;
No more than two of $A^6$, $A^7$, $A^8$, $A^9$, and $A^{10}$ may be nitrogen;
$R^{10}$ is selected from the group consisting of hydrogen, $C_{1-6}$ alkyl, $C_{1-6}$ haloalkyl, $C_{1-6}$ haloalkoxy, $C_{1-6}$ alkoxy, halogen, hydroxy, and $NHSO_2R^{11}$;
and $R^{11}$ is independently selected from the group consisting of hydrogen and $C_{1-6}$ alkyl.

Another embodiment of the invention includes compounds having formula (XL):

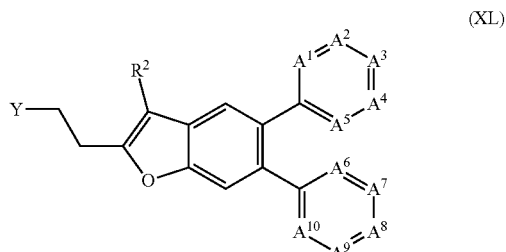

(XL)

including enantiomers, diastereomers, hydrates, solvates, pharmaceutically acceptable salts, and complexes thereof, wherein $R^2$ and Y are as defined for formula XXXI;
$A^1$, $A^2$, $A^3$, $A^4$, $A^5$, $A^6$, $A^7$, $A^8$, $A^9$, and $A^{10}$ are selected from the group consisting of nitrogen and $CR^{10}$;
No more than two of $A^1$, $A^2$, $A^3$, $A^4$, and $A^5$ may be nitrogen;
No more than two of $A^6$, $A^7$, $A^8$, $A^9$, and $A^{10}$ may be nitrogen;
$R^{10}$ is selected from the group consisting of hydrogen, $C_{1-6}$ alkyl, $C_{1-6}$ haloalkyl, $C_{1-6}$ haloalkoxy, $C_{1-6}$ alkoxy, halogen, hydroxy, and $NHSO_2R^{11}$;
and $R^{11}$ is independently selected from the group consisting of hydrogen and $C_{1-6}$ alkyl.

Another embodiment of the invention includes compounds having formula (XLI):

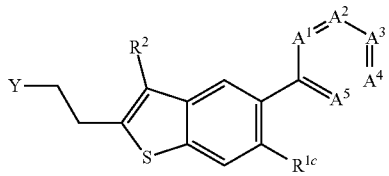
(XLI)

including enantiomers, diastereomers, hydrates, solvates, pharmaceutically acceptable salts, and complexes thereof, wherein $R^{1c}$, $R^2$ and Y are as defined for formula XXXI;
$A^1$, $A^2$, $A^3$, $A^4$, and $A^5$ are selected from the group consisting of nitrogen and $CR^{10}$;
No more than one of $A^1$, $A^2$, $A^3$, $A^4$, and $A^5$ may be nitrogen;
$R^{10}$ is selected from the group consisting of hydrogen, $C_{1-6}$ alkyl, $C_{1-6}$ haloalkyl, $C_{1-6}$ haloalkoxy, $C_{1-6}$ alkoxy, halogen, hydroxy, and $NHSO_2R^{11}$;
and $R^{11}$ is independently selected from the group consisting of hydrogen and $C_{1-6}$ alkyl.

Another embodiment of the invention includes compounds having formula (XLII):

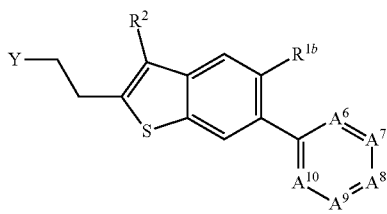
(XLII)

including enantiomers, diastereomers, hydrates, solvates, pharmaceutically acceptable salts, and complexes thereof, wherein $R^{1b}$, $R^2$ and Y are as defined for formula XXXI;
$A^6$, $A^7$, $A^8$, $A^9$, and $A^{10}$ are selected from the group consisting of nitrogen and $CR^{10}$;
No more than two of $A^6$, $A^7$, $A^8$, $A^9$, and $A^{10}$ may be nitrogen;
$R^{10}$ is selected from the group consisting of hydrogen, $C_{1-6}$ alkyl, $C_{1-6}$ haloalkyl, $C_{1-6}$ haloalkoxy, $C_{1-6}$ alkoxy, halogen, hydroxy, and $NHSO_2R^{11}$;
and $R^{11}$ is independently selected from the group consisting of hydrogen and $C_{1-6}$ alkyl.

Another embodiment of the invention includes compounds having formula (XLIII):

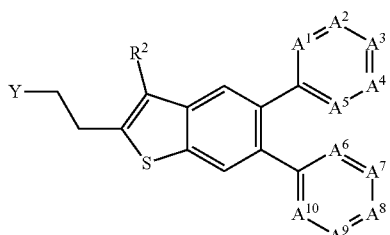
(XLIII)

including enantiomers, diastereomers, hydrates, solvates, pharmaceutically acceptable salts, and complexes thereof, wherein $R^2$ and Y are as defined for formula XXXI;

$A^1$, $A^2$, $A^3$, $A^4$, $A^5$, $A^6$, $A^7$, $A^8$, $A^9$, and $A^{10}$ are selected from the group consisting of nitrogen and $CR^{10}$;
No more than two of $A^1$, $A^2$, $A^3$, $A^4$, and $A^5$ may be nitrogen;
No more than two of $A^6$, $A^7$, $A^8$, $A^9$, and $A^{10}$ may be nitrogen;
$R^{10}$ is selected from the group consisting of hydrogen, $C_{1-6}$ alkyl, $C_{1-6}$ haloalkyl, $C_{1-6}$ haloalkoxy, $C_{1-6}$ alkoxy, halogen, hydroxy, and $NHSO_2R^{11}$;
and $R^{11}$ is independently selected from the group consisting of hydrogen and $C_{1-6}$ alkyl.

Another embodiment of the invention includes compounds having formula (XLIV):

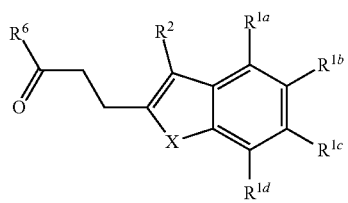
(XLIV)

including enantiomers, diastereomers, hydrates, solvates, pharmaceutically acceptable salts, and complexes thereof, wherein $R^{1a}$ and $R^{1d}$ are each independently selected from the group consisting of hydrogen, halogen, $C_{1-6}$ alkyl, $C_{1-6}$ alkoxy, $C_{1-6}$ haloalkyl, and $C_{1-6}$ haloalkoxy;
$R^{1b}$ and $R^{1c}$ are selected from the group consisting of hydrogen, halogen, optionally substituted aryl and optionally substituted heteroaryl;
When $R^{1b}$ is hydrogen, $R^{1c}$ is not hydrogen;
When $R^{1c}$ is hydrogen, $R^{1b}$ is not hydrogen;
$R^2$ is selected from the group consisting of $C_{1-6}$ alkyl, $C_{3-7}$ branched alkyl, $C_{1-6}$ alkylaryl, optionally substituted aryl and optionally substituted heteroaryl;
X is oxygen;
Wherein $R^6$ is selected from the group consisting of hydrogen, OH, $OR^{7c}$, optionally substituted $C_{1-6}$ alkyl, $NR^{3a}R^{3b}$, optionally substituted aryl, and optionally substituted heteroaryl;
$R^{3a}$ and $R^{3b}$ are independently selected from the group consisting of hydrogen and $C_{1-6}$ alkyl;
$R^{3a}$ and $R^{3b}$ are taken together with the atom to which they are bound to form a three to six membered saturated ring optionally substituted with a group selected from OH, $C_{1-6}$ alkyl, $NR^{8a}R^{8b}$ optionally including a member selected from the group consisting of O, $NR^8$, and S;
$R^8$ is selected from the group consisting of hydrogen, $C_{1-6}$ alkyl, and CO ($C_{1-6}$ alkyl;
$R^{8a}$ and $R^{8b}$ are independently selected from of hydrogen and $C_{1-6}$ alkyl, compounds having formula (XLV):

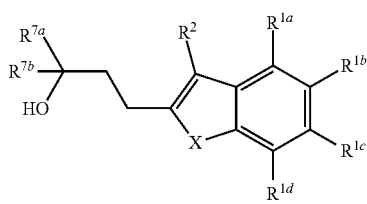
(XLV)

including enantiomers, diastereomers, hydrates, solvates, pharmaceutically acceptable salts, and complexes thereof, wherein $R^{1a}$ and $R^{1d}$ are each independently selected from the group consisting of hydrogen, halogen, $C_{1-6}$ alkyl, $C_{1-6}$ alkoxy, $C_{1-6}$ haloalkyl, and $C_{1-6}$ haloalkoxy;

$R^{1b}$ and $R^{1c}$ are selected from the group consisting of hydrogen, halogen, optionally substituted aryl and optionally substituted heteroaryl;

When $R^{1b}$ is hydrogen, $R^{1c}$ is not hydrogen;

When $R^{1c}$ is hydrogen, $R^{1b}$ is not hydrogen;

$R^2$ is selected from the group consisting of $C_{1-6}$ alkyl, $C_{3-7}$ branched alkyl, $C_{1-6}$ alkylaryl, optionally substituted aryl and optionally substituted heteroaryl;

X is oxygen;

Wherein $R^6$ is selected from the group consisting of hydrogen, OH, $OR^{7c}$, optionally substituted $C_{1-6}$ alkyl, $NR^{3a}R^{3b}$, optionally substituted aryl, and optionally substituted heteroaryl;

$R^{3a}$ and $R^{3b}$ are independently selected from the group consisting of hydrogen and $C_{1-6}$ alkyl;

$R^{3a}$ and $R^{3b}$ are taken together with the atom to which they are bound to form a three to six membered saturated ring optionally substituted with a group selected from OH, $C_{1-6}$ alkyl, $NR^{8a}R^{8b}$ optionally including a member selected from the group consisting of O, $NR^8$, and S;

$R^8$ is selected from the group consisting of hydrogen, $C_{1-6}$ alkyl, and CO ($C_{1-6}$ alkyl);

$R^{8a}$ and $R^{8b}$ are independently selected from of hydrogen and $C_{1-6}$ alkyl.

$R^{7a}$ is selected from the group consisting of hydrogen and $C_{1-6}$ alkyl;

$R^{7b}$ is selected from the group consisting of $C_{1-6}$ alkyl, aryl, and heteroaryl.

Another embodiment of the invention includes compounds selected from the following structures:

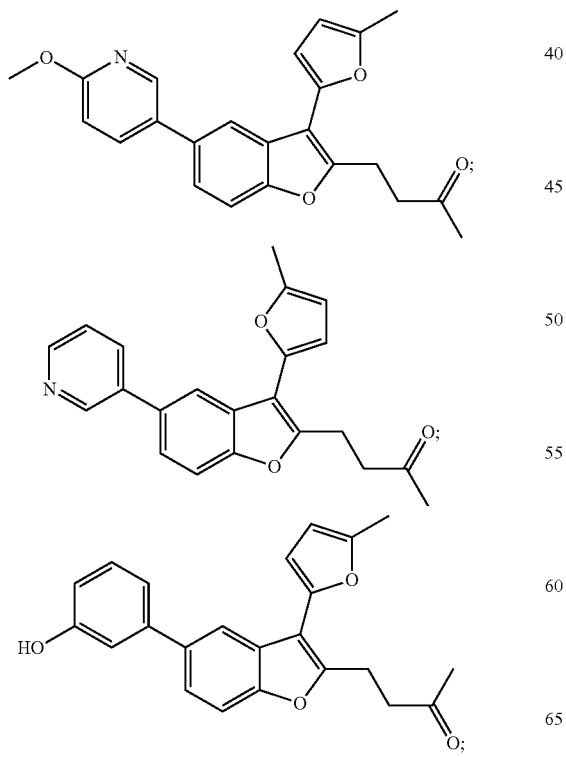

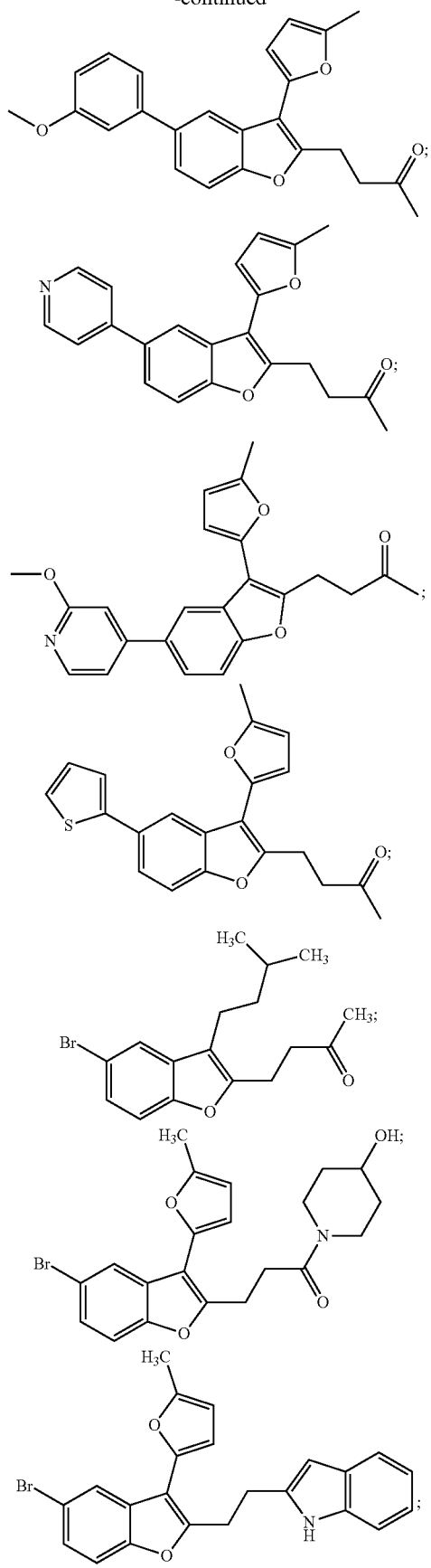

37
-continued
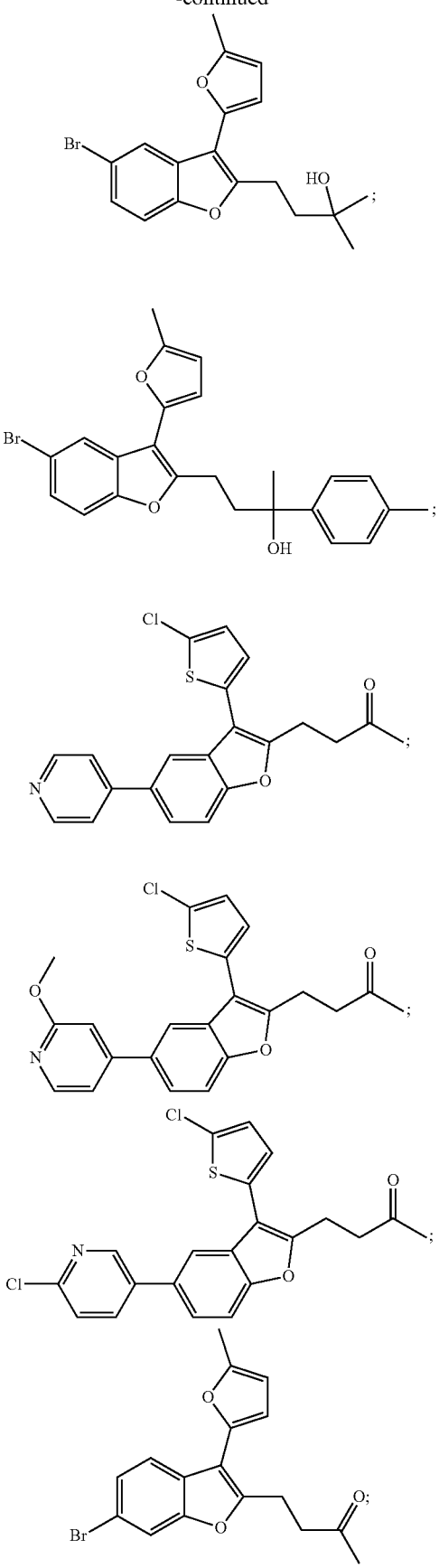
38
-continued
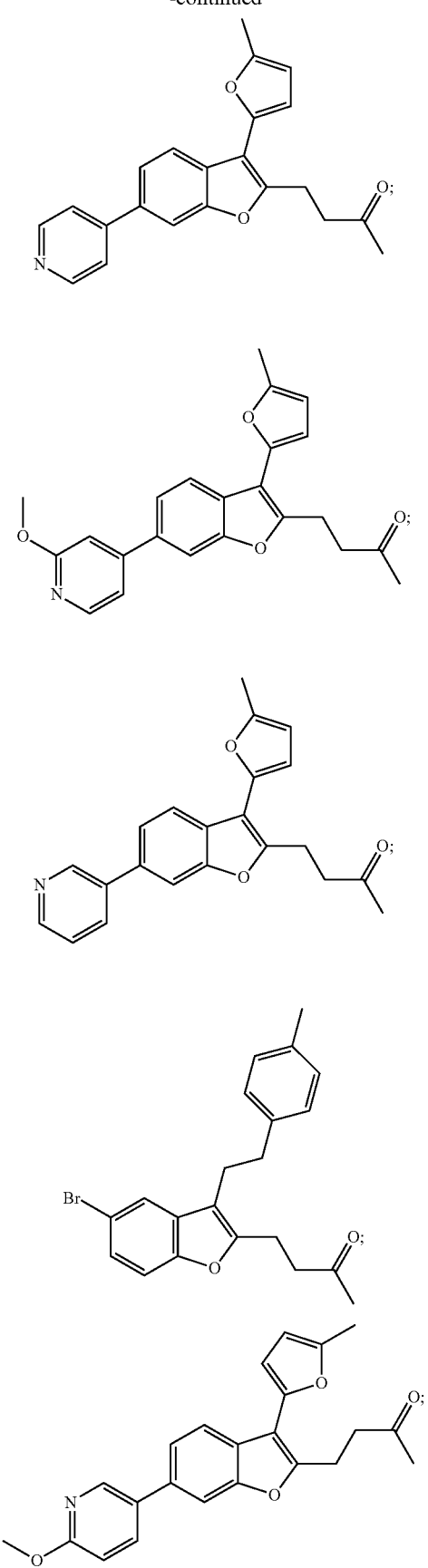

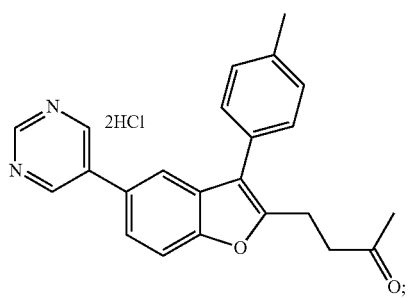
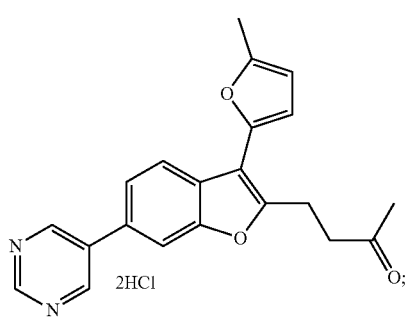
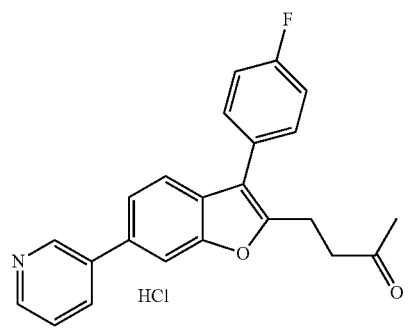
Another embodiment of the invention includes compounds selected from the following structures:
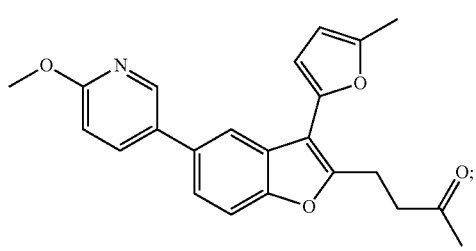
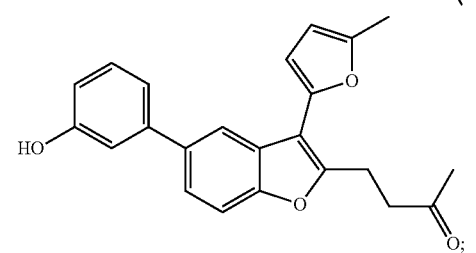
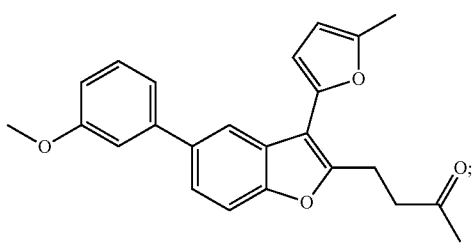
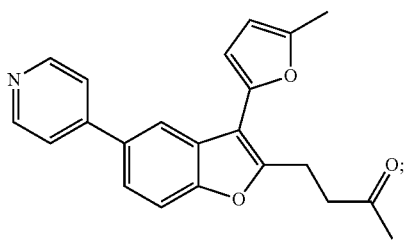
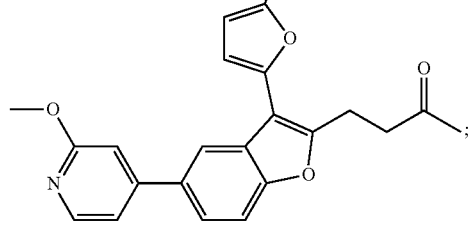
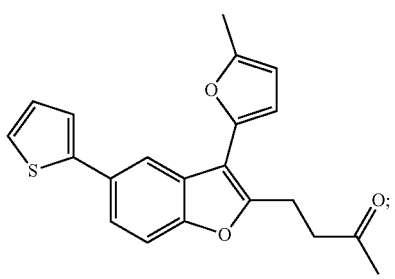
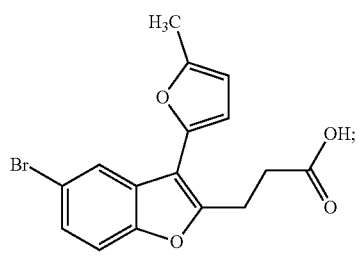
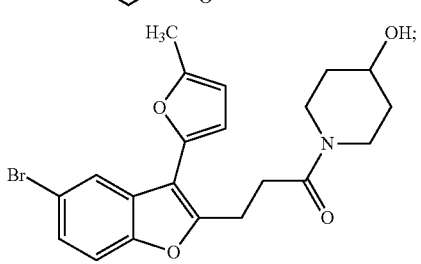

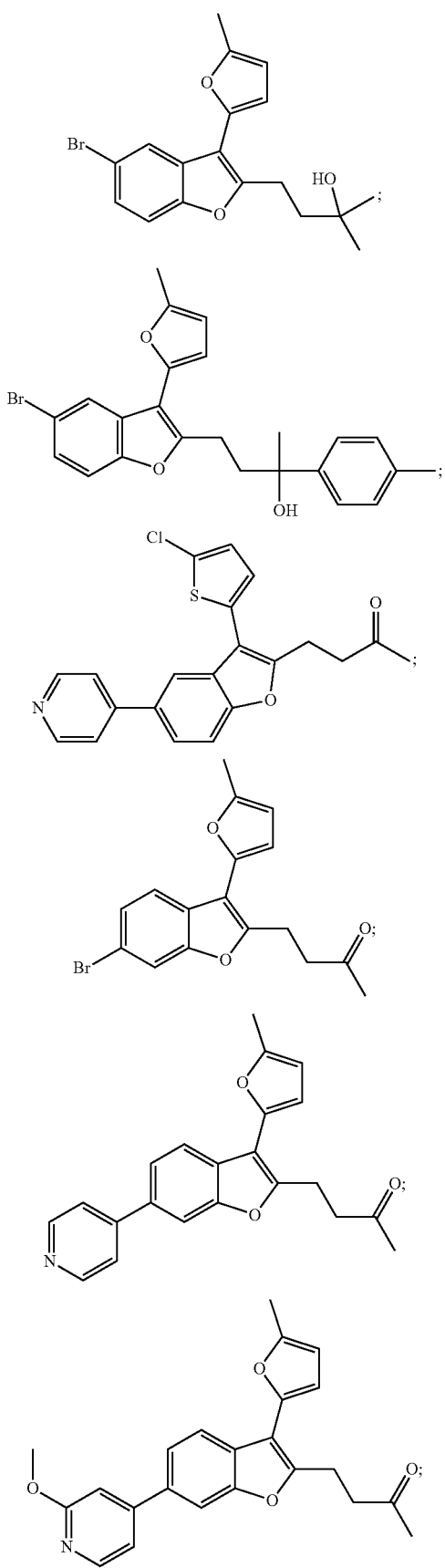
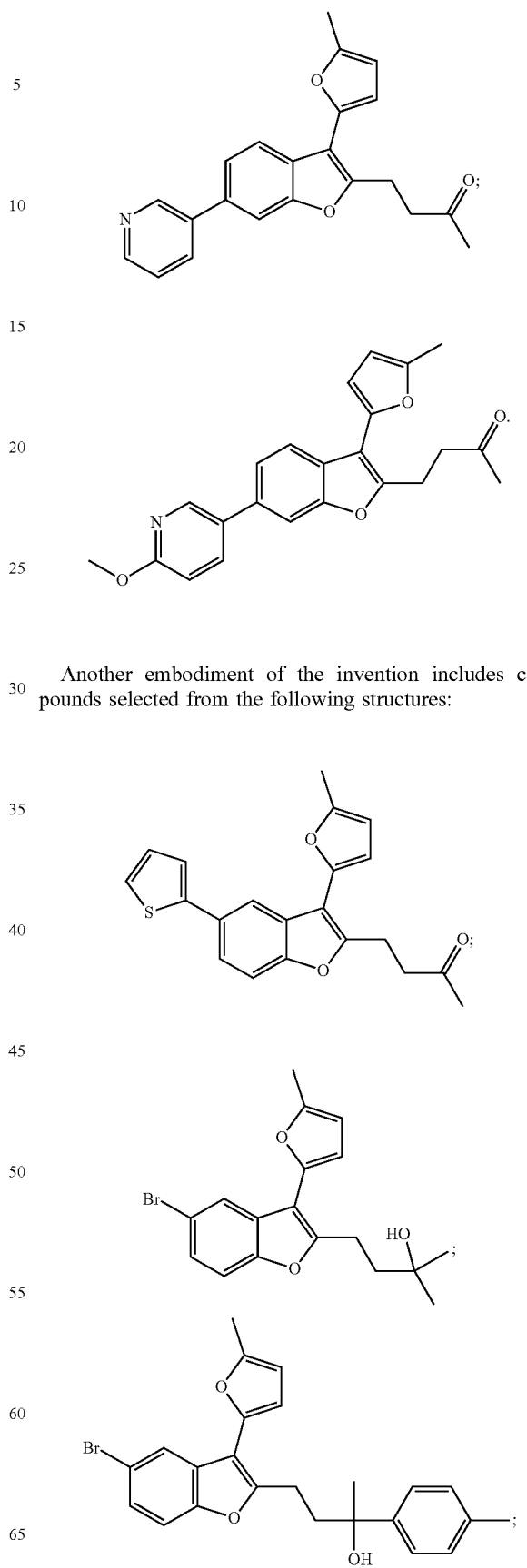
Another embodiment of the invention includes compounds selected from the following structures:

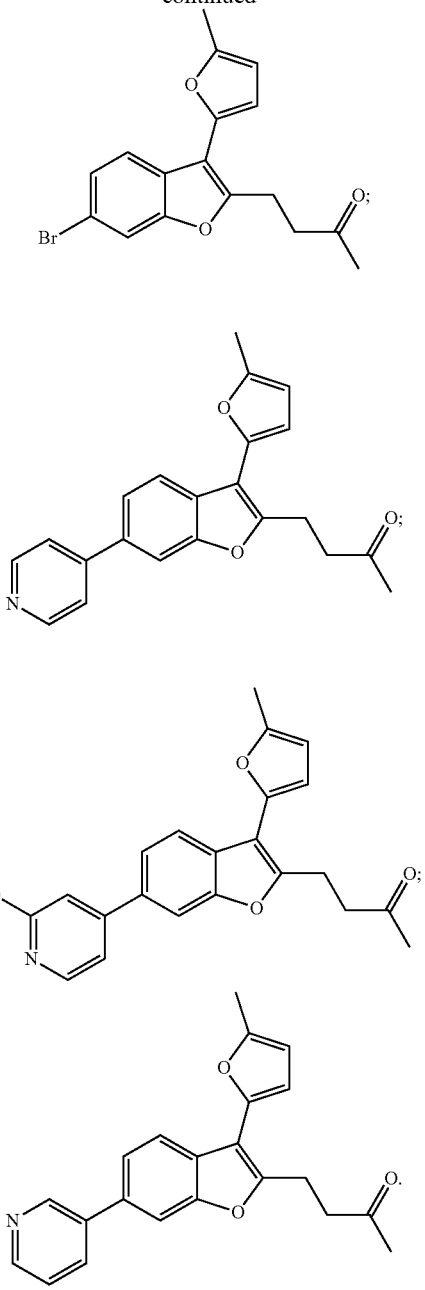

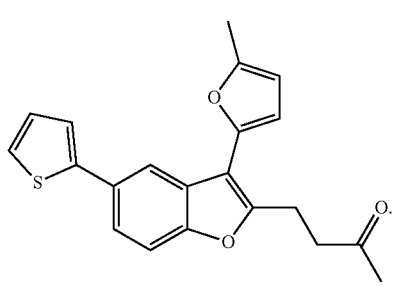 [SMILES: CC(=O)CCc1oc2ccc(-c3cccs3)cc2c1-c1ccc(C)o1]

Another embodiment of the invention includes the compound that has the following structure:

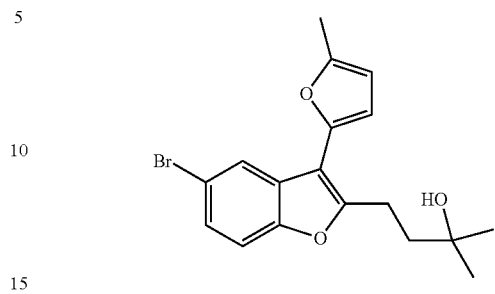

Another embodiment of the invention includes the compound that has the following structure:

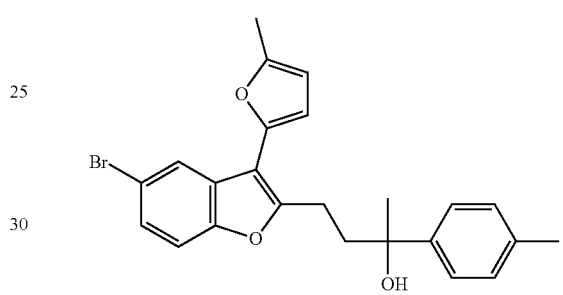

Another embodiment of the invention includes the compound that has the following structure:

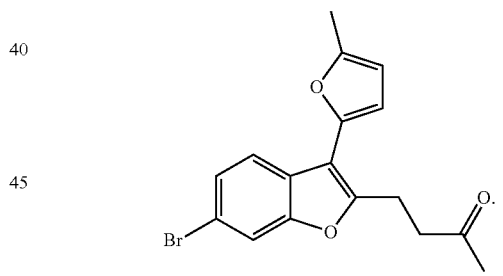

Another embodiment of the invention includes the compound that has the following structure:

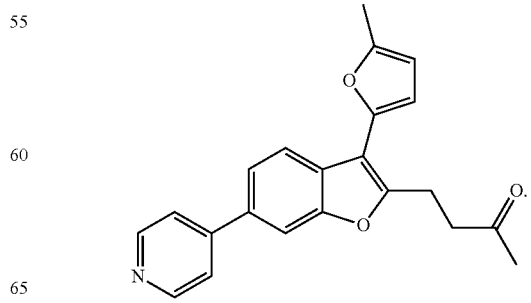

Another embodiment of the invention includes the compound that has the following structure:

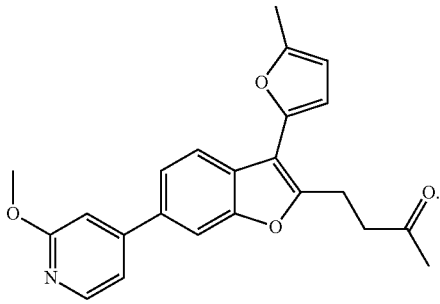 [SMILES: COc1cc(-c2ccc3c(-c4ccc(C)o4)c(CCC(C)=O)oc3c2)ccn1]

Another embodiment of the invention includes the compound that has the following structure:

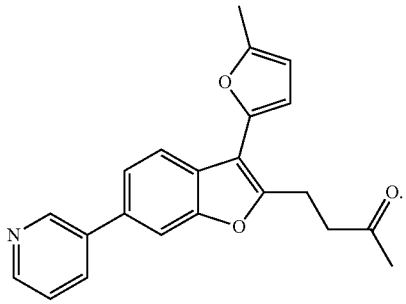 [SMILES: CC(=O)CCc1oc2cc(-c3cccnc3)ccc2c1-c1ccc(C)o1]

In some embodiments $R^{1a}$ is hydrogen.
In some embodiments $R^{1a}$ is halogen.
In some embodiments $R^{1a}$ is $C_{1-6}$ alkyl.
In some embodiments $R^{1a}$ is $C_{1-6}$ alkoxy.
In some embodiments $R^{1a}$ is $C_{1-6}$ haloalkyl.
In some embodiments $R^{1a}$ is $C_{1-6}$ haloalkoxy.
In some embodiments $R^{1d}$ is hydrogen.
In some embodiments $R^{1d}$ is halogen.
In some embodiments $R^{1d}$ is $C_{1-6}$ alkyl.
In some embodiments $R^{1d}$ is $C_{1-6}$ alkoxy.
In some embodiments $R^{1d}$ is $C_{1-6}$ haloalkyl.
In some embodiments $R^{1d}$ is $C_{1-6}$ haloalkoxy.
In some embodiments $R^{1b}$ is hydrogen.
In some embodiments $R^{1b}$ is halogen.
In some embodiments $R^{1b}$ is optionally substituted aryl.
In some embodiments $R^{1b}$ is optionally substituted heteroaryl.
In some embodiments $R^{1c}$ is hydrogen.
In some embodiments $R^{1c}$ is halogen.
In some embodiments $R^{1c}$ is optionally substituted aryl.
In some embodiments $R^{1c}$ is optionally substituted heteroaryl.
In some embodiments $R^2$ is $C_{1-6}$ alkyl.
In some embodiments $R^2$ is $C_{3-7}$ branched alkyl.
In some embodiments $R^2$ is $C_{1-6}$ alkylaryl.
In some embodiments $R^2$ is optionally substituted aryl.
In some embodiments $R^2$ is optionally substituted heteroaryl.
In some embodiments X is oxygen.
In some embodiments X is sulfur.
In some embodiments X is NH.
In some embodiments X is $NR^5$.
In some embodiments $R^2$ is $C_{1-6}$ alkyl.

In some embodiments Y is

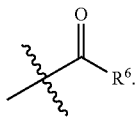

In some embodiments Y is

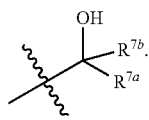

In some embodiments Y is optionally substituted 2-benzimidazole.
In some embodiments $R^6$ is hydrogen.
In some embodiments $R^6$ is OH.
In some embodiments $R^6$ is $OR^{7c}$.
In some embodiments $R^6$ is optionally substituted $C_{1-6}$ alkyl.
In some embodiments $R^6$ is $NR^{3a}R^{3b}$.
In some embodiments $R^6$ is optionally substituted aryl.
In some embodiments $R^6$ is optionally substituted heteroaryl.
In some embodiments $R^{3a}$ is hydrogen.
In some embodiments $R^{3a}$ is $C_{1-6}$ alkyl.
In some embodiments $R^{3b}$ is hydrogen.
In some embodiments $R^{3b}$ is $C_{1-6}$ alkyl.
In some embodiments $R^{3a}$ and $R^{3b}$ are taken together with the atom to which they are bound to form a three membered saturated ring optionally substituted with a group selected from OH, $C_{1-6}$ alkyl, $NR^{8a}R^{8b}$ optionally including a member selected from the group consisting of O, $NR^8$, and S.
In some embodiments $R^{3a}$ and $R^{3b}$ are taken together with the atom to which they are bound to form a four membered saturated ring optionally substituted with a group selected from OH, $C_{1-6}$ alkyl, $NR^{8a}R^{8b}$ optionally including a member selected from the group consisting of O, $NR^8$, and S.
In some embodiments $R^{3a}$ and $R^{3b}$ are taken together with the atom to which they are bound to form a five membered saturated ring optionally substituted with a group selected from OH, $C_{1-6}$ alkyl, $NR^{8a}R^{8b}$ optionally including a member selected from the group consisting of O, $NR^8$, and S.
In some embodiments $R^{3a}$ and $R^{3b}$ are taken together with the atom to which they are bound to form a six membered saturated ring optionally substituted with a group selected from OH, $C_{1-6}$ alkyl, $NR^{8a}R^{8b}$ optionally including a member selected from the group consisting of O, $NR^8$, and S.
In some embodiments $R^8$ is hydrogen.
In some embodiments $R^8$ is $C_{1-6}$ alkyl.
In some embodiments $R^8$ is $CO(C_{1-6}alkyl)$.
In some embodiments $R^{8a}$ is hydrogen.
In some embodiments $R^{8a}$ is $C_{1-6}$ alkyl.
In some embodiments $R^{8b}$ is hydrogen.
In some embodiments $R^{8b}$ is $C_{1-6}$ alkyl.
In some embodiments $R^{7a}$ is hydrogen.
In some embodiments $R^{7a}$ is $C_{1-6}$ alkyl.
In some embodiments $R^{7b}$ is $C_{1-6}$ alkyl.
In some embodiments $R^{7b}$ is aryl.
In some embodiments $R^{7b}$ is heteroaryl.
In some embodiments $R^{7c}$ is $C_{1-6}$ alkyl.
In some embodiments $R^{7c}$ is $C_{3-7}$ branch alkyl.

In some embodiments $R^{9a}$ is hydrogen.
In some embodiments $R^{9a}$ is halogen.
In some embodiments $R^{9a}$ is $C_{1-6}$ alkyl.
In some embodiments $R^{9b}$ is hydrogen.
In some embodiments $R^{9b}$ is halogen.
In some embodiments $R^{9b}$ is $C_{1-6}$ alkyl.
In some embodiments $R^{9c}$ is hydrogen.
In some embodiments $R^{9c}$ is halogen.
In some embodiments $R^{9c}$ is $C_{1-6}$ alkyl.
In some embodiments $X^1$ is oxygen.
In some embodiments $X^1$ is sulfur.
In some embodiments $A^1$ is nitrogen.
In some embodiments $A^1$ is $CR^{10}$.
In some embodiments $A^2$ is nitrogen.
In some embodiments $A^2$ is $CR^{10}$.
In some embodiments $A^3$ is nitrogen.
In some embodiments $A^3$ is $CR^{10}$.
In some embodiments $A^4$ is nitrogen.
In some embodiments $A^4$ is $CR^{10}$.
In some embodiments $A^5$ is nitrogen.
In some embodiments $A^5$ is $CR^{10}$.
In some embodiments $A^6$ is nitrogen.
In some embodiments $A^6$ is $CR^{10}$.
In some embodiments $A^7$ is nitrogen.
In some embodiments $A^7$ is $CR^{10}$.
In some embodiments $A^8$ is nitrogen.
In some embodiments $A^8$ is $CR^{10}$.
In some embodiments $A^9$ is nitrogen.
In some embodiments $A^9$ is $CR^{10}$.
In some embodiments $A^{10}$ is nitrogen.
In some embodiments $A^{10}$ is $CR^{10}$.
In some embodiments $R^{10}$ is hydrogen.
In some embodiments $R^{10}$ is $C_{1-6}$ alkyl.
In some embodiments $R^{10}$ is $C_{1-6}$ haloalkyl.
In some embodiments $R^{10}$ is $C_{1-6}$ haloalkoxy.
In some embodiments $R^{10}$ is $C_{1-6}$ alkoxy.
In some embodiments $R^{10}$ is halogen.
In some embodiments $R^{10}$ is hydroxyl.
In some embodiments $R^{10}$ is $NHSO_2R^{11}$.
In some embodiments $R^{11}$ is hydrogen.
In some embodiments $R^{11}$ is $C_{1-6}$ alkyl.

Exemplary non-limiting embodiments of the invention include the compounds of tables 1, 2 and 3.

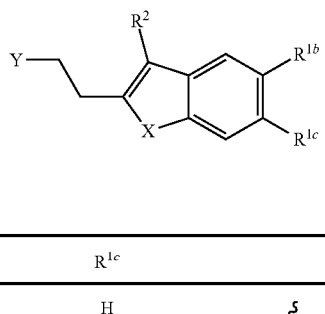

(I)

TABLE 1

| Entry | X | Y | $R^{1b}$ | $R^{1c}$ | $R^2$ |
|---|---|---|---|---|---|
| 1 | O | ketone (acyl) | 6-chloropyridin-3-yl | H | 5-chlorothiophen-2-yl |
| 2 | O | ketone (acyl) | 2-methoxypyridin-4-yl | H | 5-chlorothiophen-2-yl |
| 3 | O | ketone (acyl) | pyridin-4-yl | H | 5-chlorothiophen-2-yl |
| 4 | O | ketone (acyl) | Br | H | 5-chlorothiophen-2-yl |
| 5 | O | ketone (acyl) | Br | H | 4-methylphenyl |
| 6 | O | ketone (acyl) | Br | H | Phenyl |

TABLE 1-continued

| Entry | X | Y | R$^{1b}$ | R$^{1c}$ | R$^2$ |
|---|---|---|---|---|---|
| 7 | O | benzimidazol-2-yl | Br | H | 5-methylfuran-2-yl |
| 8 | O | acetyl | pyridin-3-yl | H | 5-methylfuran-2-yl |
| 9 | O | acetyl | 6-methoxypyridin-3-yl | H | 5-methylfuran-2-yl |
| 10 | O | acetyl | pyridin-4-yl | H | 5-methylfuran-2-yl |
| 11 | O | acetyl | 2-methoxypyridin-4-yl | H | 5-methylfuran-2-yl |
| 12 | O | acetyl | Br | H | 4-methylbenzyl |
| 13 | O | carboxylic acid | Br | H | 5-methylfuran-2-yl |
| 14 | O | acetyl | 3-hydroxyphenyl | H | 5-methylfuran-2-yl |
| 15 | O | acetyl | H | pyridin-4-yl | 5-methylfuran-2-yl |
| 16 | O | 4-hydroxypiperidin-1-ylcarbonyl | Br | H | 5-methylfuran-2-yl |
| 17 | O | acetyl | H | 6-methoxypyridin-3-yl | 5-methylfuran-2-yl |
| 18 | O | acetyl | 3-methoxyphenyl | H | 5-methylfuran-2-yl |

TABLE 1-continued

| Entry | X | Y | R$^{1b}$ | R$^{1c}$ | R$^2$ |
|---|---|---|---|---|---|
| 19 | O | (ketone) | 2-thienyl | H | 5-methylfuran-2-yl |
| 20 | O | (ketone) | H | 2-methoxypyridin-4-yl | 5-methylfuran-2-yl |
| 20 | O | (ketone) | H | pyridin-3-yl | 5-methylfuran-2-yl |
| 21 | O | (ketone) | Br | H | phenethyl |
| 22 | O | (ketone) | Br | H | 4-methylphenethyl |
| 23 | O | (ketone) | N-methyl-N-(methylsulfonyl)aniline-3-yl | H | 5-methylfuran-2-yl |
| 24 | O | (ketone) | Br | H | isopentyl |
| 25 | O | (ketone) | Br | H | 5-methylfuran-2-yl |

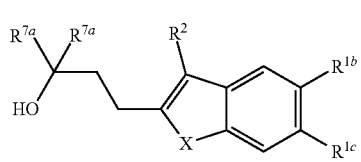

(I)

TABLE 2

| Entry | X | R$^{1b}$ | R$^{1c}$ | R$^2$ | R$^{7a}$ | R$^{7b}$ |
|---|---|---|---|---|---|---|
| 1 | O | Br | H | 5-methylfuran-2-yl | CH$_3$ | 4-methylphenyl |
| 2 | O | Br | H | 5-methylfuran-2-yl | CH$_3$ | CH$_3$ |

For the purposes of demonstrating the manner in which the compounds of the present invention are named and referred to herein, the compound having the formula:

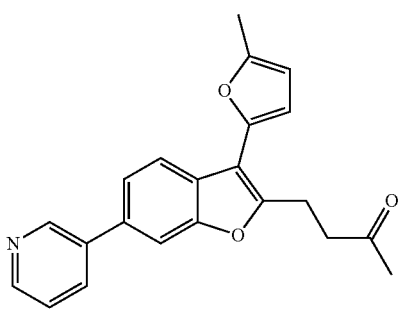 [SMILES: CC(=O)CCc1oc2cc(-c3cccnc3)ccc2c1-c1ccc(C)o1]

has the chemical name 4-(3-(5-methylfuran-2-yl)-6-(pyridin-3-yl)benzofuran-2-yl)butan-2-one.

For the purposes of the present invention, a compound depicted by the racemic formula will stand equally well for either of the two enantiomers or mixtures thereof, or in the case where a second chiral center is present, all diastereomers.

In all of the embodiments provided herein, examples of suitable optional substituents are not intended to limit the scope of the claimed invention. The compounds of the invention may contain any of the substituents, or combinations of substituents, provided herein.

Process

Compounds of the present teachings can be prepared in accordance with the procedures outlined herein, from commercially available starting materials, compounds known in the literature, or readily prepared intermediates, by employing standard synthetic methods and procedures known to those skilled in the art. Standard synthetic methods and procedures for the preparation of organic molecules and functional group transformations and manipulations can be readily obtained from the relevant scientific literature or from standard textbooks in the field. It will be appreciated that where typical or preferred process conditions (i.e., reaction temperatures, times, mole ratios of reactants, solvents, pressures, etc.) are given, other process conditions can also be used unless otherwise stated. Optimum reaction conditions can vary with the particular reactants or solvent used, but such conditions can be determined by one skilled in the art by routine optimization procedures. Those skilled in the art of organic synthesis will recognize that the nature and order of the synthetic steps presented can be varied for the purpose of optimizing the formation of the compounds described herein.

The processes described herein can be monitored according to any suitable method known in the art. For example, product formation can be monitored by spectroscopic means, such as nuclear magnetic resonance spectroscopy (e.g., $^1$H or $^{13}$C), infrared spectroscopy, spectrophotometry (e.g., UV-visible), mass spectrometry, or by chromatography such as high pressure liquid chromatography (HPLC), gas chromatography (GC), gel-permeation chromatography (GPC), or thin layer chromatography (TLC).

Preparation of the compounds can involve protection and deprotection of various chemical groups. The need for protection and deprotection and the selection of appropriate protecting groups can be readily determined by one skilled in the art. The chemistry of protecting groups can be found, for example, in Greene et al., *Protective Groups in Organic Synthesis*, 2d. Ed. (Wiley & Sons, 1991), the entire disclosure of which is incorporated by reference herein for all purposes.

The reactions or the processes described herein can be carried out in suitable solvents which can be readily selected by one skilled in the art of organic synthesis. Suitable solvents typically are substantially nonreactive with the reactants, intermediates, and/or products at the temperatures at which the reactions are carried out, i.e., temperatures that can range from the solvent's freezing temperature to the solvent's boiling temperature. A given reaction can be carried out in one solvent or a mixture of more than one solvent. Depending on the particular reaction step, suitable solvents for a particular reaction step can be selected.

The compounds of these teachings can be prepared by methods known in the art of organic chemistry. The reagents used in the preparation of the compounds of these teachings can be either commercially obtained or can be prepared by standard procedures described in the literature. For example, compounds of the present invention can be prepared according to the method illustrated in the General Synthetic Schemes:

General Synthetic Schemes for Preparation of Compounds

The reagents used in the preparation of the compounds of this invention can be either commercially obtained or can be prepared by standard procedures described in the literature. In accordance with this invention, compounds in the genus may be produced by one of the following reaction schemes.

Compounds of formula (I) may be prepared according to the process outlined in schemes 1-9 as reported in the literature.

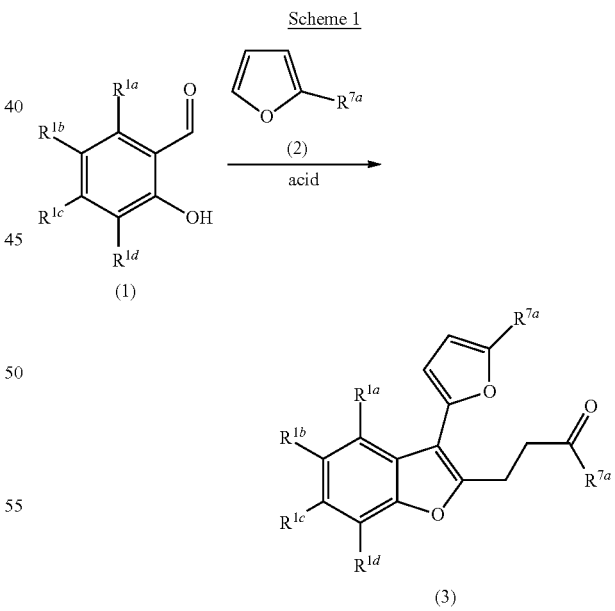

Accordingly, a suitably substituted compound of the formula (1), a known compound or compound prepared by known methods, is reacted with a suitably substituted compound of the formula (2) in the presence of an acid such as hydrochloric, phosphoric, or sulfuric acid in a solvent such as water, acetic acid, or ethanol to provide a compound of the formula (3).

Scheme 2

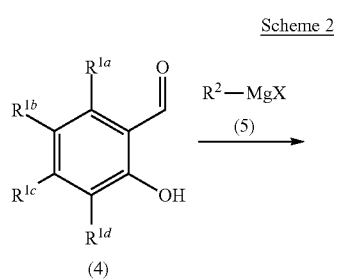
(4)

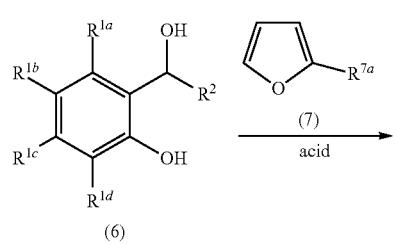
(6)

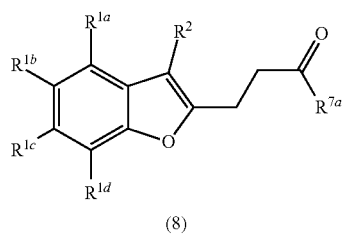
(8)

Alternatively, a suitably substituted compound of the formula (4), a known compound or compound prepared by known methods, is reacted with a suitably substituted compound of the formula (5) where in X is a halogen, a known compound or compound prepared by known methods in the presence of a solvent such as ethyl ether, dioxane, or THF (tetrahydrofuran) to provide a compound of the formula (6). A compound of the formula (6) is reacted with a compound of the formula (7), a known compound or a compound prepared by known methods, in the presence of an acid such as hydrochloric, phosphoric acid, or sulfuric acid in a solvent such as water, acetic acid, or ethanol to provide a compound of the formula (8).

Scheme 3

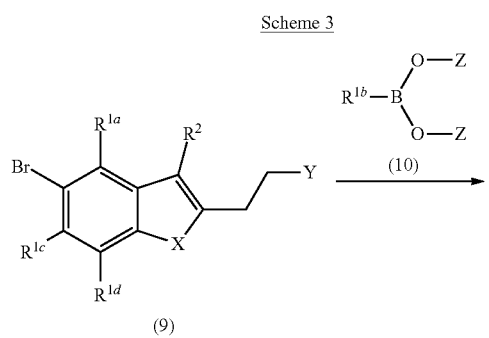
(9)

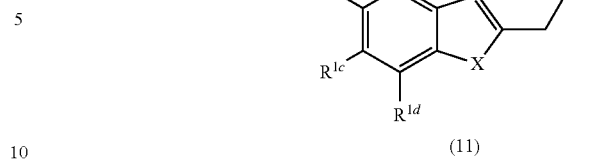
(11)

A suitably substituted compound of the formula (9), a known compound or compound prepared by known methods, is reacted with a suitably substituted compound of the formula (10), a known compound or a compound prepared by known methods wherein Z is selected from a group consisting of hydrogen, $C_1$-$C_6$ linear alkyl, and $C_3$-$C_6$ branched alkyl, in the presence of a palladium catalyst such as palladium acetate, palladium bis(triphenylphosphine) dichloride, palladium tetrakis(triphenylphosphine), bis(acetonitrile) dichloropalladium [1,1'-Bis(diphenylphosphino)ferrocene]dichloropalladium, and the like, in the presence of a base such as potassium carbonate, sodium carbonate, lithium carbonate, cesium carbonate, sodium hydroxide, lithium hydroxide, potassium hydroxide, and the like in a solvent such as methanol, ethanol, isopropanol, 1-butanol, tetrahydrofuran, 1,4-dioxane, N,N-dimethylformamide, N,N-dimethyl acetamide, dichloromethane, 1,2-dichloroethane, and the like, optionally in the presence of water, optionally with heating, optionally with microwave irradiation to provide a compound of the formula (11).

Scheme 4

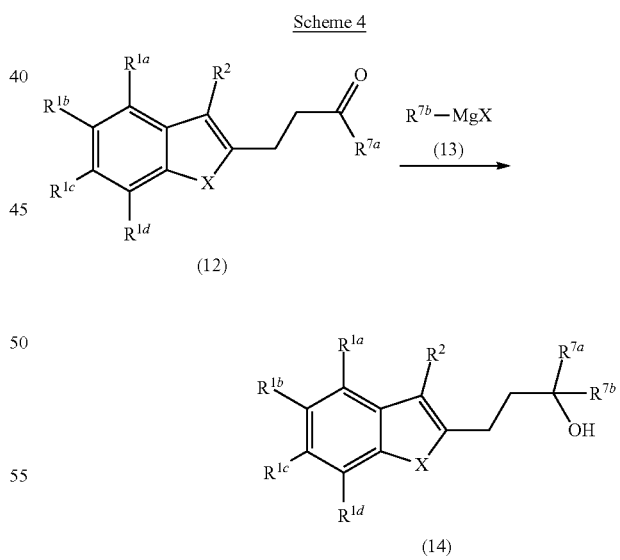

A suitably substituted compound of the formula (12), is reacted with a suitably substituted compound of the formula (13) where in X is a halogen, a known compound or compound prepared by known methods, in the presence of a solvent such as tetrahydrofuran, dioxane, or ethyl ether to provide a compound of the formula (14).

Scheme 5

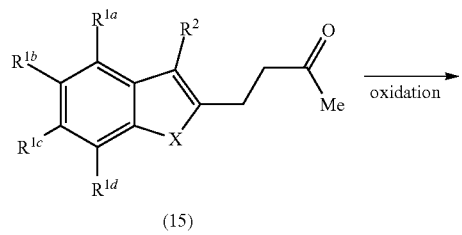

A suitably substituted compound of the formula (15), is oxidized with an alkaline hypohalite reagent such as sodium hypochlorite in aqueous sodium hydroxide, or potassium permanganate in aqueous sodium carbonate and the like, optionally with heating, optionally with microwave irradiation to provide a compound of the formula (16). A compound of the formula (16) is reacted with a compound of the formula (17), a known compound or compound prepared by known methods, in the presence of a coupling agent such as O-(benzotriazol-1-yl)-N,N,N',N'-tetramethyluronium hexafluorophosphate, N,N'-dicyclohexylcarbodiimide, 1-ethyl-3-(3-dimethylaminopropyl) carbodiimide, 1-[Bis(dimethylamino)methylene]-1H-1,2,3-triazolo[4,5-b]pyridinium 3-oxide hexafluorophosphate, 1-hydroxy-7-azabenzotriazole and the like, optionally in the presence of a base such as triethylamine, N,N-diisopropylethylamine, N-methylmorpholine and the like, in a solvent such as N,N-dimethylformamide, 1,4-dioxane, tetrahydrofuran, methylene chloride and the like, optionally with heating, optionally with microwave irradiation to provide a compound of the formula (18). Alternatively, a compound of the formula (16) is reacted with a compound of the formula (17), a known compound or compound prepared by known methods, in the presence of an acid such as hydrochloric acid, hydrobromic acid, sulfuric acid, trifluoroacetic acid, and the like, in a solvent such as N,N-dimethylformamide, 1,4-dioxane, tetrahydrofuran, methylene chloride, methanol, ethanol, and the like, optionally with heating, optionally with microwave irradiation to provide a compound of the formula (18).

Scheme 6

A suitably substituted compound of the formula (19), is reacted with a compound of the formula (20), a known compound or compound prepared by known methods, in the presence of a coupling agent such as O-(benzotriazol-1-yl)-N,N,N',N'-tetramethyluronium hexafluorophosphate, N,N'-dicyclohexylcarbodiimide, 1-ethyl-3-(3-dimethylaminopropyl) carbodiimide, 1-[Bis(dimethylamino)methylene]-1H-1,2,3-triazolo[4,5-b]pyridinium 3-oxide hexafluorophosphate, 1-hydroxy-7-azabenzotriazole and the like, optionally in the presence of a base such as triethylamine, N,N-diisopropylethylamine, N-methylmorpholine and the like, in a solvent such as N,N-dimethylformamide, 1,4-dioxane, tetrahydrofuran, methylene chloride and the like, optionally with heating, optionally with microwave irradiation to provide a compound of the formula (21).

Scheme 7

A suitably substituted compound of the formula (22), is condensed with a compound of the formula (23), a known compound or compound prepared by known methods, in the presence of an agent such as triphenyl phosphite, phosphorous oxychloride, in the presence of a solvent such as pyridine, or neat polyphosphoric acid or neat formic acid, optionally with heating, optionally with microwave irradiation to provide a compound of the formula (24).

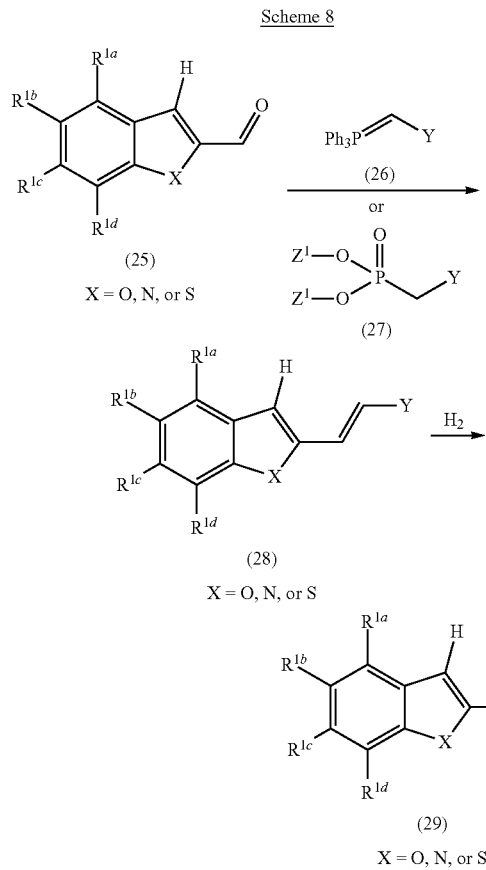

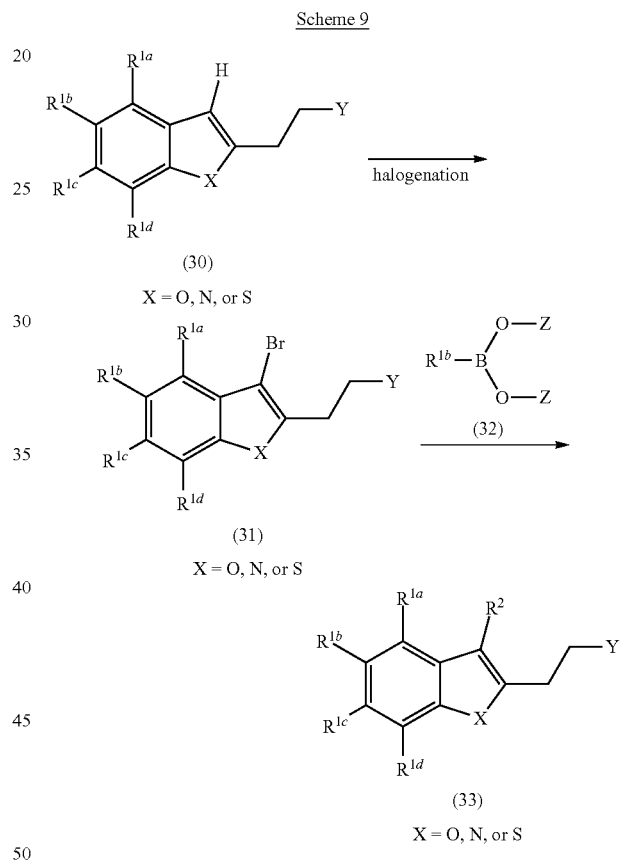

A suitably substituted compound of the formula (25), is reacted with a compound of the formula (26), a known compound or compound prepared by known methods, in the presence of a solvent such as benzene, toluene, tetrahydrofuran, dioxane, or ethyl ether optionally with heating, optionally with microwave irradiation to provide a compound of the formula (28). Alternatively, a suitably substituted compound of the formula (25), is reacted with a compound of the formula (27), a known compound or compound prepared by known methods, in the presence of a base such as potassium carbonate, sodium carbonate, lithium carbonate, cesium carbonate, sodium hydroxide, lithium hydroxide, potassium hydroxide, and the like in a solvent such as methanol, ethanol, isopropanol, 1-butanol, tetrahydrofuran, 1,4-dioxane, N,N-dimethylformamide, N, N-dimethyl acetamide, dichloromethane, 1,2-dichloroethane, and the like, optionally in the presence of water, optionally with heating, optionally with microwave irradiation to provide a compound of the formula (28). Alternatively, a suitably substituted compound of the formula (25), is reacted with a compound of the formula (27), a known compound or compound prepared by known methods, in the presence of a base such as triethylamine, N,N-diisopropylethylamine, N-methylmorpholine and the like, in the presence of lithium chloride, in a solvent such as methanol, ethanol, isopropanol, 1-butanol, tetrahydrofuran, 1,4-dioxane, N,N-dimethylformamide, N, N-dimethyl acetamide, dichloromethane, 1,2-dichloroethane, and the like, optionally in the presence of water, optionally with heating, optionally with microwave irradiation to provide a compound of the formula (28). A compound of the formula (28) is reacted with hydrogen in the presence of a palladium catalyst such as palladium on carbon, palladium on barium sulfate, palladium (II) acetate, tetrakis(triphenylphosphine) palladium(O), dichlorobis(triphenylphosphine)palladium (II), palladium on carbon, bis(acetonitrile)dichloropalladium(II), and the like, in an organic solvent such as methanol, ethanol, ethyl acetate, tetrahydrofuran, 1,4-dioxane, dichloromethane, chloroform, 1,2-dichloroethane, N,N-dimethylformamide, and the like, to provide a compound of the formula (29).

A suitably substituted compound of the formula (30) is reacted with a halogenating reagent such as N-iodosuccinimide, N-bromosuccinimide, iodine, or bromine and the like in the presence of a solvent such as pyridine, dimethylformamide, tetrahydrofuran, acetic acid, optionally with heating, optionally with microwave irradiation to provide a compound of the formula (31). A compound of the formula (31), a known compound or compound prepared by known methods, is reacted with a suitably substituted compound of the formula (32), a known compound or a compound prepared by known methods wherein Z is selected from a group consisting of hydrogen, $C_1$-$C_6$ linear alkyl, and $C_3$-$C_6$ branched alkyl, in the presence of a palladium catalyst such as palladium acetate, palladium bis(triphenylphosphine) dichloride, palladium tetrakis(triphenylphosphine), bis(acetonitrile) dichloropalladium [1,1'-Bis(diphenylphosphino)

ferrocene]dichloro palladium, and the like, in the presence of a base such as potassium carbonate, sodium carbonate, lithium carbonate, cesium carbonate, sodium hydroxide, lithium hydroxide, potassium hydroxide, and the like in a solvent such as methanol, ethanol, isopropanol, 1-butanol, tetrahydrofuran, 1,4-dioxane, N,N-dimethylformamide, N, N-dimethyl acetamide, dichloromethane, 1,2-dichloroethane, and the like, optionally in the presence of water, optionally with heating, optionally with microwave irradiation to provide a compound of the formula (33).

Cis/trans isomers may be separated by conventional techniques well known to those skilled in the art, for example, chromatography and fractional crystallisation.

Conventional techniques for the preparation/isolation of individual enantiomers include chiral synthesis from a suitable optically pure precursor or resolution of the racemate (or the racemate of a salt or derivative) using, for example, chiral high pressure liquid chromatography (HPLC).

Alternatively, the racemate (or a racemic precursor) may be reacted with a suitable optically active compound, for example, an alcohol, or, in the case where the compound of formula (I) contains an acidic or basic moiety, an acid or base such as tartaric acid or 1-phenylethylamine. The resulting diastereomeric mixture may be separated by chromatography and/or fractional crystallization and one or both of the diastereoisomers converted to the corresponding pure enantiomer(s) by means well known to a skilled person.

Chiral compounds of the invention (and chiral precursors thereof) may be obtained in enantiomerically-enriched form using chromatography, typically HPLC, on a resin with an asymmetric stationary phase and with a mobile phase consisting of a hydrocarbon, typically heptane or hexane, containing from 0 to 50% isopropanol, typically from 2 to 20%, and from 0 to 5% of an alkylamine, typically 0.1% diethylamine. Concentration of the eluate affords the enriched mixture.

Mixtures of stereoisomers may be separated by conventional techniques known to those skilled in the art. [see, for example, "Stereochemistry of Organic Compounds" by E L Eliel (Wiley, New York, 1994).]

The following non-limiting examples provided below provide representative methods for preparing exemplary compounds of the present invention. The skilled practitioner will know how to substitute the appropriate reagents, starting materials and purification methods known to those skilled in the art, in order to prepare the compounds of the present invention.

$^1$H-NMR spectra were obtained on a Varian Mercury 300-MHz NMR. H Nuclear magnetic resonance (NMR) spectra were in all cases consistent with the proposed structures. Characteristic chemical shifts (5) are given in parts-per-million downfield from tetramethylsilane using conventional abbreviations for designation of major peaks: e.g. s, singlet; d, doublet; t, triplet; q, quartet; m, multiplet; br, broad. Purity (%) and mass spectral data were determined with a Waters Alliance 2695 HPLC/MS (Waters Symmetry C18, 4.6×75 mm, 3.5 µm) with a 2996 diode array detector from 210-400 nm. Retention times (RT) are reported in minutes. The mass spectra (m/z) were recorded using either electrospray ionisation (ESI) or atmospheric pressure chemical ionisation (APCI). Where thin layer chromatography (TLC) has been used it refers to silica gel TLC using silica gel 60 F$^{254}$ plates, Rf is the distance travelled by a compound divided by the distance travelled by the solvent front on a TLC plate.

EXAMPLES

Example 1: N-{3-[3-(5-Methyl-furan-2-yl)-2-(3-oxo-butyl)-benzofuran-5-yl]-phenyl}-methanesulfonamide

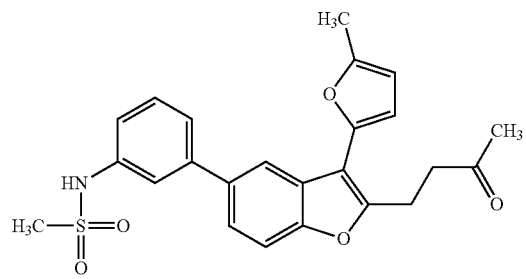 [SMILES: CC(=O)CCc1oc2ccc(-c3cccc(NS(C)(=O)=O)c3)cc2c1-c1ccc(C)o1]

A mixture of a known compound: 4-[5-bromo-3-(5-methyl-furan-2-yl)-benzofuran-2-yl]-butan-2-one (50 mg, 0.14 mmol), X-3-methanesulfonamide phenylboronic acid (31 mg, 0.14 mmol), and 2M aqueous, potassium carbonate (216 µL, 0.43 mmol) in dioxane (1 mL) was degassed with nitrogen for 20 minutes before adding tetrakis(triphenylphosphine)palladium(0) (3.3 mg, 0.003 mmol). The reaction was heated overnight at 80° C. The reaction was quenched with water and the product was extracted with ethyl acetate. The combined organic extractions were washed with brine, dried over sodium sulfate, filtered, and concentrated in vacuo. Purification by flash chromatography (12 g silica cartridge, 0-65% ethyl acetate/hexane) gave the title compound ($^1$H NMR (300 MHz, CD$_3$OD) δ 2.21 (s, 3H), 2.40 (s, 3H), 2.95-3.06 (m, 5H), 3.28 (m, 2H), 6.17-6.20 (m, 1H), 6.60 (d, J=3.2 Hz, 1H), 7.21-7.29 (m, 1H), 7.39-7.59 (m, 5H), 7.97 (dd, J=3.7 Hz, 1H). LCMS (ESI) m/z 438.2 (M+1)$^+$.

Example 2. 4-(5-(6-Methoxypyridin-3-yl)-3-(5-methylfuran-2-yl)benzofuran-2-yl)butan-2-one

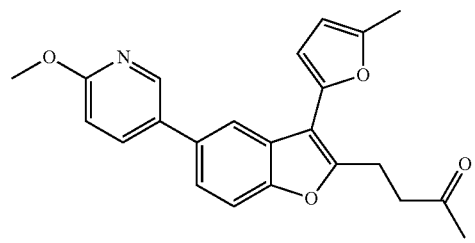 [SMILES: COc1ccc(-c2ccc3oc(CCC(C)=O)c(-c4ccc(C)o4)c3c2)cn1]

4-(5-(6-Methoxypyridin-3-yl)-3-(5-methylfuran-2-yl)benzofuran-2-yl)butan-2-one was synthesized using the same procedure as in example 1 but substituting 6-methoxypyridin-3-yl-3-boronic acid for N-3-methanesulfonamide phenylboronic acid to afford product (53 mg, 71% yield). LC/MS: RT=6.06 minutes, purity >95%, (M+H)$^+$=374.01. $^1$H NMR (300 MHz, CDCl$_3$) δ=8.41 (br. s., 1H), 7.98-7.71 (m, 2H), 7.53-7.31 (m, 2H), 6.81 (d, J=8.5 Hz, 1H), 6.49 (br. s., 1H), 6.25-5.98 (m, 1H), 4.07-3.86 (m, 3H), 3.32 (t, J=7.3 Hz, 2H), 2.94 (t, J=7.2 Hz, 2H), 2.39 (s, 3H), 2.20 (s, 3H).

Example 3. 4-(3-(5-Methylfuran-2-yl)-5-(pyridin-3-yl)benzofuran-2-yl)butan-2-one

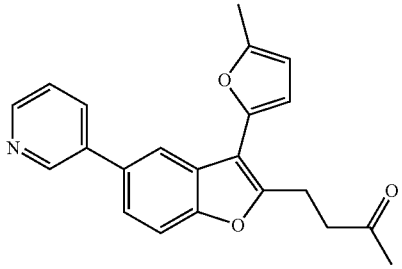 [SMILES: CC(=O)CCc1oc2ccc(-c3cccnc3)cc2c1-c1ccc(C)o1]

4-(3-(5-Methylfuran-2-yl)-5-(pyridin-3-yl)benzofuran-2-yl)butan-2-one was synthesized using the same procedure as in example 1 but substituting pyridin-3-ylboronic acid for N-3-methanesulfonamide phenylboronic acid to afford product (120 mg, 57% yield). The product was converted to an HCl salt (112 mg). LC/MS: RT=4.01 minutes, purity >95%, (M+H)$^+$=343.94. $^1$H NMR (300 MHz, CDCl$_3$) δ=8.90 (br. s., 1H), 8.59 (br. s., 1H), 8.06-7.80 (m, 2H), 7.59-7.29 (m, 3H), 6.51 (br. s., 1H), 6.27-5.96 (m, 1H), 3.32 (d, J=5.9 Hz, 2H), 2.98 (t, J=6.7 Hz, 2H), 2.50-2.32 (s, 3H), 2.30-2.11 (s, 3H).

Example 4. 4-(5-(3-Hydroxyphenyl)-3-(5-methyl-furan-2-yl)benzofuran-2-yl)butan-2-one

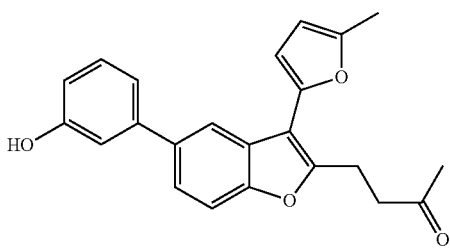 [SMILES: CC(=O)CCc1oc2ccc(-c3cccc(O)c3)cc2c1-c1ccc(C)o1]

4-(5-(3-Hydroxyphenyl)-3-(5-methylfuran-2-yl)benzofuran-2-yl)butan-2-one was synthesized using the same procedure as in example 1 but substituting 3-hydroxyphenyl boronic acid for N-3-methanesulfonamide phenylboronic acid to afford product (25 mg, 35% yield). LC/MS: RT=6.67 minutes, purity >95%, (M+H)$^+$=300.70 $^1$H NMR (300 MHz, CDCl$_3$) δ=8.00-7.87 (m, 1H), 7.55-7.38 (m, 2H), 7.36-7.23 (m, 1H), 7.20-7.09 (m, 2H), 6.83 (dd, J=2.5, 8.1 Hz, 1H), 6.51 (d, J=3.2 Hz, 1H), 6.12 (d, J=2.9 Hz, 1H), 3.33 (t, J=7.5 Hz, 2H), 3.05-2.88 (m, 2H), 2.44-2.30 (m, 3H), 2.29-2.17 (m, 3H).

Example 5. 4-(5-(3-Methoxyphenyl)-3-(5-methyl-furan-2-yl)benzofuran-2-yl)butan-2-one

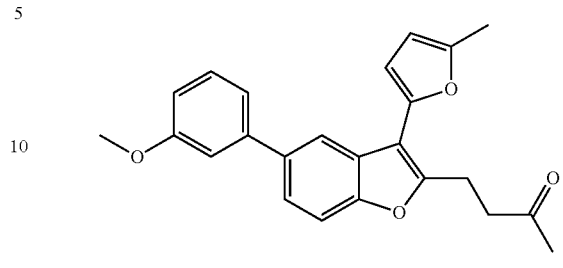

4-(5-(3-Methoxyphenyl)-3-(5-methylfuran-2-yl)benzofuran-2-yl)butan-2-one was synthesized using the same procedure as in example 1 but substituting 3-methoxyphenyl boronic acid for N-3-methanesulfonamide phenylboronic acid to afford product (51 mg, 68% yield). LC/MS: RT=6.80 min, purity >95%, (M+H)$^+$=314.75. $^1$H NMR (300 MHz, CDCl$_3$) δ=8.01-7.89 (m, 1H), 7.52-7.30 (m, 3H), 7.28-7.12 (m, 2H), 6.96-6.83 (m, 1H), 6.52 (d, J=2.9 Hz, 1H), 6.18-6.03 (m, 1H), 3.93-3.81 (m, 3H), 3.42-3.19 (m, 2H), 3.02-2.83 (m, 2H), 2.44-2.31 (m, 3H), 2.26-2.16 (m, 3H).

Example 6. 4-(3-(5-Methylfuran-2-yl)-5-(pyridin-4-yl)benzofuran-2-yl)butan-2-one hydrochloride

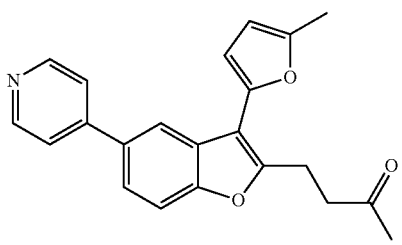 [SMILES: CC(=O)CCc1oc2ccc(-c3ccncc3)cc2c1-c1ccc(C)o1]

4-(3-(5-Methylfuran-2-yl)-5-(pyridin-4-yl)benzofuran-2-yl)butan-2-one hydrochloride was synthesized using the same procedure as in example 1 but substituting 3-methoxyphenyl boronic acid for N-3-methanesulfonamide phenylboronic acid to afford product (15 mg, 22% yield). LC/MS: RT=3.99 minutes, purity >95%, (M+H)$^+$=343.88. $^1$H NMR (300 MHz, CDCl$_3$) δ=8.61 (br. s., 2H), 8.03 (br.s., 1H), 7.69-7.44 (m, 4H), 6.71-6.41 (m, 1H), 6.16 (br. s., 1H), 3.54-3.22 (m, 2H), 3.13-2.87 (m, 3H), 2.58-2.38 (m, 3H), 2.33-2.13 (m, 3H).

Example 7. 4-(5-(2-Methoxypyridin-4-yl)-3-(5-methylfuran-2-yl)benzofuran-2-yl)butan-2-one

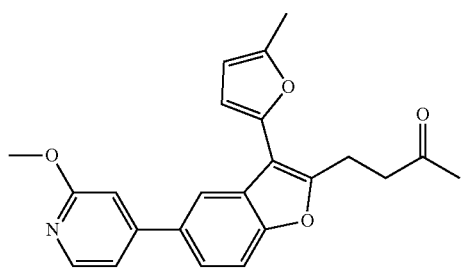 [SMILES: COc1cc(-c2ccc3oc(CCC(C)=O)c(-c4ccc(C)o4)c3c2)ccn1]

4-(5-(2-Methoxypyridin-4-yl)-3-(5-methylfuran-2-yl)benzofuran-2-yl)butan-2-one was synthesized using the same procedure as in example 1 but substituting 2-methoxypyridin-4-yl-4-boronic acid for N-3-methanesulfonamide phenylboronic acid to afford product (35 mg, 47% yield). LC/MS: RT=5.42 minutes, purity >95%, (M+H)⁺=374.01. ¹H NMR (300 MHz, CDCl₃) δ=8.37-8.13 (m, 2H), 7.99 (br.s., 1H), 7.63-7.37 (m, 2H), 7.19-7.05 (m, 1H), 7.00 (br. s, 1H), 6.62-6.42 (m, 1H), 6.26-6.01 (m, 1H), 4.00 (s, 3H), 3.33 (t, J==7.2 Hz, 2H), 3.10-2.83 (m, 2H), 2.50-2.35 (m, 3H), 2.31-2.08 (m, 3H).

Example 8. 4-(3-(5-Methylfuran-2-yl)-5-(thiophen-2-yl)benzofuran-2-yl)butan-2-one

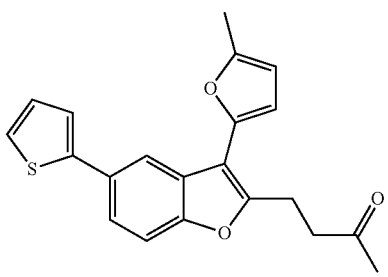 [SMILES: CC(=O)CCc1oc2ccc(-c3cccs3)cc2c1-c1ccc(C)o1]

A mixture of 4-(5-bromo-3-(5-methylfuran-2-yl)benzofuran-2-yl)butan-2-one (347 mg, 1.0 mmol), thiophen-2-boronic acid (210 mg, 1.5 mmol), palladium acetate (11 mg, 0.05 mmol), potassium phosphate (424 mg, 2.0 mmol), 2-dicyclohexylphosphinyl-2'4'6'-triisopropylbiphenyl (46 mg, 0.1 mmol) and n-butanol (2.0 mL) was heated at 100° C. for 10 hours. The mixture was worked up with water (30 mL), extracted with ethyl acetate (3×). Combined extracts were washed by brine, dried and concentrated; the residue was purified by flash column (24 g, 0-10% ethyl acetate/Hexane) to give 4-(3-(5-methylfuran-2-yl)-5-(thiophen-2-yl)benzofuran-2-yl)butan-2-one (240 mg, 69% yield). LC/MS: RT=5.82 minutes, purity >95%, ¹H NMR (300 MHz, CDCl₃) δ=7.98 (br. s., 1H), 7.58-7.47 (m, 1H), 7.45-7.33 (m, 1H), 7.28 (d, 7=9.7 Hz, 2H), 7.09 (br. s., 1H), 6.51 (br. s., 1H), 6.14 (br. s., 1H), 3.40-3.21 (m, 2H), 2.96 (t, 7=6.9 Hz, 2H), 2.41 (s, 3H), 2.21 (s, 3H).

Example 9. 4-[5-Bromo-3-(3-methyl-butyl)-benzofuran-2-yl]-butan-2-one

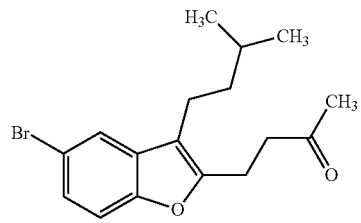 [SMILES: CC(=O)CCc1oc2ccc(Br)cc2c1CCC(C)C]

1-Bromo-3-methylbutane (1.56 mL, 12.4 mmol) was stirred with crushed magnesium turnings in diethyl ether for 15 minutes after bubbling had ceased. 5-Bromosalicylaldehyde (1.00 g, 4.98 mmol) in diethyl ether (10 mL) was added dropwise. The mixture was stirred for 5 minutes and then water (3 mL) was added slowly to decompose the excess magnesium. The insoluble material was filtered off and the filtrate was concentrated. Purification by flash chromatography (24 g silica, 0-35% EtOAc/Hexane) afforded 4-Bromo-2-(1-hydroxy-4-methyl-pentyl)-phenol as a white solid (626 mg, 46% yield). ¹H NMR (300 MHz, CD₃OD) δ 0.89 (d, 7=6.7 Hz, 6H), 1.10-1.40 (m, 2H), 1.49-1.78 (m, 3H), 4.90 (dd, J=7.6, 5.3 Hz, 1H), 6.66 (d, J=8.6 Hz, 1H), 7.15 (dd, 7=4.9 Hz, 1H), 7.38 (d, 7=2.6 Hz, 1H). LCMS (ESI) m/z 185/187 (M/M+2)⁺ fragment loss of C₅H₁₂O.

A mixture of 4-bromo-2-(1-hydroxy-4-methyl-pentyl)-phenol (620 mg, 2.27 mmol), 2-methylfuran (221 μL, 2.50 mmol), and p-toluenesulfonic acid (6 mg, 0.035 mmol) in toluene (2.3 mL) was heated at reflux for 15 minutes. The solvent was removed in vacuo and the residue was purified first by flash chromatography (12 g silica, 0-25% EtOAc/Hexane) to obtain a mixture. A portion of the mixture (55 mg) was twice purified by preparative reverse phase HPLC to afford pure 4-[5-bromo-3-(3-methyl-butyl)-benzofuran-2-yl]-butan-2-one as a white solid after freeze drying (40 mg, yield not determinable). ¹H NMR (300 MHz, CD₃OD) δ 0.97-1.00 (m, 6H), 1.45-1.67 (m, 3H), 2.15-2.17 (m, 3H), 2.59-2.67 (m, 2H), 2.87-3.02 (m, 4H), 7.28-7.30 (m, 2H), 7.57 (dd, 7=1.8, 0.9 Hz, 1H). LCMS (ESI) m/z 223/225 (M/M+2)⁺ fragment loss of C₇H₁₄O.

Example 10. 4-(5-Bromo-3-phenylbenzofuran-2-yl)butan-2-one

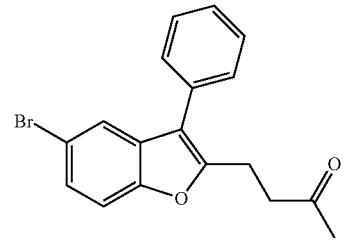 [SMILES: CC(=O)CCc1oc2ccc(Br)cc2c1-c1ccccc1]

To a solution of 5-bromo-2-hydroxybenzaldehyde (250 mg, 1.25 mmol) in tetrahydrofuran at 0° C. was added phenyl magnesium bromide (1.25 mL, 3.75 mmol). The mixture was stirred for 2 hours and then quenched with saturated aqueous ammonium chloride solution. The mixture was extracted with ethyl acetate. The organic layer was washed with brine, dried and concentrated. The residue was purified by flash column (10-40% ethyl acetate/hexanes) to give 4-bromo-2-(hydroxy(phenyl)methyl)phenol (303 mg, 87% yield). LC/MS: RT=4.61 minutes, purity >95%, (M-18)⁺=260.92

A mixture of 4-bromo-2-(hydroxy(phenyl)methyl)phenol (84 mg, 0.3 mmol), 2-methyl furan (34 uL, 0.39 mmol) and 4-methylbenzenesulfonic acid (5 mg) in toluene (2 mL) was heated at 120° C. for 2 hour and then concentrated. The residue was purified on flash column to give the title compound (80 mg, 78% yield). LC/MS: RT=6.64 minutes, purity >95%, (M)⁺=342.24. ¹H NMR (300 MHz, CDCl₃) δ=7.70-7.62 (m, 1H), 7.55-7.44 (m, 4H), 7.43-7.22 (m, 3H), 3.20-3.09 (m, 2H), 2.98-2.83 (m, 2H), 2.20-2.11 (m, 3H)

Example 11. 4-(5-Bromo-3-p-tolylbenzofuran-2-yl)butan-2-one

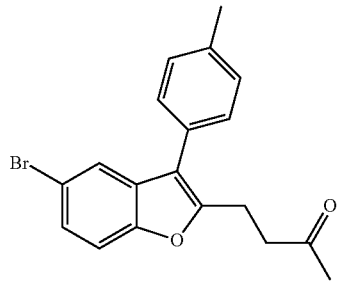 [SMILES: CC(=O)CCc1oc2ccc(Br)cc2c1-c1ccc(C)cc1]

4-(5-Bromo-3-p-tolylbenzofuran-2-yl)butan-2-one was synthesized using the same procedure as in example 11 but substituting phenyl magnesium bromide for 4-methylphenyl magnesium bromide to give the product (54 mg, 61% yield). LC/MS: RT=6.78 minutes, purity >95%, $^1$H NMR (300 MHz, CDCl$_3$) δ=7.64 (d, 7=1.5 Hz, 1H), 7.42-7.20 (m, 7H), 3.21-3.05 (m, 2H), 2.97-2.77 (m, 2H), 2.46-2.36 (m, 3H), 2.21-2.12 (m, 3H)

Example 12. 3-[5-Bromo-3-(5-methyl-furan-2-yl)-benzofuran-2-yl]-propionic Acid

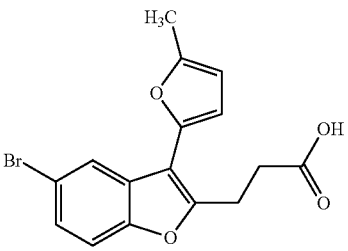 [SMILES: Cc1ccc(-c2c(CCC(=O)O)oc3ccc(Br)cc23)o1]

Bromine (1.15 mL, 22.5 mmol) was added dropwise with stirring and cooling to a solution of sodium hydroxide (3.80 g, 95.0 mmol) in water (8.65 mL). A solution of a known compound: 4-[5-bromo-3-(5-methyl-furan-2-yl)-benzofuran-2-yl]-butan-2-one (1.00 g, 2.88 mmol) in dioxane (4 mL) was added to the in situ generated sodium hypobromite in solution with stirring at room temperature. The reaction was stirred for 5 hours, and then water (57 mL) was added. The water was extracted with diethyl ether (5×15 mL). To the aqueous layer acetic acid (5.77 mL) was added carefully and the mixture was stirred over the weekend. The aqueous layer was then extracted with CH$_2$Cl$_2$ (3×15 mL). The combined organic extractions were washed with brine, dried over sodium sulfate, filtered, and concentrated in vacuo. Purification by preparative reverse phase HPLC gave the title compound as a yellow solid (60 mg, 6% yield), $^1$H NMR (300 MHz, CD$_3$OD) δ 2.40 (d, 7=0.9 Hz, 3H), 2.75-2.82 (m, 2H), 3.33-3.38 (m, 2H), 6.18 (d, 7=3.2 Hz, 1H), 6.58 (d, 7=3.2 Hz, 1H), 7.32-7.48 (m, 2H), 7.92 (s, 1H). LCMS (ESI) m/z 349/351 (M+1)$^+$.

Example 13. 3-[5-Bromo-3-(5-methyl-furan-2-yl)-benzofuran-2-yl]-1-(4-hydroxy-piperidin-1-yl)-propan-1-one

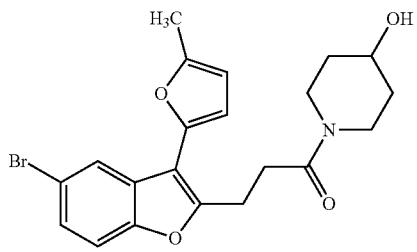 [SMILES: Cc1ccc(-c2c(CCC(=O)N3CCC(O)CC3)oc3ccc(Br)cc23)o1]

A mixture of 3-[5-bromo-3-(5-methyl-furan-2-yl)-benzofuran-2-yl]-propionic acid (20 mg, 0.058 mmol), 4-hydroxypiperidine (13.8 mg, 0.136 mmol), and (1-[bis(dimethylamino)methylene]-1H-1,2,3-triazolo[4,5-b]pyridinium 3-oxide hexafluoro phosphate) (66 mg, 0.173 mmol) in dimethylformamide (288 μL) was stirred 1 hour at room temperature. The reaction was purified by reverse phase HPLC to obtain a yellow solid after freeze drying (21 mg, 84% yield). $^1$H NMR (300 MHz, CD$_3$OD) δ 1.28-1.51 (m, 2H), 1.60-1.85 (m, 2H), 2.38-2.41 (m, 3H), 2.84-2.95 (m, 2H), 3.08-3.29 (m, 2H), 3.33-3.39 (m, 2H), 3.79 (m, 2H), 4.01 (s, 1H), 6.18 (d, 7=3.2 Hz, 1H), 6.58 (d, 7=3.2 Hz, 1H), 7.36-7.44 (m, 2H), 7.92 (dd, 7=1.8, 0.9 Hz, 1H). LCMS (ESI) m/z 432/434 (M+1)$^+$.

Example 14. 2-{2-[5-Bromo-3-(5-methyl-furan-2-yl)-benzofuran-2-yl]-ethyl}-1H-benzoimidazole

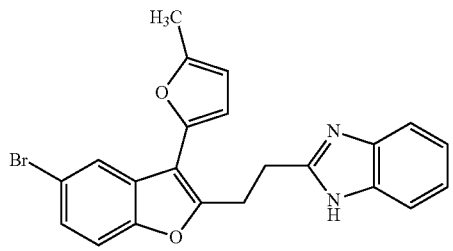 [SMILES: Cc1ccc(-c2c(CCc3nc4ccccc4[nH]3)oc3ccc(Br)cc23)o1]

3-[5-Bromo-3-(5-methyl-furan-2-yl)-benzofuran-2-yl]-propionic acid (16.5 mg, 0.048 mmol, o-phenylenediamine (5.1 mg, 0.048 mmol), and triphenylphosphite (16 μL, 0.062 mmol) in dry pyridine (700 μL) was heated in the microwave at 180° C. for 10 minutes. The reaction was purified directly by reverse phase HPLC to obtain a pale yellow powder after freeze drying (19 mg, 75% yield, TFA (trifluoracetic acid) salt). $^1$H NMR (300 MHz, CD$_3$OD) δ 2.22 (d, 7=0.9 Hz, 3H), 3.53-3.74 (m, 4H), 6.00-6.03 (m, 1H), 6.50 (d, 7=3.2 Hz, 1H), 7.31-7.39 (m, 1H), 7.43-7.56 (m, 3H), 7.62-7.68 (m, 2H), 7.87 (d, 7=1.8 Hz, 1H). LCMS (ESI) m/z 432/434 (M/M+2)$^+$.

Example 15. 4-(5-Bromo-3-(5-methylfuran-2-yl)benzofuran-2-yl)-2-methylbutan-2-ol

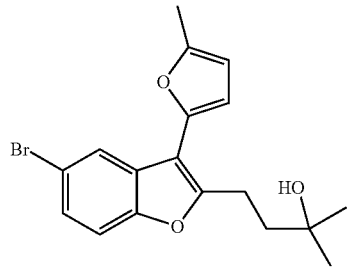 [SMILES: Cc1ccc(-c2c(CCC(C)(C)O)oc3ccc(Br)cc23)o1]

To a solution of 4-(5-bromo-3-(5-methylfuran-2-yl)benzofuran-2-yl)butan-2-one (50 mg, 0.144 mmol) in tetrahydrofuran (2 mL) at 0° C. was added methyl magnesium bromide (0.1 mL, 0.3 mmol) The mixture was stirred for 2 hours and then treated with saturated ammonium chloride solution. The organic layer was separated, washed with brine, dried, and concentrated. The residue was purified by flash column (10-30% ethyl acetate/hexanes) to give the desired compound (29 mg, 56% yield). LC/MS: RT=6.50 minutes, purity >95%, (M-18)$^+$=344.89. $^1$H NMR (300 MHz, CDCl$_3$) δ=7.97-7.82 (m, 1H), 7.41-7.21 (m, 2H), 6.51-6.38 (m, 1H), 6.19-6.06 (m, 1H), 3.20-2.98 (m, 2H), 2.40 (s, 3H), 2.06-1.88 (m, 2H), 1.35-1.24 (m, 7H)

Example 16. 4-(5-Bromo-3-(5-methylfuran-2-yl)benzofuran-2-yl)-2-p-tolylbutane-2-ol

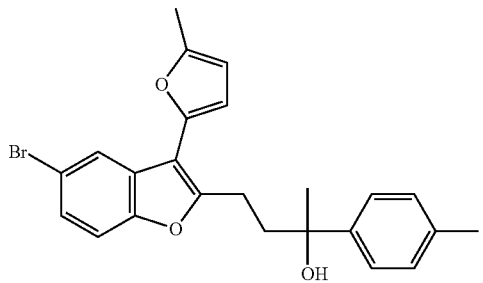 [SMILES: Cc1ccc(C(C)(O)CCc2oc3ccc(Br)cc3c2-c2ccc(C)o2)cc1]

4-(5-Bromo-3-(5-methylfuran-2-yl)benzofuran-2-yl)-2-p-tolylbutane-2-ol was synthesized using the same procedure as in example 15 but substituting 4-methylphenyl magnesium bromide (1.0 mL, 0.5 mmol) for methyl magnesium bromide to give the product (20 mg, 32% yield). LC/MS: R$_f$=7.26 minutes, purity >95%, (M-18)$^+$=420.90. $^1$H NMR (300 MHz, CDCl$_3$) δ=7.87 (d, J=1.5 Hz, 1H), 7.38-7.29 (m, 3H), 7.27-7.19 (m, 1H), 7.17-7.07 (m, 2H), 6.28 (d, J=3.2 Hz, 1H), 6.09-6.01 (m, 1H), 3.10-2.96 (m, 2H), 2.95-2.76 (m, 2H), 2.35 (s, 6H), 1.67-1.56 (m, 3H).

Example 17. 4-(5-Bromo-3-(5-chlorothiophen-2-yl)benzofuran-2-yl)butan-2-one

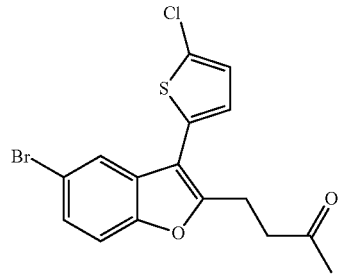 [SMILES: CC(=O)CCc1oc2ccc(Br)cc2c1-c1ccc(Cl)s1]

4-(5-Bromo-3-(5-chlorothiophen-2-yl)benzofuran-2-yl)butan-2-one was synthesized using the same procedure as in example 10 but substituting 5-chloro-2-thienyl magnesium chloride for phenyl magnesium bromide to give the product (204 mg, 74% yield). LC/MS: RT=6.95 minutes, purity >95%, (M+1)$^+$=382.88. $^1$H NMR (300 MHz, CDCl$_3$) δ=7.74 (d, J=1.8 Hz, 1H), 7.43-7.24 (m, 2H), 7.03-6.86 (m, 2H), 3.25-3.14 (m, 2H), 3.01-2.87 (m, 2H), 2.24-2.14 (m, 3H)

Example 18. 4-(3-(5-Chlorothiophen-2-yl)-5-(pyridin-4-yl)benzofuran-2-yl)butan-2-one

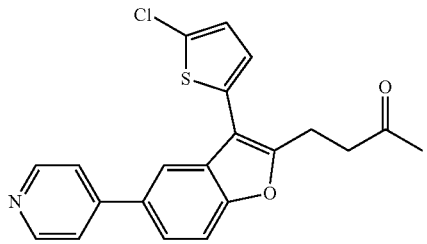 [SMILES: CC(=O)CCc1oc2ccc(-c3ccncc3)cc2c1-c1ccc(Cl)s1]

To a mixture of previous made 4-(5-bromo-3-(5-chlorothiophen-2-yl)benzofuran-2-yl)butan-2-one (70 mg, 0.183 mmol) and 4-pyridyl boronic acid (30 mg, 0.24 mmol) and tetrakis (triphenylphosphine)palladium (0) (10 mg, 0.008 mmol) was added 2N potassium carbonate solution (0.5 mL) and dioxane (2 mL). The mixture was heated at 80° C. for 5 hours. Ethyl acetate (10 mL) and water (10 mL) was added and filtered, extracted with ethyl acetate (2×). Combined extracts were dried and concentrated. The residue was purified by flash column (12 g) to give the desired product (10 mg, 14% yield). LC/MS: RT=4.39 minutes, purity >95%, (M+H)$^+$=381.85. $^1$H NMR (300 MHz, CDCl$_3$) δ=8.66 (br. s., 1H), 7.95-7.82 (m, 1H), 7.64-7.46 (m, 2H), 7.07-6.96 (m, 1H), 3.33-3.19 (m, 1H), 3.04-2.87 (m, 1H), 2.21 (s, 2H)

Example 19. 4-(3-(5-chlorothiophen-2-yl)-5-(2-methoxypyridin-4-yl)benzofuran-2-yl)butan-2-one

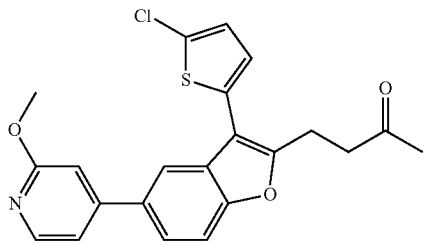 [SMILES: COc1cc(-c2ccc3oc(CCC(C)=O)c(-c4ccc(Cl)s4)c3c2)ccn1]

4-(3-(5-chlorothiophen-2-yl)-5-(2-methoxypyridin-4-yl)benzofuran-2-yl)butan-2-one was synthesized using the same procedure as in example 18 but substituting 2-methoxypyridin-4-yl-4-boronic acid for 4-pyridyl boronic acid to give the product (48 mg, 64% yield). LC/MS: RT=5.80 minutes, purity >95%, (M+H)$^+$=411.88. $^1$H NMR (300 MHz, CDCl$_3$) δ=8.21 (d, J=5.3 Hz, 1H), 7.86 (d, J=0.9 Hz, 1H), 7.60-7.45 (m, 2H), 7.13 (d, J=5.3 Hz, 4H), 3.99 (s, 3H), 3.30-3.14 (m, 2H), 3.03-2.86 (m, 2H), 2.21 (s, 3H)

Example 20. 4-(5-(6-Chloropyridin-3-yl)-3-(5-chlorothiophen-2-yl)benzofuran-2-yl)butan-2-one

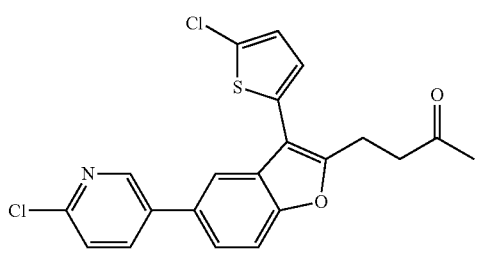 [SMILES: CC(=O)CCc1oc2ccc(-c3ccc(Cl)nc3)cc2c1-c1ccc(Cl)s1]

4-(5-(6-Chloropyridin-3-yl)-3-(5-chlorothiophen-2-yl)benzofuran-2-yl)butan-2-one was synthesized using the same procedure as in example 18 but substituting 6-chloropyridyl-3-boronic acid for 4-pyridyl boronic acid to give the product (23 mg, 30% yield). LC/MS: RT=6.69 minutes, purity 95%, (M+H)$^+$=415.83. $^1$H NMR (300 MHz, CDCl$_3$) δ=8.69-8.53 (m, 1H), 7.94-7.70 (m, 2H), 7.61-7.34 (m, 3H), 7.09-6.93 (m, 2H), 3.33-3.16 (m, 2H), 3.05-2.89 (m, 2H), 2.27-2.14 (m, 3H)

Example 21. 4-(6-Bromo-3-(5-methylfuran-2-yl)benzofuran-2-yl)butan-2-one

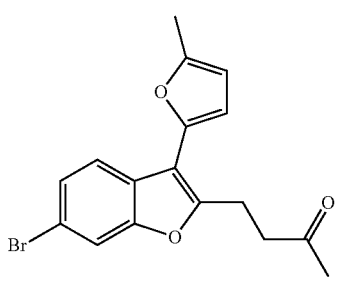 [SMILES: CC(=O)CCc1oc2cc(Br)ccc2c1-c1ccc(C)o1]

To a mixture of 4-bromo-2-hydroxybenzaldehyde (1.0 g, 5.0 mmol) and 2-methyl furan (l. 1 mL, 12.5 mmol) in ethanol (4 mL) was added saturated HCl in ethanol (4 mL) the mixture was stirred for 20 minutes, then 6 mL of saturated HCl in ethanol was added and the mixture was heated for 1 hour at refluxing. The mixture was concentrated and purified by flash column (80 g) to give the desired product (997 mg, 57%). LC/MS: RT=6.48 minutes, purity >95%, (M+H)$^+$=346.83.

Example 22. 4-(3-(5-Methylfuran-2-yl)-6-(pyridin-4-yl)benzofuran-2-yl)butan-2-one

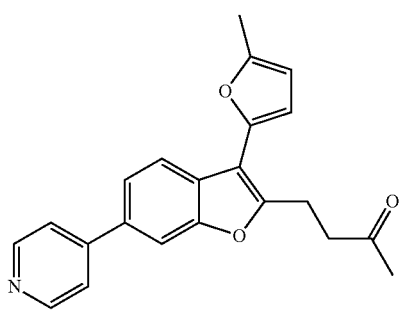 [SMILES: CC(=O)CCc1oc2cc(-c3ccncc3)ccc2c1-c1ccc(C)o1]

A mixture of 4-(6-bromo-3-(5-methylfuran-2-yl)benzofuran-2-yl)butan-2-one (210 mg, 0.61 mmol), pyridin-4-yl-4-boronic acid (97 mg, 0.8 mmol), tetrakis (triphenylphosphine)palladium (0) (35 mg, 0.03 mmol), 2N potassium carbonate (0.5 mL) and dioxane (1.0 mL) was stirred at 110° C. for 20 minutes in microwave instrument. The mixture was diluted with water, extracted with ethyl acetate. Combined extracts were washed with brine, dried and concentrated; the residue was purified by flash column (20 g) to give the title compound (99 mg, 47% yield). LC/MS: RT=4.16 minutes, purity >95%, (M+H)$^+$=345.98. $^1$H NMR (300 MHz, CDCl$_3$) δ=8.66 (d, 7=5.9 Hz, 1H), 7.97-7.81 (m, 1H), 7.68 (d, 7=1.2 Hz, 1H), 7.63-7.45 (m, 2H), 6.51 (d, 7=2.9 Hz, 1H), 6.14 (d, 7=2.3 Hz, 1H), 3.35 (t, 7=7.6 Hz, 1H), 3.04-2.89 (m, 1H), 2.48-2.34 (m, 1H), 2.30-2.15 (m, 1H)

Example 23. 4-(6-(2-Methoxypyridin-4-yl)-3-(5-methylfuran-2-yl)benzo furan-2-yl)butan-2-one

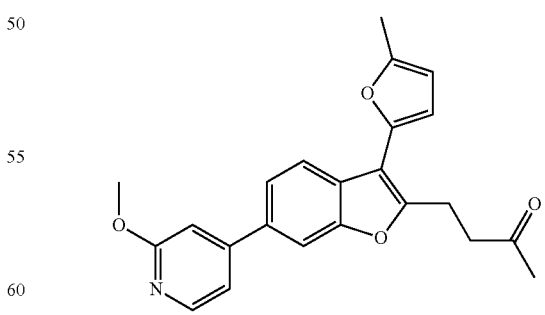

4-(6-(2-Methoxypyridin-4-yl)-3-(5-methylfuran-2-yl)benzofuran-2-yl)butan-2-one was synthesized using the same procedure as in example 22 but substituting 2-methoxypyridyl-4-boronic acid for 4-pyridyl boronic acid to give the product free base (109 mg, 47% yield). This product was dissolved in ethyl acetate (5 mL) and 4N HCl in dioxane 75 uL was added. The mixture was stirred for 20 minutes, filtered, washed by ethyl acetate and dried to give 92 mg HCl salt. LC/MS: RT=6.23 minutes, purity >95%, (M+H)$^+$=374.01. $^1$H NMR (300 MHz, CDCl$_3$) δ=8.43 (br. S., 1H), 7.84 (t, J=98.2 Hz, 2H), 7.56 (br. s., 1H), 7.44 (d, J=8.5 Hz, 1H), 7.26 (br. S., 3H), 6.84 (d, J=8.5 Hz, 1H), 6.51 (br. S., 1H), 6.13 (br. s., 1H), 4.00 (br. s., 3H), 3.33 (d, J=8.2 Hz, 2H), 3.06-2.87 (m, 2H), 2.41 (s, 3H), 2.22 (br. s., 3H).

Example 24. 4-(3-(5-methylfuran-2-yl)-6-(pyridin-3-yl)benzofuran-2-yl)butan-2-one

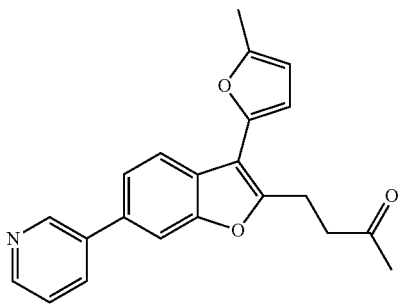

4-(3-(5-methylfuran-2-yl)-6-(pyridin-3-yl)benzofuran-2-yl)butan-2-one was synthesized using the same procedure as in example 22 but substituting 3-pyridyl boronic acid for 4-pyridyl boronic acid to afford the product (140 mg, free base, 66% yield). LC/MS: RT=4.14 minutes, purity >95%, (M+H)$^+$=343.94. $^1$H NMR (300 MHz, CDCl$_3$) δ=8.91 (br. S., 1H), 8.60 (br. S., 1H), 7.90 (t, J=9.8 Hz, 2H), 7.62 (s, 1H), 7.50 (d, J=7.9 Hz, 1H), 7.38 (br. S., 1H), 6.52 (br. S., 1H), 6.14 (br. S., 1H), 3.35 (t, J=7.5 Hz, 2H), 3.06-2.85 (m, 2H), 2.41 (s, 3H), 2.30-2.15 (m, 3H).

Example 25. 4-(5-Bromo-3-(p-tolylmethyl)benzofuran-2-yl)butan-2-one

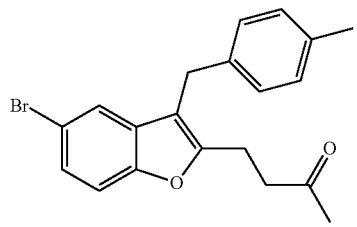 [SMILES: CC(=O)CCc1oc2ccc(Br)cc2c1Cc1ccc(C)cc1]

To a solution of 5-bromo-2-hydroxybenzaldehyde (250 mg, 1.25 mmol) in tetrahydrofuran (5 mL) was added 4-methylbenzyl magnesium bromide (6.2 mL, 3.13 mmol, 0.5N solution in diethyl ether). The mixture was stirred for 1 hour, then treated with 1N HCl solution (10 mL), extracted with ethyl acetate (2×30 mL). The combined extracts were washed with brine, dried and concentrated. The residue was purified by flash column (24 g silica: 5-15% ethyl acetate/hexanes) to yield 4-bromo-2-(1-hydroxy-2-p-tolylethyl)phenol (235 mg, 61%). LC/MS: RT=5.42 minutes, purity >95%. A mixture of 4-bromo-2-(1-hydroxy-2-p-tolylethyl)phenol (60 mg, 0.20 mmol), 2-methyl furan (23 uL, 0.26 mmol), 4-methylbenzenesulfonic acid (5 mg) in toluene (2 mL) was heated at reflux for 0.5 hours. The mixture was cooled down and concentrated. The residue was purified by flash column (12 g, 0-20% ethyl acetate/hexanes) to yield 4-(5-Bromo-3-(p-tolylmethyl)benzofuran-2-yl)butan-2-one (40 mg, 54%). LC/MS: RT=6.93 minutes, purity >95%, (M+H)$^+$=371.45. $^1$H NMR (300 MHz, CDCl$_3$) δ=7.47-7.33 (m, 1H), 7.31-7.14 (m, 2H), 7.14-6.94 (m, 4H), 4.03-3.77 (m, 2H), 3.10-2.92 (m, 2H), 2.91-2.77 (m, 2H), 2.38-2.21 (m, 3H), 2.21-2.00 (m, 3H)

Example 26. 4-(5-Bromo-3-(2-p-tolylethyl)benzofuran-2-yl)butan-2-one

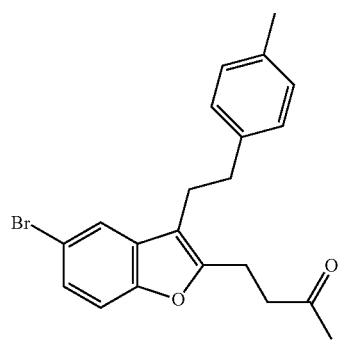 [SMILES: CC(=O)CCc1oc2ccc(Br)cc2c1CCc1ccc(C)cc1]

4-(5-Bromo-3-(2-p-tolylethyl)benzofuran-2-yl)butan-2-one was synthesized using the same procedure as in example 25 but substituting 4-methylphenylethyl magnesium bromide for 4-methylbenzyl magnesium bromide to give the product (60 mg, 81%). LC/MS: RT=7.17 minutes, purity >95%, (M+H)$^+$=384.54. $^1$H NMR (300 MHz, CDCl$_3$) δ=7.59-7.41 (m, 1H), 7.37-7.16 (m, 2H), 7.12-6.84 (m, 4H), 2.95-2.77 (m, 4H), 2.75-2.63 (m, 2H), 2.51-2.36 (m, 2H), 2.37-2.22 (m, 3H), 2.13-1.96 (m, 3H).

Example 27. 4-(5-Bromo-3-(2-phenethyl)benzofuran-2-yl)butan-2-one

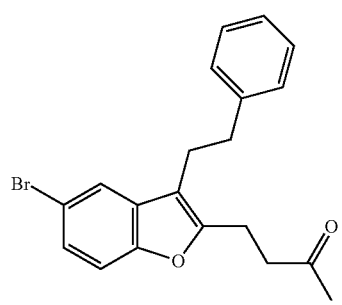 [SMILES: CC(=O)CCc1oc2ccc(Br)cc2c1CCc1ccccc1]

4-(5-Bromo-3-(2-phenethyl)benzofuran-2-yl)butan-2-one was synthesized using the same procedure as in example 25 but substituting phenylethyl magnesium bromide for 4-methylbenzyl magnesium bromide to give the product (30 mg, 40%). LC/MS: RT=6.87 minutes, purity >95%, (M+H)$^+$=370.45. $^1$H NMR (300 MHz, CDCl$_3$) δ=7.61-7.48 (m, 1H), 7.37-7.14 (m, 5H), 7.12-7.00 (m, 2H), 3.02-2.81 (m, 4H), 2.76-2.58 (m, 2H), 2.49-2.30 (m, 2H), 2.18-1.97 (m, 3H).

Example 28: 4-(6-(6-Methoxypyridin-3-yl)-3-(5-methylfuran-2-yl)benzofuran-2-yl)butan-2-one

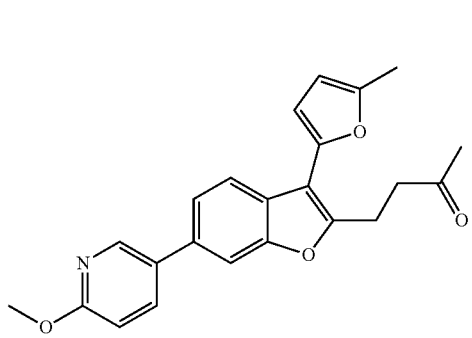 [SMILES: COc1ccc(-c2ccc3c(-c4ccc(C)o4)c(CCC(C)=O)oc3c2)cn1]

Example 28: 4-(6-(6-Methoxypyridin-3-yl)-3-(5-methylfuran-2-yl)benzofuran-2-yl)butan-2-one was synthesized using the same procedure as in example 22 but substituting 6-methoxypyridin-3-yl-3-boronic acid for 4-pyridyl boronic acid to afford the product (29 mg, free base, 48% yield). LC/MS: RT=6.23 minutes, purity >95%, (M)+=375.04. $^1$H NMR (300 MHz, CDCl$_3$) δ=8.43 (br. s., 1H), 7.84 (d, 7=8.2 Hz, 2H), 7.56 (br. s., 1H), 7.44 (d, 7=8.5 Hz, 1H), 6.84 (d, 7=8.5 Hz, 1H), 6.51 (br. s., 1H), 6.13 (br. s, 1H), 4.00 (br. s., 3H), 3.33 (d, 7=8.2 Hz, 2H), 3.01-2.93 (m, 2H), 2.41 (br. s., 3H), 2.22 (br. s., 3H).

Example 29: 4-(5-(pyrimidin-5-yl)-3-p-tolylbenzofuran-2-yl)butan-2-one, di HCl Salt

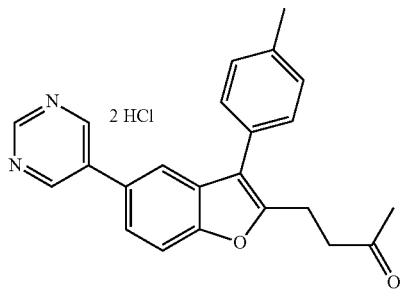 [SMILES: CC(=O)CCc1oc2ccc(-c3cncnc3)cc2c1-c1ccc(C)cc1]

Example 29: 4-(5-(pyrimidin-5-yl)-3-p-tolylbenzofuran-2-yl)butan-2-one, di HCl salt as above from 4-(5-bromo-3-p-tolylbenzofuran-2-yl)butan-2-one (90 mg, 0.25 mmol) and pyrimidin-5-yl-5-boronic acid (63 mg, 0.5 mmol) to yield the titled product (46 mg, 51% yield). The 2HCl salt was sequentially made (44 mg). LC/MS: RT=5.48 minutes, purity >95%, $^1$H NMR (300 MHz, CDCl$_3$) δ 9.08-9.25 (m, 1H), 8.78-9.02 (m, 2H), 7.70 (d, 7=1.76 Hz, 1H), 7.49-7.62 (m, 1H), 7.39-7.49 (m, 3H), 7.26-7.33 (m, 1H), 3.11-3.32 (m, 2H), 2.86-3.04 (m, 2H), 2.44 (s, 3H), 2.11-2.24 (m, 3H).

Example 30: 4-(3-(5-methylfuran-2-yl)-6-(pyrimidin-5-yl)benzofuran-2-yl)butan-2-one, di HCl Salt

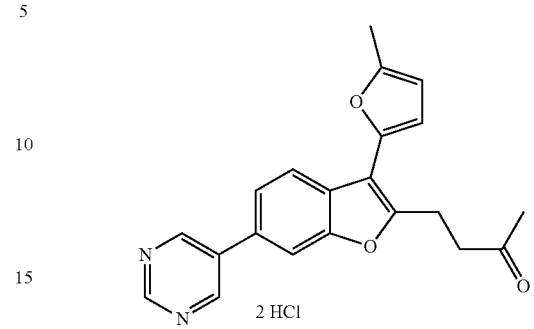

Example 30: 4-(3-(5-methylfuran-2-yl)-6-(pyrimidin-5-yl)benzofuran-2-yl)butan-2-one, di HCl salt was synthesized as above from 4-(6-bromo-3-(5-methylfuran-2-yl)benzofuran-2-yl)butan-2-one (90 mg, 0.26 mmol) and pyrimidin-5-yl-5-boronic acid (64 mg, 0.52 mmol), to yield the titled product (31 mg, 34% yield). The 2HCl salt was sequentially made (30 mg). LC/MS: RT=5.38 minutes, purity >95%, (M+H)+=347.17. $^1$H NMR (300 MHz, CDCl$_3$) δ 9.16-9.35 (m, 1H), 9.02-9.16 (m, 2H), 7.80-8.03 (m, 1H), 7.64 (d, J=0.88 Hz, 1H), 7.49 (dd, 7=1.17, 8.21 Hz, 1H), 6.42-6.58 (m, 1H), 6.04-6.20 (m, 1H), 3.20-3.43 (m, 2H), 2.86-3.14 (m, 2H), 2.41 (s, 3H), 2.15-2.32 (m, 3H).

Example 31: 4-(3-(4-fluorophenyl)-6-(pyridin-3-yl)benzofuran-2-yl)butan-2-one HCl Salt

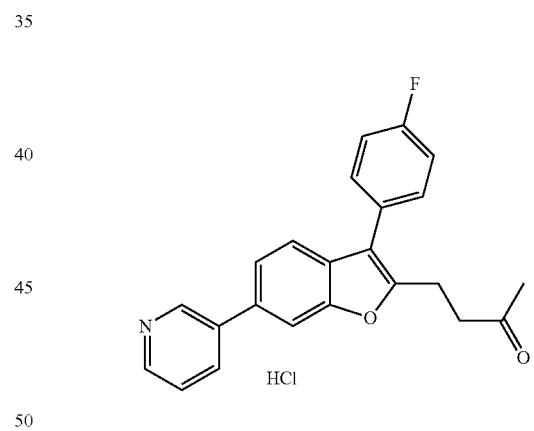

Example 31: 4-(3-(4-fluorophenyl)-6-(pyridin-3-yl)benzofuran-2-yl)butan-2-one HCl salt was synthesized as above from 4-(6-bromo-3-(4-fluorophenyl)benzofuran-2-yl)butan-2-one (54 mg, 0.15 mmol) and 3-pyridyl-boronic acid (37 mg, 0.30 mmol to yield the titled product (39 mg, 72% yield). The HCl salt was sequentially made (32 mg). LC/MS: RT=3.66 minutes, purity >95%, (M+H)+=360.08. $^1$H NMR (300 MHz, CDCl$_3$) δ 8.78-8.97 (m, 1H), 8.51-8.64 (m, 1H), 7.91 (td, 7=1.91, 7.92 Hz, 1H), 7.66 (d, 7=0.88 Hz, 1H), 7.55-7.62 (m, 1H), 7.42-7.55 (m, 3H), 7.33-7.42 (m, 1H), 7.11-7.28 (m, 3H), 3.07-3.25 (m, 2H), 2.88-3.04 (m, 2H), 2.12-2.24 (m, 3H).

Formulations

The present invention also relates to compositions or formulations which comprise the inhibitors of tau oligomer formation according to the present invention. In general, the compositions of the present invention comprise an effective amount of one or more inhibitors of tau oligomer formation of the disclosure and salts thereof according to the present invention which are effective for preventing tau oligomerization; and one or more excipients.

For the purposes of the present invention the term "excipient" and "carrier" are used interchangeably throughout the description of the present invention and said terms are defined herein as, "ingredients which are used in the practice of formulating a safe and effective pharmaceutical composition."

The formulator will understand that excipients are used primarily to serve in delivering a safe, stable, and functional pharmaceutical, serving not only as part of the overall vehicle for delivery but also as a means for achieving effective absorption by the recipient of the active ingredient. An excipient may fill a role as simple and direct as being an inert filler, or an excipient as used herein may be part of a pH stabilizing system or coating to insure delivery of the ingredients safely to the stomach. The formulator can also take advantage of the fact the compounds of the present invention have improved cellular potency, pharmacokinetic properties, as well as improved oral bioavailability.

The present teachings also provide pharmaceutical compositions that include at least one compound described herein and one or more pharmaceutically acceptable carriers, excipients, or diluents. Examples of such carriers are well known to those skilled in the art and can be prepared in accordance with acceptable pharmaceutical procedures, such as, for example, those described in *Remington's Pharmaceutical Sciences,* 17th edition, ed. Alfonoso R. Gennaro, Mack Publishing Company, Easton, Pa. (1985), the entire disclosure of which is incorporated by reference herein for all purposes. As used herein, "pharmaceutically acceptable" refers to a substance that is acceptable for use in pharmaceutical applications from a toxicological perspective and does not adversely interact with the active ingredient. Accordingly, pharmaceutically acceptable carriers are those that are compatible with the other ingredients in the formulation and are biologically acceptable. Supplementary active ingredients can also be incorporated into the pharmaceutical compositions.

Compounds of the invention may, for example, be in a form suitable for oral administration as a tablet, capsule, pill, powder, sustained release formulations, solution, suspension, for parenteral injection as a sterile solution, suspension or emulsion, for topical administration as an ointment or cream or for rectal administration as a suppository. The pharmaceutical composition may be in unit dosage forms suitable for single administration of precise dosages.

Compounds of the invention intended for pharmaceutical use may be administered as crystalline or amorphous products. They may be obtained, for example, as solid plugs, powders, or films by methods such as precipitation, crystallization, freeze drying, spray drying, or evaporative drying. Microwave or radio frequency drying may be used for this purpose.

The compounds of the invention intended for pharmaceutical use may be administered alone or in combination with one or more other compounds of the invention or in combination with one or more other drugs (or as any combination thereof). The pharmaceutical composition will include a conventional pharmaceutical carrier or excipient and a compound according to the invention as an active ingredient. In addition, it may include other medicinal or pharmaceutical agents, earners, adjuvants, etc. Generally, they will be administered as a formulation in association with one or more pharmaceutically acceptable excipients. The term "excipient" is used herein to describe any ingredient other than the compound(s) of the invention. The choice of excipient will to a large extent depend on factors such as the particular mode of administration, the effect of the excipient on solubility and stability, and the nature of the dosage form. Descriptions of pharmaceutical compositions and methods for their preparation may be found, for example, in 'Remington's Pharmaceutical Sciences', 19th Edition (Mack Publishing Company, 1995).]

Compounds of the present teachings can be administered orally or parenterally, neat or in combination with conventional pharmaceutical carriers. Applicable solid carriers can include one or more substances which can also act as flavoring agents, lubricants, solubilizers, suspending agents, fillers, glidants, compression aids, binders or tablet-disintegrating agents, or encapsulating materials. The compounds can be formulated in conventional manner, for example, in a manner similar to that used for known therapies for the treatment of central nervous system disorders. Oral formulations containing a compound disclosed herein can comprise any conventionally used oral form, including tablets, capsules containing particulates, buccal forms, troches, lozenges (including liquid-filled), gels, powders, solid solutions, multi- and nano-particulates, liposome, films (including muco-adhesive), ovules, sprays, and oral liquids, suspensions or solutions. In powders, the carrier can be a finely divided solid, which is an admixture with a finely divided compound. In tablets, a compound disclosed herein can be mixed with a carrier having the necessary compression properties in suitable proportions and compacted in the shape and size desired. The powders and tablets can contain up to 99% of the compound.

Liquid formulations include suspensions, solutions, syrups and elixirs. Such formulations may be employed as fillers in soft or hard capsules and typically comprise a carrier, for example, water, ethanol, polyethylene glycol, propylene glycol, methylcellulose, or a suitable oil, and one or more emulsifying agents and/or suspending agents. Liquid formulations may also be prepared by the reconstitution of a solid, for example, from a sachet. The compounds of the invention may also be used in fast-dissolving, fast-disintegrating dosage forms such as those described in Expert Opinion in Therapeutic Patents, 11 (6), 981-986 by Liang and Chen (2001).

Capsules can contain mixtures of one or more compound(s) disclosed herein with inert filler(s) and/or diluent(s) such as pharmaceutically acceptable starches (e.g., corn, potato or tapioca starch), sugars, artificial sweetening agents, powdered celluloses (e.g., crystalline and microcrystalline celluloses), flours, gelatins, gums, and the like.

Useful tablet formulations can be made by conventional compression, wet granulation or dry granulation methods and utilize pharmaceutically acceptable diluents, binding agents, lubricants, disintegrants, surface modifying agents (including surfactants), suspending or stabilizing agents, including, but not limited to, magnesium stearate, stearic acid, sodium lauryl sulfate, talc, sugars, lactose, dextrin, starch, gelatin, cellulose, methyl cellulose, microcrystalline cellulose, sodium carboxymethyl cellulose, carboxymethylcellulose calcium, polyvinylpyrrolidine, alginic acid, acacia gum, xanthan gum, sodium citrate, complex silicates, calcium carbonate, glycine, sucrose, sorbitol, dicalcium phosphate, calcium sulfate, lactose, kaolin, mannitol, sodium chloride, low melting waxes, and ion exchange resins.

Surface modifying agents include nonionic and anionic surface modifying agents. Representative examples of surface modifying agents include, but are not limited to, poloxamer 188, benzalkonium chloride, calcium stearate, cetostearl alcohol, cetomacrogol emulsifying wax, sorbitan esters, colloidal silicon dioxide, phosphates, sodium dodecylsulfate, magnesium aluminum silicate, and triethanolamine. Oral formulations herein can utilize standard delay or time-release formulations to alter the absorption of the compound(s). The oral formulation can also consist of administering a compound disclosed herein in water or fruit juice, containing appropriate solubilizers or emulsifiers as needed.

Liquid carriers can be used in preparing solutions, suspensions, emulsions, syrups, elixirs, and for inhaled delivery. A compound of the present teachings can be dissolved or suspended in a pharmaceutically acceptable liquid carrier such as water, an organic solvent, or a mixture of both, or a pharmaceutically acceptable oils or fats. The liquid carrier can contain other suitable pharmaceutical additives such as solubilizers, emulsifiers, buffers, preservatives, sweeteners, flavoring agents, suspending agents, thickening agents, colors, viscosity regulators, stabilizers, and osmo-regulators. Examples of liquid carriers for oral and parenteral administration include, but are not limited to, water (particularly containing additives as described herein, e.g., cellulose derivatives such as a sodium carboxymethyl cellulose solution), alcohols (including monohydric alcohols and polyhydric alcohols, e.g., glycols) and their derivatives, and oils (e.g., fractionated coconut oil and arachis oil). For parenteral administration, the carrier can be an oily ester such as ethyl oleate and isopropyl myristate. Sterile liquid carriers are used in sterile liquid form compositions for parenteral administration. The liquid carrier for pressurized compositions can be halogenated hydrocarbon or other pharmaceutically acceptable propellants.

Liquid pharmaceutical compositions, which are sterile solutions or suspensions, can be utilized by, for example, intramuscular, intraperitoneal or subcutaneous injection. Sterile solutions can also be administered intravenously. Compositions for oral administration can be in either liquid or solid form.

Preferably the pharmaceutical composition is in unit dosage form, for example, as tablets, capsules, powders, solutions, suspensions, emulsions, granules, or suppositories. In such form, the pharmaceutical composition can be sub-divided in unit dose(s) containing appropriate quantities of the compound. The unit dosage forms can be packaged compositions, for example, packeted powders, vials, ampoules, prefilled syringes or sachets containing liquids. Alternatively, the unit dosage form can be a capsule or tablet itself, or it can be the appropriate number of any such compositions in package form. Such unit dosage form can contain from about 1 mg/kg of compound to about 500 mg/kg of compound, and can be given in a single dose or in two or more doses. Such doses can be administered in any manner useful in directing the compound(s) to the recipient's bloodstream, including orally, via implants, parenterally (including intravenous, intraperitoneal and subcutaneous injections), rectally, vaginally, and transdermally.

When administered for the treatment or inhibition of a particular disease state or disorder, it is understood that an effective dosage can vary depending upon the particular compound utilized, the mode of administration, and severity of the condition being treated, as well as the various physical factors related to the individual being treated. In therapeutic applications, a compound of the present teachings can be provided to a patient already suffering from a disease in an amount sufficient to cure or at least partially ameliorate the symptoms of the disease and its complications. The dosage to be used in the treatment of a specific individual typically must be subjectively determined by the attending physician. The variables involved include the specific condition and its state as well as the size, age and response pattern of the patient.

In some cases it may be desirable to administer a compound directly to the airways of the patient, using devices such as, but not limited to, metered dose inhalers, breath-operated inhalers, multidose dry-powder inhalers, pumps, squeeze-actuated nebulized spray dispensers, aerosol dispensers, and aerosol nebulizers. For administration by intranasal or intrabronchial inhalation, the compounds of the present teachings can be formulated into a liquid composition, a solid composition, or an aerosol composition. The liquid composition can include, by way of illustration, one or more compounds of the present teachings dissolved, partially dissolved, or suspended in one or more pharmaceutically acceptable solvents and can be administered by, for example, a pump or a squeeze-actuated nebulized spray dispenser. The solvents can be, for example, isotonic saline or bacteriostatic water. The solid composition can be, by way of illustration, a powder preparation including one or more compounds of the present teachings intermixed with lactose or other inert powders that are acceptable for intrabronchial use, and can be administered by, for example, an aerosol dispenser or a device that breaks or punctures a capsule encasing the solid composition and delivers the solid composition for inhalation. The aerosol composition can include, by way of illustration, one or more compounds of the present teachings, propellants, surfactants, and co-solvents, and can be administered by, for example, a metered device. The propellants can be a chlorofluorocarbon (CFC), a hydrofluoroalkane (FIFA), or other propellants that are physiologically and environmentally acceptable.

Compounds described herein can be administered parenterally or intraperitoneally. Solutions or suspensions of these compounds or a pharmaceutically acceptable salts, hydrates, or esters thereof can be prepared in water suitably mixed with a surfactant such as hydroxyl-propylcellulose. Dispersions can also be prepared in glycerol, liquid polyethylene glycols, and mixtures thereof in oils. Under ordinary conditions of storage and use, these preparations typically contain a preservative to inhibit the growth of microorganisms.

The pharmaceutical forms suitable for injection can include sterile aqueous solutions or dispersions and sterile powders for the extemporaneous preparation of sterile injectable solutions or dispersions. In some embodiments, the form can sterile and its viscosity permits it to flow through a syringe. The form preferably is stable under the conditions of manufacture and storage and can be preserved against the contaminating action of microorganisms such as bacteria and fungi. The carrier can be a solvent or dispersion medium containing, for example, water, ethanol, polyol (e.g., glycerol, propylene glycol and liquid polyethylene glycol), suitable mixtures thereof, and vegetable oils.

For tablet dosage forms, depending on dose, the drug may make up from 1 weight % to 80 weight % of the dosage form, more typically from 5 weight % to 60 weight % of the dosage form. In addition to the drug, tablets generally contain a disintegrant. Examples of disintegrants include sodium starch glycolate, sodium carboxymethyl cellulose, calcium carboxymethyl cellulose, croscarmellose sodium, crospovidone, polyvinylpyrrolidone, methyl cellulose, microcrystalline cellulose, lower alkyl-substituted hydroxypropyl cellulose, starch, pregelatinised starch and sodium alginate. Generally, the disintegrant will comprise from 1 weight % to 25 weight %, preferably from 5 weight % to 20 weight % of the dosage form.

Binders are generally used to impart cohesive qualities to a tablet formulation. Suitable binders include microcrystalline cellulose, gelatin, sugars, polyethylene glycol, natural and synthetic gums, polyvinylpyrrolidone, pregelatinised starch, hydroxypropyl cellulose and hydroxypropyl methylcellulose. Tablets may also contain diluents, such as lactose (monohydrate, spray-dried monohydrate, anhydrous and the like), mannitol, xylitol, dextrose, sucrose, sorbitol, microcrystalline cellulose, starch and dibasic calcium phosphate dihydrate.

Tablets may also optionally comprise surface active agents, such as sodium lauryl sulfate and polysorbate 80, and glidants such as silicon dioxide and talc. When present, surface active agents may comprise from 0.2 weight % to 5 weight % of the tablet, and glidants may comprise from 0.2 weight % to 1 weight % of the tablet.

Tablets also generally contain lubricants such as magnesium stearate, calcium stearate, zinc stearate, sodium stearyl fumarate, and mixtures of magnesium stearate with sodium lauryl sulphate. Lubricants generally comprise from 0.25 weight % to 10 weight %, preferably from 0.5 weight % to 3 weight % of the tablet. Other possible ingredients include anti-oxidants, colourants, flavoring agents, preservatives and taste-masking agents.

Exemplary tablets contain up to about 80% drug, from about 10 weight % to about 90 weight % binder, from about 0 weight % to about 85 weight % diluent, from about 2 weight % to about 10 weight % disintegrant, and from about 0.25 weight % to about 10 weight % lubricant.

Tablet blends may be compressed directly or by roller to form tablets. Tablet blends or portions of blends may alternatively be wet-, dry-, or melt-granulated, melt congealed, or extruded before tableting. The final formulation may comprise one or more layers and may be coated or uncoated; it may even be encapsulated.] The formulation of tablets is discussed in "Pharmaceutical Dosage Forms: Tablets, Vol. 1", by H. Lieberman and L. Lachman, Marcel Dekker, N.Y., N.Y., 1980 (ISBN 0-8247-6918-X).

The foregoing formulations for the various types of administration discussed above may be formulated to be immediate and/or modified release. Modified release formulations include delayed-, sustained-, pulsed-, controlled-, targeted and programmed release.

Suitable modified release formulations for the purposes of the invention are described in U.S. Pat. No. 6,106,864. Details of other suitable release technologies such as high energy dispersions and osmotic and coated particles are to be found in Verma et al, Pharmaceutical Technology On-line, 25(2), 1-14 (2001). The use of chewing gum to achieve controlled release is described in WO 00/35298.

Compounds described herein can be administered transdermally, i.e., administered across the surface of the body and the inner linings of bodily passages including epithelial and mucosal tissues. Such administration can be carried out using the compounds of the present teachings including pharmaceutically acceptable salts, hydrates, or esters thereof, in lotions, creams, foams, patches, suspensions, solutions, and suppositories (rectal and vaginal).

The compounds of the invention may also be administered directly into the blood stream, into muscle, or into an internal organ. Suitable means for parenteral administration include intravenous, intraarterial, intraperitoneal, intrathecal, intraventricular, intraurethral, intrasternal, intracranial, intramuscular and subcutaneous. Suitable devices for parenteral administration include needle (including microneedle) injectors, needle-free injectors and infusion techniques.

Parenteral formulations are typically aqueous solutions which may contain excipients such as salts, carbohydrates and buffering agents (preferably to a pH of from 3 to 9), but, for some applications, they may be more suitably formulated as a sterile non-aqueous solution or as a dried form to be used in conjunction with a suitable vehicle such as sterile, pyrogen-free water.

The preparation of parenteral formulations under sterile conditions, for example, by lyophilisation, may readily be accomplished using standard pharmaceutical techniques well known to those skilled in the art. The solubility of compounds of the disclosure used in the preparation of parenteral solutions may be increased by the use of appropriate formulation techniques, such as the incorporation of solubility-enhancing agents.

Formulations for parenteral administration may be formulated to be immediate and/or modified release. Thus, compounds of the invention may be formulated as a solid, semi-solid, or thixotropic liquid for administration as an implanted depot providing modified release of the active compound. Examples of such formulations include PGLA (Polymer Polyglycolic-Lactic Acid) microspheres.

Transdermal administration can be accomplished through the use of a transdermal patch containing a compound, such as a compound disclosed herein, and a carrier that can be inert to the compound, can be non-toxic to the skin, and can allow delivery of the compound for systemic absorption into the blood stream via the skin. The carrier can take any number of forms such as creams and ointments, pastes, gels, and occlusive devices. The creams and ointments can be viscous liquid or semisolid emulsions of either the oil-in-water or water-in-oil type. Pastes comprised of absorptive powders dispersed in petroleum or hydrophilic petroleum containing the compound can also be suitable. A variety of occlusive devices can be used to release the compound into the blood stream, such as a semi-permeable membrane covering a reservoir containing the compound with or without a carrier, or a matrix containing the compound. Other occlusive devices are known in the literature. Liposomes may also be used. Typical carriers include alcohol, water, mineral oil, liquid petrolatum, white petrolatum, glycerin, polyethylene glycol and propylene glycol. Penetration enhancers may be incorporated [see, for example, J Pharm Sci, 88 (10), 955-958 by Finnin and Morgan (October 1999).] Other means of topical administration include delivery by electroporation, iontophoresis, phonophoresis, sonophoresis and microneedle or needle-free (e.g. Powderject™, Bioject™, etc.) injection.

Compounds described herein can be administered rectally or vaginally in the form of a conventional suppository. Suppository formulations can be made from traditional materials, including cocoa butter, with or without the addition of waxes to alter the suppository's melting point, and glycerin. Water-soluble suppository bases, such as polyethylene glycols of various molecular weights, can also be used.

Lipid formulations or nanocapsules can be used to introduce compounds of the present teachings into host cells either in vitro or in vivo. Lipid formulations and nanocapsules can be prepared by methods known in the art.

The compounds of the invention may also be administered intranasally or by inhalation, typically in the form of a dry powder (either alone, as a mixture, for example, in a dry blend with lactose, or as a mixed component particle, for example, mixed with phospholipids, such as phosphatidylcholine) from a dry powder inhaler or as an aerosol spray from a pressurised container, pump, spray, atomiser (preferably an atomiser using electrohydrodynamics to produce a fine mist), or nebuliser, with or without the use of a suitable propellant, such as 1,1,1,2-tetrafluoroethane or 1,1,1,2,3,3,3-heptafluoropropane. For intranasal use, the powder may comprise a bioadhesive agent, for example, chitosan or cyclodextrin.

The pressurised container, pump, spray, atomizer, or nebuliser contains a solution or suspension of the compound(s) of the invention comprising, for example, ethanol, aqueous ethanol, or a suitable alternative agent for dispersing, solubilizing, or extending release of the active, a propellant(s) as solvent and an optional surfactant, such as sorbitan trioleate, oleic acid, or an oligolactic acid.

Prior to use in a dry powder or suspension formulation, the drug product is micronised to a size suitable for delivery by inhalation (typically less than 5 microns). [This may be achieved by any appropriate comminuting method, such as spiral jet milling, fluid bed jet milling, supercritical fluid processing to form nanoparticles, high pressure homogenisation, or spray drying.]

Capsules (made, for example, from gelatin or HPMC), blisters and cartridges for use in an inhaler or insufflator may be formulated to contain a powder mix of the compound of the invention, a suitable powder base such as lactose or starch and a performance modifier such as 1-leucine, mannitol, or magnesium stearate. The lactose may be anhydrous or in the form of the monohydrate, preferably the latter. Other suitable excipients include dextran, glucose, maltose, sorbitol, xylitol, fructose, sucrose and trehalose.

A suitable solution formulation for use in an atomiser using electrohydrodynamics to produce a fine mist may contain from 1 µg to 20 mg of the compound of the invention per actuation and the actuation volume may vary from 1 µl to 100 µl. A typical formulation may comprise a compound of formula (I), propylene glycol, sterile water, ethanol and sodium chloride. Alternative solvents which may be used instead of propylene glycol include glycerol and polyethylene glycol. Suitable flavours, such as menthol and levomenthol, or sweeteners, such as saccharin or saccharin sodium, may be added to those formulations of the invention intended for inhaled/intranasal administration.

Formulations for inhaled/intranasal administration may be formulated to be immediate and/or modified release using, for example, poly(DL-lactic-coglycolic acid (PGLA). Modified release formulations include delayed-, sustained-, pulsed-, controlled-, targeted and programmed release.

In the case of dry powder inhalers and aerosols, the dosage unit is determined by means of a valve which delivers a metered amount. Units in accordance with the invention are typically arranged to administer a metered dose which may be administered in a single dose or, more usually, as divided doses throughout the day.

The compounds of the invention may also be administered directly to the eye or ear, typically in the form of drops of a micronised suspension or solution in isotonic, pH-adjusted, sterile saline. Other formulations suitable for ocular and aural administration include ointments, biodegradable (e.g. absorbable gel sponges, collagen) and non-biodegradable (e.g. silicone) implants, wafers, lenses and particulate or vesicular systems, such as niosomes or liposomes. A polymer such as crossed-linked polyacrylic acid, polyvinylalcohol, hyaluronic acid; a cellulosic polymer, for example, hydroxypropylmethylcellulose, hydroxyethylcellulose, or methyl cellulose; or a heteropolysaccharide polymer, for example, gelan gum, may be incorporated together with a preservative, such as benzalkonium chloride. Such formulations may also be delivered by iontophoresis.

The compounds of the invention may be combined with soluble macromolecular entities, such as cyclodextrin and suitable derivatives thereof or polyethylene glycol-containing polymers, in order to improve their solubility, dissolution rate, taste-masking, bioavailability and/or stability for use in any of the aforementioned modes of administration.

Drug-cyclodextrin complexes, for example, are found to be generally useful for most dosage forms and administration routes. Both inclusion and non-inclusion complexes may be used. As an alternative to direct complexation with the drug, the cyclodextrin may be used as an auxiliary additive, i.e. as a carrier, diluent, or solubiliser. Most commonly used for these purposes are alpha-, beta- and gamma-cyclodextrins, examples of which may be found in International Patent Applications Nos. WO 91/11172, WO 94/02518 and WO 98/55148.

To increase the effectiveness of compounds of the present teachings, it can be desirable to combine a compound with other agents effective in the treatment of the target disease. For example, other active compounds (i.e., other active ingredients or agents) effective in treating the target disease can be administered with compounds of the present teachings. The other agents can be administered at the same time or at different times than the compounds disclosed herein.

Compounds of the present teachings can be useful for the treatment or inhibition of a pathological condition or disorder in a mammal, for example, a human subject. The present teachings accordingly provide methods of treating or inhibiting a pathological condition or disorder by providing to a mammal a compound of the present teachings including its pharmaceutically acceptable salt) or a pharmaceutical composition that includes one or more compounds of the present teachings in combination or association with pharmaceutically acceptable carriers. Compounds of the present teachings can be administered alone or in combination with other therapeutically effective compounds or therapies for the treatment or inhibition of the pathological condition or disorder.

Non-limiting examples of compositions according to the present invention include from about 0.001 mg to about 1000 mg of one or more of the compounds of the disclosure according to the present invention and one or more excipients; from about 0.01 mg to about 100 mg of one or more of the compounds of the disclosure according to the present invention and one or more excipients; and from about 0.1 mg to about 10 mg of one or more of the compounds of the disclosure according to the present invention; and one or more excipients.

For administration to human patients, for the above-mentioned therapeutic uses, the dosage administered will, of course, vary with the compound employed, the mode of administration, the treatment desired and the disorder indicated. For example, oral administration may require a greater total daily dose than intravenous administration. The total daily dosage of the compound of formula I or compound of formula II salt/solvate (active ingredient) will, generally, be in the range from 1 mg to 1 gram, preferably 1 mg to 250 mg, more preferably 10 mg to 100 mg. The total daily dose may be administered in single or divided doses. The present invention also encompasses sustained release compositions. These dosages are based on an average human subject having a weight of about 65 kg to 70 kg. The physician will readily be able to determine doses for subjects whose weight falls outside this range, such as infants and the elderly.

Dosage regimens may be adjusted to provide the optimum desired response. For example, a single bolus may be administered, several divided doses may be administered over time or the dose may be proportionally reduced or increased as indicated by the exigencies of the therapeutic situation. It is especially advantageous to formulate parenteral compositions in dosage unit form for ease of administration and uniformity of dosage. Dosage unit form, as used herein, refers to physically discrete units suited as unitary dosages for the mammalian subjects to be treated; each unit containing a predetermined quantity of active compound calculated to produce the desired therapeutic effect in association with the required pharmaceutical carrier. The specification for the dosage unit forms of the invention are dictated by and directly dependent on (a) the unique characteristics of the chemotherapeutic agent and the particular therapeutic or prophylactic effect to be achieved, and (b) the limitations inherent in the art of compounding such an active compound for the treatment of sensitivity in individuals.

Thus, the skilled artisan would appreciate, based upon the disclosure provided herein, that the dose and dosing regimen is adjusted in accordance with methods well-known in the therapeutic arts. That is, the maximum tolerable dose can be readily established, and the effective amount providing a detectable therapeutic benefit to a patient may also be determined, as can the temporal requirements for administering each agent to provide a detectable therapeutic benefit to the patient. Accordingly, while certain dose and administration regimens are exemplified herein, these examples in no way limit the dose and administration regimen that may be provided to a patient in practicing the present invention.

It is to be noted that dosage values may vary with the type and severity of the condition to be alleviated, and may include single or multiple doses. It is to be further understood that for any particular subject, specific dosage regimens should be adjusted over time according to the individual need and the professional judgment of the person administering or supervising the administration of the compositions, and that dosage ranges set forth herein are exemplary only and are not intended to limit the scope or practice of the claimed composition. For example, doses may be adjusted based on pharmacokinetic or pharmacodynamic parameters, which may include clinical effects such as toxic effects and/or laboratory values. Thus, the present invention encompasses intra-patient dose-escalation as determined by the skilled artisan. Determining appropriate dosages and regiments for administration of the chemotherapeutic agent are well-known in the relevant art and would be understood to be encompassed by the skilled artisan once provided the teachings disclosed herein.

A pharmaceutical composition of the invention may be prepared, packaged, or sold in bulk, as a single unit dose, or as a plurality of single unit doses. As used herein, a "unit dose" is discrete amount of the pharmaceutical composition comprising a predetermined amount of the active ingredient. The amount of the active ingredient is generally equal to the dosage of the active ingredient which would be administered to a subject or a convenient fraction of such a dosage such as, for example, one-half or one-third of such a dosage.

The relative amounts of the active ingredient, and of the pharmaceutically acceptable carrier, and any additional active ingredients in a pharmaceutical composition of the invention will vary, depending upon the type of animal being treated, the type of disease being treated, the sex and age of the patient, and the size and condition of the subject treated, and further depend upon the route by which the composition is to be administered. By way of example, the composition may comprise between 0.1% and 100% (w/w) active ingredient.

Compounds of the disclosure that and isotopically labeled variants thereof, may be useful for the diagnosis and/or treatment of diseases that involve the formation of tau oligomers, including, for example, Alzheimer's disease, Amyotrophic lateral sclerosis/parkinsonism-dementia complex, argyrophilic grain dementia, corticobasal degeneration, Creutzfeldt-Jakob disease, dementia pugilistica/chronic traumatic encephalopathy, diffuse neurofibrillary tangles with calcification, Down's syndrome, frontotemporal dementia with parkinsonism linked to chromosome 17, Gerstmann-Sträussler-Scheinker disease, Hallervorden-Spatz disease, myotonic dystrophy, Niemann-Pick disease, type C, non-Guamanian motor neuron disease with neurofibrillary tangles, Pick's disease, postencephalitic parkinsonism, prion protein cerebral amyloid angiopathy, progressive subcortical gliosis, progressive supranuclear palsy, subacute sclerosing panencephalitis, and tangle only dementia. Means of detecting labels are well known to those skilled in the art. For example, isotopic labels may be detected using imaging techniques, photographic film or scintillation counters. In a preferred embodiment, the label is detected in vivo in the brain of the subject by imaging techniques, for example positron emission tomography (PET).

The labeled compound of the invention preferably contains at least one radionuclide as a label. Positron-emitting radionuclides are all candidates for usage. In the context of this invention the radionuclide is preferably selected from $^{11}C$, $^{13}C$, $^{14}C$, $^{18}F$, $^{15}O$, $^{13}N$, $^{32}S$, $^{2}H$, and $^{3}H$, more preferably from $^{11}C$, and $^{18}F$. The tracer can be selected in accordance with the detection method chosen. Before conducting the method of the present invention, a diagnostically effective amount of a labeled or unlabeled compound of the invention is administered to a living body, including a human. The diagnostically effective amount of the labeled or unlabeled compound of the invention to be administered before conducting the in-vivo method for the present invention is within a range of from 0.1 ng to 100 mg per kg body weight, preferably within a range of from 1 ng to 10 mg per kg body weight.

Procedures

The following procedures can be utilized in evaluating and selecting compounds as inhibitors of tau oligomer formation.

In Vitro Assay Methods

Bacterial recombinant human tau 4R2N (the largest isoform of tau in the central nervous system, 441 amino acids in length, Seq ID 1) constructs with either 6x-His or StrepII N-terminal epitope tags were purified from bacterial lysate using denaturing conditions to prepare tau in its monomeric form.

ALA Assay: AlphaLisa Assay (ALA) was used as a primary screen for identifying compounds that inhibit tau oligomer formation. It is a bead based assay that only gives signal when the beads are in close proximity to each other. When the tau monomer (target) is incubated it forms higher order aggregates (dimer, trimer, tetramer, etc) so that when the donor and acceptor beads bind to the epitope tags of tau they are in close proximity and generate signal.

Tau target (equal mixture of each construct at 300 nM) was prepared in buffer (Tris-HCl pH 7.4) and was incubated in 96-well plates at room temperature for 4 hours with vehicle control (DMSO) and a dose range of a compound of the disclosure (0.098 uM-50 uM). AlphaLisa acceptor beads & donor beads with ligands to the epitope tags (Perkin Elmer) were diluted (final 20 ug/mL per bead) in bead buffer (25 mM HEPES pH 7.4, 100 mM NaCl, 0.1% Tween-20), added to the wells and incubated 1 hour at room temperature. The positive control (non-incubated target) & blank (no tau) were prepared and mixed with beads in bead buffer and the plate was read immediately using the EnVision plate reader (Perkin Elmer).

CONFA Assay: Confirmatory Assay (CONFA) used as a secondary screen for confirming the mechanism of action of compounds identified as hits using the ALA assay. The assay is performed using a similar procedure as ALA except that it utilizes SDS-PAGE for visualization and quantification of tau monomer and aggregated species (dimer, trimer, tetramer, pentamer, etc.). Only a single construct of tau without epitope tags is necessary, but the assay can use the same target prepared for the ALA assay also.

For the CONFA assay, Tau target (300 nM) was prepared in buffer (Tris-HCl pH 7.4) and was incubated at room temperature for 3 hours with vehicle control (DMSO) and a dose range of a compound of the disclosure (0.098 uM-50 uM). Samples were mixed with an equal volume of 2×SDS sample buffer (4% SDS, 20% glycerol, 0.004% bromphenol blue, 125 mM Tris HCl, pH 7.0) to resolve tau monomer and disulfide-finked oligomers on 4-20% gradient polyacrylamide gels (Biorad) along with positive control (non-oligomerized tau target). The gels were stained with Oriole Fluorescent Gel Stain (BioRad) and imaged using the FluorChem R system (Protein Simple). AlphaView software (Protein Simple) was used for quantification of tau monomer and oligomers.

Data provided for compounds that were soluble in the test solutions described herein are listed in Table 3.

TABLE 3

| Example | ALA IC$_{50}$ (uM) | CONFA IC$_{50}$ (uM) |
|---|---|---|
| Ex. 2 | 1.27 | 4.27 |
| Ex. 3 | 7.55 | 37.1 |
| Ex. 4 | 1.39 | 24.1 |
| Ex. 5 | 3.03 | 0.364 |
| Ex. 6 | 6.35 | |
| Ex. 7 | 0.1 | |
| Ex. 8 | 1.31 | 5.57 |
| Ex. 9 | >10 | |
| Ex. 12 | 6.09 | 22.5 |

TABLE 3-continued

| Example | ALA IC$_{50}$ (uM) | CONFA IC$_{50}$ (uM) |
|---|---|---|
| Ex. 13 | 5.78 | 3.23 |
| Ex. 14 | 2.06 | |
| Ex. 15 | 0.1 | 1.32 |
| Ex. 16 | 1.93 | 1.31 |
| Ex. 18 | 7.67 | |
| Ex. 19 | 20.8 | |
| Ex. 20 | 15.4 | |
| Ex. 21 | 1.17 | |
| Ex. 22 | 3.42 | 7.57 |
| Ex. 23 | 1.57 | 7.18 |
| Ex. 24 | 4.02 | 11.8 |
| Ex. 26 | >10 | |
| Ex. 28 | 2.48 | 17.5 |
| Ex. 29 | | 7.38 |
| Ex. 30 | | 20.4 |
| Ex. 31 | | 9.28 |

Suitable daily doses of the compound for the therapeutic treatment of humans are about 0.01-100 mg/kg body weight upon oral administration and 0.001-100 mg/kg body weight on parenteral administration. However, for any pharmaceutical composition used in the invention, the therapeutically effective dose can be estimated initially from animal models. Dose-response curves derived from animal systems are then used to determine testing doses for the initial clinical studies in humans. In safety determinations for each composition, the dose and frequency of administration should meet or exceed those anticipated for use in the clinical trial.

Other factors to consider are the dosage procedure, the conditions of a patient or a subject animal such as age, body weight, sex, sensitivity, feed, dosage period, drugs used in combination, seriousness of the disease. The appropriate dose and dosage times under certain conditions can be determined by the test based on the above-described indices but may be refined and ultimately decided according to the judgment of the practioner and each patient's circumstances (age, general condition, severity of symptoms, sex, etc.) according to standard clinical techniques.

Toxicity and therapeutic efficacy of the compositions of the invention can be determined by standard pharmaceutical procedures in experimental animals, e.g., by determining the LD50 (the dose lethal to 50% of the population) and the ED50 (the dose therapeutically effective in 50% of the population). The dose ratio between therapeutic and toxic effects is the therapeutic index and it can be expressed as the ratio ED50/LD50. Compositions that exhibit large therapeutic indices are preferred.

Treatment duration can be short-term, e.g. several weeks (for example 10-14 weeks), or long-term until the attending physician deems further administration no longer is necessary to obtain a benefit.

What is claimed is:

1. A compound selected from the group consisting of:
compounds of formula (I),

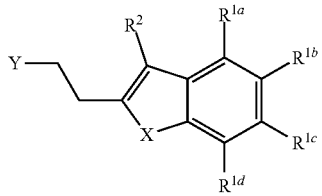

(I)

Including enantiomers, diastereomers, hydrates, solvates, pharmaceutically acceptable salts, and complexes thereof, wherein $R^{1a}$ and $R^{1d}$ are each independently selected from the group consisting of hydrogen, halogen, $C_{1-6}$ alkyl, $C_{1-6}$ alkoxy, $C_{1-6}$ haloalkyl, and $C_{1-6}$ haloalkoxy;

$R^{1b}$ and $R^{1c}$ are selected from the group consisting of hydrogen, halogen, optionally substituted aryl and optionally substituted heteroaryl;

When $R^{1b}$ is hydrogen, $R^{1c}$ is not hydrogen;

When $R^{1c}$ is hydrogen, $R^{1b}$ is not hydrogen;

$R^2$ is selected from the group consisting of $C_{1-6}$ alkyl, $C_{3-7}$ branched alkyl, $C_{1-6}$ alkylaryl, optionally substituted aryl and optionally substituted heteroaryl;

X is selected from the group consisting of oxygen, sulfur, NH, and $NR^5$;

Wherein $R^5$ is $C_{1-6}$ alkyl;

Y is selected from the group consisting of

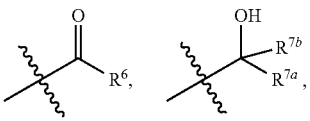

and optionally substituted 2-benzimidazole;

Wherein $R^6$ is selected from the group consisting of hydrogen, OH, $OR^{7c}$, optionally substituted $C_{1-6}$ alkyl, $NR^{3a}R^{3b}$, optionally substituted aryl, and optionally substituted heteroaryl;

$R^{3a}$ and $R^{3b}$ are independently selected from the group consisting of hydrogen and $C_{1-6}$ alkyl;

$R^{3a}$ and $R^{3b}$ are taken together with the atom to which they are bound to form a three to six membered saturated ring optionally substituted with a group selected from OH, $C_{1-6}$ alkyl, $NR^{8a}R^{8b}$ optionally including a member selected from the group consisting of O, $NR^8$, and S;

$R^8$ is selected from the group consisting of hydrogen, $C_{1-6}$ alkyl, and CO ($C_{1-6}$alkyl);

$R^{8a}$ and $R^{8b}$ are independently selected from of hydrogen and $C_{1-6}$ alkyl;

$R^{7a}$ is selected from the group consisting of hydrogen and $C_{1-6}$ alkyl;

$R^{7b}$ is selected from the group consisting of $C_{1-6}$ alkyl, aryl, and heteroaryl;

and $R^{7c}$ is selected from the group consisting of $C_{1-6}$ alkyl and $C_{3-7}$ branched alkyl;

compounds having formula (II):

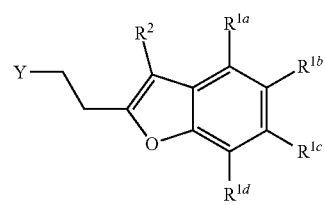

(II)

including enantiomers, diastereomers, hydrates, solvates, pharmaceutically acceptable salts, and complexes thereof, wherein $R^{1a}$, $R^{1b}$, $R^{1c}$, $R^{1d}$, $R^2$, and Y are as defined for formula I;

compounds having formula (III):

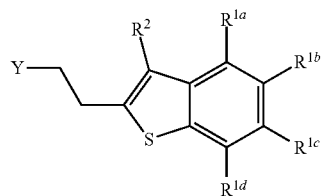

(III)

including enantiomers, diastereomers, hydrates, solvates, pharmaceutically acceptable salts, and complexes thereof, wherein $R^{1a}$, $R^{1b}$, $R^{1c}$, $R^{1d}$, $R^2$, and Y are as defined for formula I;

compounds having formula (IV):

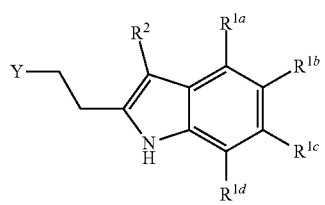

(IV)

including enantiomers, diastereomers, hydrates, solvates, pharmaceutically acceptable salts, and complexes thereof, wherein $R^{1a}$, $R^{1b}$, $R^{1c}$, $R^{1d}$, $R^2$, and Y are as defined for formula I;

compounds having formula (V):

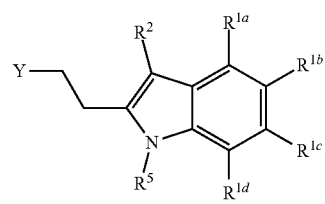

(V)

including enantiomers, diastereomers, hydrates, solvates, pharmaceutically acceptable salts, and complexes thereof, wherein $R^{1a}$, $R^{1b}$, $R^{1c}$, $R^{1d}$, $R^2$, $R^5$ and Y are as defined for formula I;

compounds having formula (V):

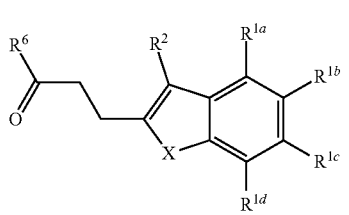
(VI)

including enantiomers, diastereomers, hydrates, solvates, pharmaceutically acceptable salts, and complexes thereof, wherein $R^{1a}$, $R^{1b}$, $R^{1c}$, $R^{1d}$, $R^2$, $R^6$, and X are as defined for formula I;

compounds having formula (VI):

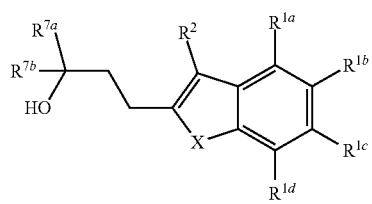
(VII)

including enantiomers, diastereomers, hydrates, solvates, pharmaceutically acceptable salts, and complexes thereof, wherein $R^{1a}$, $R^{1b}$, $R^{1c}$, $R^{1d}$, $R^2$, $R^{7a}$, $R^{7b}$ and X are as defined for formula I;

compounds having formula (VII):

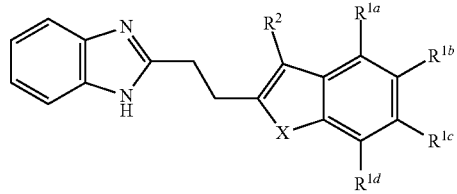
(VIII)

including enantiomers, diastereomers, hydrates, solvates, pharmaceutically acceptable salts, and complexes thereof, wherein $R^{1a}$, $R^{1b}$, $R^{1c}$, $R^{1d}$, $R^2$ and X are as defined for formula I;

compounds having formula (IX):

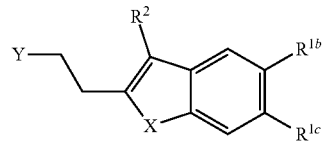
(IX)

including enantiomers, diastereomers, hydrates, solvates, pharmaceutically acceptable salts, and complexes thereof, wherein $R^{1b}$, $R^{1c}$, $R^2$, X and Y are as defined for formula I;

compounds having formula (X):

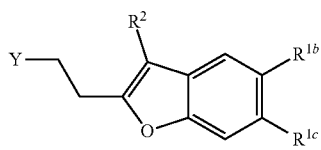
(X)

including enantiomers, diastereomers, hydrates, solvates, pharmaceutically acceptable salts, and complexes thereof, wherein $R^{1b}$, $R^{1c}$, $R^2$, and Y are as defined for formula I;

compounds having formula (XI):

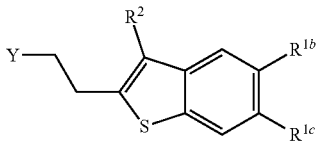
(XI)

including enantiomers, diastereomers, hydrates, solvates, pharmaceutically acceptable salts, and complexes thereof, wherein $R^{1b}$, $R^{1c}$, $R^2$, and Y are as defined for formula I;

compounds having formula (XII):

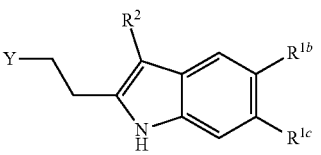
(XII)

including enantiomers, diastereomers, hydrates, solvates, pharmaceutically acceptable salts, and complexes thereof, wherein $R^{1b}$, $R^{1c}$, $R^2$, and Y are as defined for formula I;

compounds having formula (XIII):

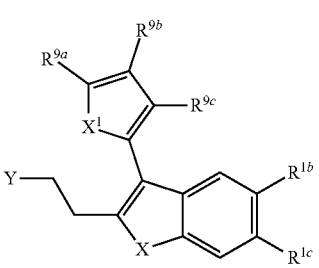
(XIII)

including enantiomers, diastereomers, hydrates, solvates, pharmaceutically acceptable salts, and complexes thereof, wherein $R^{1b}$, $R^{1c}$, X and Y are as defined for formula I;

$R^{9a}$, $R^{9b}$, and $R^{9c}$ are independently selected from the group consisting of hydrogen, halogen, and $C_{1-6}$ alkyl; and $X^1$ is selected from the group consisting of oxygen and sulfur;

compounds having formula (XIV):

$$\text{(XIV)}$$

including enantiomers, diastereomers, hydrates, solvates, pharmaceutically acceptable salts, and complexes thereof, wherein $R^{1c}$, $R^2$, X and Y are as defined for formula I;

$A^1$, $A^2$, $A^3$, $A^4$, and $A^5$ are selected from the group consisting of nitrogen and $CR^{10}$;

No more than two of $A^1$, $A^2$, $A^3$, $A^4$, and $A^5$ may be nitrogen;

$R^{10}$ is selected from the group consisting of hydrogen, $C_{1-6}$ alkyl, $C_{1-6}$ haloalkyl, $C_{1-6}$ haloalkoxy, $C_{1-6}$ alkoxy, halogen, hydroxy, and $NHSO_2R^{11}$;

and $R^{11}$ is independently selected from the group consisting of hydrogen and $C_{1-6}$ alkyl;

compounds having formula (XIVa):

$$\text{(XIVa)}$$

including enantiomers, diastereomers, hydrates, solvates, pharmaceutically acceptable salts, and complexes thereof, wherein $R^{1b}$, $R^2$, X and Y are as defined for formula I;

$A^6$, $A^7$, $A^8$, $A^9$, and $A^{10}$ are selected from the group consisting of nitrogen and $CR^{10}$;

No more than two of $A^6$, $A^7$, $A^8$, $A^9$, and $A^{10}$ may be nitrogen;

$R^{10}$ is selected from the group consisting of hydrogen, $C_{1-6}$ alkyl, $C_{1-6}$ haloalkyl, $C_{1-6}$ haloalkoxy, $C_{1-6}$ alkoxy, halogen, hydroxy, and $NHSO_2R^{11}$;

and $R^{11}$ is independently selected from the group consisting of hydrogen and $C_{1-6}$ alkyl;

compounds having formula (XIVb):

$$\text{(XIVb)}$$

including enantiomers, diastereomers, hydrates, solvates, pharmaceutically acceptable salts, and complexes thereof, wherein $R^2$, X and Y are as defined for formula I;

$A^1$, $A^2$, $A^3$, $A^4$, $A^5$, $A^6$, $A^7$, $A^8$, $A^9$, and $A^{10}$ are selected from the group consisting of nitrogen and $CR^{10}$;

No more than two of $A^1$, $A^2$, $A^3$, $A^4$, and $A^5$ may be nitrogen;

No more than two of $A^6$, $A^7$, $A^8$, $A^9$, and $A^{10}$ may be nitrogen;

$R^{10}$ is selected from the group consisting of hydrogen, $C_{1-6}$ alkyl, $C_{1-6}$ haloalkyl, $C_{1-6}$ haloalkoxy, $C_{1-6}$ alkoxy, halogen, hydroxy, and $NHSO_2R^{11}$;

and $R^{11}$ is independently selected from the group consisting of hydrogen and $C_{1-6}$ alkyl;

compounds having formula (XV):

$$\text{(XV)}$$

including enantiomers, diastereomers, hydrates, solvates, pharmaceutically acceptable salts, and complexes thereof, wherein $R^{1c}$, $R^2$ and Y are as defined for formula I;

$A^1$, $A^2$, $A^3$, $A^4$, and $A^5$ are selected from the group consisting of nitrogen and $CR^{10}$;

No more than two of $A^1$, $A^2$, $A^3$, $A^4$, and $A^5$ may be nitrogen;

$R^{10}$ is selected from the group consisting of hydrogen, $C_{1-6}$ alkyl, $C_{1-6}$ haloalkyl, $C_{1-6}$ haloalkoxy, $C_{1-6}$ alkoxy, halogen, hydroxy, and $NHSO_2R^{11}$;

and $R^{11}$ is independently selected from the group consisting of hydrogen and $C_{1-6}$ alkyl;

compounds having formula (XVa):

$$\text{(XVa)}$$

including enantiomers, diastereomers, hydrates, solvates, pharmaceutically acceptable salts, and complexes thereof, wherein $R^{1b}$, $R^2$ and Y are as defined for formula I;

$A^6$, $A^7$, $A^8$, $A^9$, and $A^{10}$ are selected from the group consisting of nitrogen and $CR^{10}$;

No more than two of $A^6$, $A^7$, $A^8$, $A^9$, and $A^{10}$ may be nitrogen;

$R^{10}$ is selected from the group consisting of hydrogen, $C_{1-6}$ alkyl, $C_{1-6}$ haloalkyl, $C_{1-6}$ haloalkoxy, $C_{1-6}$ alkoxy, halogen, hydroxy, and $NHSO_2R^{11}$;

and $R^{11}$ is independently selected from the group consisting of hydrogen and $C_{1-6}$ alkyl;

compounds having formula (XVb):

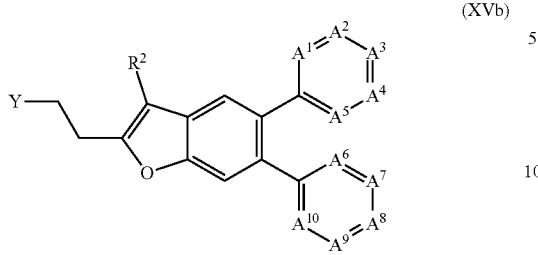

(XVb)

including enantiomers, diastereomers, hydrates, solvates, pharmaceutically acceptable salts, and complexes thereof, wherein $R^2$ and Y are as defined for formula I;
$A^1, A^2, A^3, A^4, A^5, A^6, A^7, A^8, A^9$, and $A^{10}$ are selected from the group consisting of nitrogen and $CR^{10}$;
No more than two of $A^1, A^2, A^3, A^4$, and $A^5$ may be nitrogen;
No more than two of $A^6, A^7, A^8, A^9$, and $A^{10}$ may be nitrogen;
$R^{10}$ is selected from the group consisting of hydrogen, $C_{1-6}$ alkyl, $C_{1-6}$ haloalkyl, $C_{1-6}$ haloalkoxy, $C_{1-6}$ alkoxy, halogen, hydroxy, and $NHSO_2R^{11}$;
and $R^{11}$ is independently selected from the group consisting of hydrogen and $C_{1-6}$ alkyl;
compounds having formula (XVI):

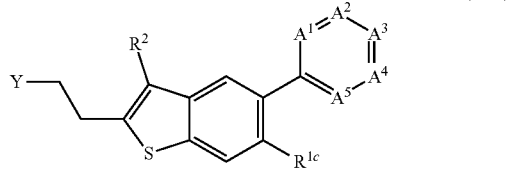

(XVI)

including enantiomers, diastereomers, hydrates, solvates, pharmaceutically acceptable salts, and complexes thereof, wherein $R^{1c}$, $R^2$ and Y are as defined for formula I;
$A^1, A^2, A^3, A^4$, and $A^5$ are selected from the group consisting of nitrogen and $CR^{10}$;
No more than one of $A^1, A^2, A^3, A^4$, and $A^5$ may be nitrogen;
$R^{10}$ is selected from the group consisting of hydrogen, $C_{1-6}$ alkyl, $C_{1-6}$ haloalkyl, $C_{1-6}$ haloalkoxy, $C_{1-6}$ alkoxy, halogen, hydroxy, and $NHSO_2R^{11}$;
and $R^{11}$ is independently selected from the group consisting of hydrogen and $C_{1-6}$ alkyl;
compounds having formula (XVIa):

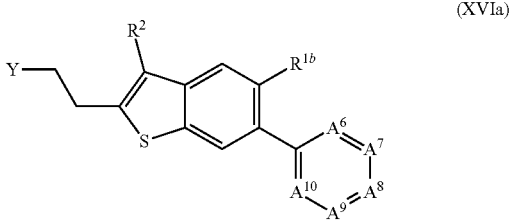

(XVIa)

including enantiomers, diastereomers, hydrates, solvates, pharmaceutically acceptable salts, and complexes thereof, wherein $R^{1b}$, $R^2$ and Y are as defined for formula I;
$A^6, A^7, A^8, A^9$, and $A^{10}$ are selected from the group consisting of nitrogen and $CR^{10}$;
No more than two of $A^6, A^7, A^8, A^9$, and $A^{10}$ may be nitrogen;
$R^{10}$ is selected from the group consisting of hydrogen, $C_{1-6}$ alkyl, $C_{1-6}$ haloalkyl, $C_{1-6}$ haloalkoxy, $C_{1-6}$ alkoxy, halogen, hydroxy, and $NHSO_2R^{11}$;
and $R^{11}$ is independently selected from the group consisting of hydrogen and $C_{1-6}$ alkyl;
compounds having formula (XVIb):

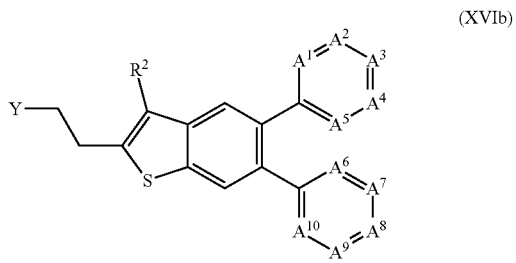

(XVIb)

including enantiomers, diastereomers, hydrates, solvates, pharmaceutically acceptable salts, and complexes thereof, wherein $R^2$ and Y are as defined for formula I;
$A^1, A^2, A^3, A^4, A^5, A^6, A^7, A^8, A^9$, and $A^{10}$ are selected from the group consisting of nitrogen and $CR^{10}$;
No more than two of $A^1, A^2, A^3, A^4$, and $A^5$ may be nitrogen;
No more than two of $A^6, A^7, A^8, A^9$, and $A^{10}$ may be nitrogen;
$R^{10}$ is selected from the group consisting of hydrogen, $C_{1-6}$ alkyl, $C_{1-6}$ haloalkyl, $C_{1-6}$ haloalkoxy, $C_{1-6}$ alkoxy, halogen, hydroxy, and $NHSO_2R^{11}$;
and $R^{11}$ is independently selected from the group consisting of hydrogen and $C_{1-6}$ alkyl;
compounds having formula (XVII):

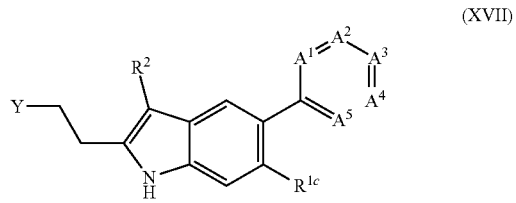

(XVII)

including enantiomers, diastereomers, hydrates, solvates, pharmaceutically acceptable salts, and complexes thereof, wherein $R^{1c}$, $R^2$ and Y are as defined for formula I;
$A^1, A^2, A^3, A^4$, and $A^5$ are selected from the group consisting of nitrogen and $CR^{10}$;
No more than one of $A^1, A^2, A^3, A^4$, and $A^5$ may be nitrogen;
$R^{10}$ is selected from the group consisting of hydrogen, $C_{1-6}$ alkyl, $C_{1-6}$ haloalkyl, $C_{1-6}$ haloalkoxy, $C_{1-6}$ alkoxy, halogen, hydroxy, and $NHSO_2R^{11}$;
and $R^{11}$ is independently selected from the group consisting of hydrogen and $C_{1-6}$ alkyl;

compounds having formula (XVIIa):

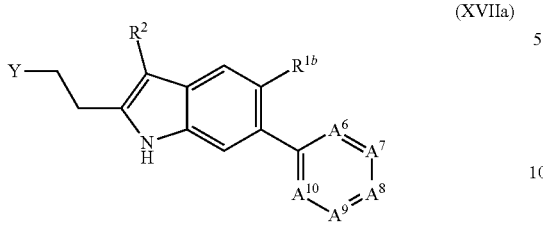
(XVIIa)

including enantiomers, diastereomers, hydrates, solvates, pharmaceutically acceptable salts, and complexes thereof, wherein $R^2$, $R^{1b}$ and Y are as defined for formula I;
$A^6$, $A^7$, $A^8$, $A^9$, and $A^{10}$ are selected from the group consisting of nitrogen and $CR^{10}$;
No more than two of $A^6$, $A^7$, $A^8$, $A^9$, and $A^{10}$ may be nitrogen;
$R^{10}$ is selected from the group consisting of hydrogen, $C_{1-6}$ alkyl, $C_{1-6}$ haloalkyl, $C_{1-6}$ haloalkoxy, $C_{1-6}$ alkoxy, halogen, hydroxy, and $NHSO_2R^{11}$;
and $R^{11}$ is independently selected from the group consisting of hydrogen and $C_{1-6}$ alkyl;
compounds having formula (XVIIb):

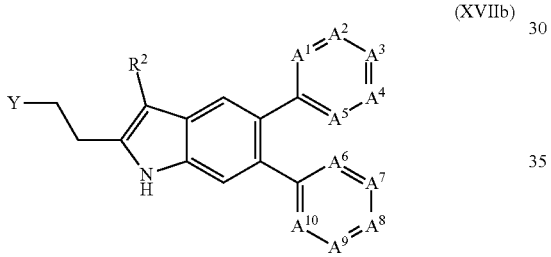
(XVIIb)

including enantiomers, diastereomers, hydrates, solvates, pharmaceutically acceptable salts, and complexes thereof, wherein $R^2$ and Y are as defined for formula I;
$A^1$, $A^2$, $A^3$, $A^4$, $A^5$, $A^6$, $A^7$, $A^8$, $A^9$, and $A^{10}$ are selected from the group consisting of nitrogen and $CR^{10}$;
No more than two of $A^1$, $A^2$, $A^3$, $A^4$, and $A^5$ may be nitrogen;
No more than two of $A^6$, $A^7$, $A^8$, $A^9$, and $A^{10}$ may be nitrogen;
$R^{10}$ is selected from the group consisting of hydrogen, $C_{1-6}$ alkyl, $C_{1-6}$ haloalkyl, $C_{1-6}$ haloalkoxy, $C_{1-6}$ alkoxy, halogen, hydroxy, and $NHSO_2R^{11}$;
and $R^{11}$ is independently selected from the group consisting of hydrogen and $C_{1-6}$ alkyl;
compounds having formula (XVIII):

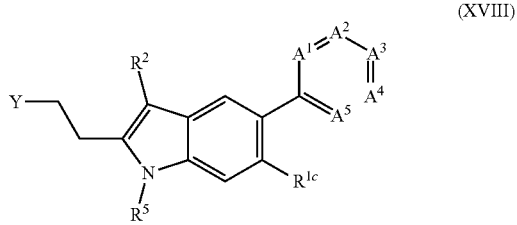
(XVIII)

including enantiomers, diastereomers, hydrates, solvates, pharmaceutically acceptable salts, and complexes thereof, wherein $R^{1c}$, $R^2$, $R^5$ and Y are as defined for formula I;
$A^1$, $A^2$, $A^3$, $A^4$, and $A^5$ are selected from the group consisting of nitrogen and $CR^{10}$;
No more than one of $A^1$, $A^2$, $A^3$, $A^4$, and $A^5$ may be nitrogen;
$R^{10}$ is selected from the group consisting of hydrogen, $C_{1-6}$ alkyl, $C_{1-6}$ haloalkyl, $C_{1-6}$ haloalkoxy, $C_{1-6}$ alkoxy, halogen, hydroxy, and $NHSO_2R^{11}$;
and $R^{11}$ is independently selected from the group consisting of hydrogen and $C_{1-6}$ alkyl;
compounds having formula (XVIIIa):

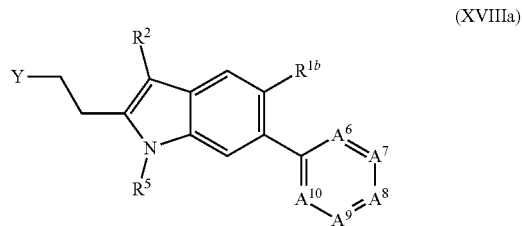
(XVIIIa)

including enantiomers, diastereomers, hydrates, solvates, pharmaceutically acceptable salts, and complexes thereof, wherein $R^{1b}$, $R^2$, $R^5$ and Y are as defined for formula I;
$A^6$, $A^7$, $A^8$, $A^9$, and $A^{10}$ are selected from the group consisting of nitrogen and $CR^{10}$;
No more than two of $A^6$, $A^7$, $A^8$, $A^9$, and $A^{10}$ may be nitrogen;
$R^{10}$ is selected from the group consisting of hydrogen, $C_{1-6}$ alkyl, $C_{1-6}$ haloalkyl, $C_{1-6}$ haloalkoxy, $C_{1-6}$ alkoxy, halogen, hydroxy, and $NHSO_2R^{11}$;
and $R^{11}$ is independently selected from the group consisting of hydrogen and $C_{1-6}$ alkyl;
compounds having formula (XVIIIb):

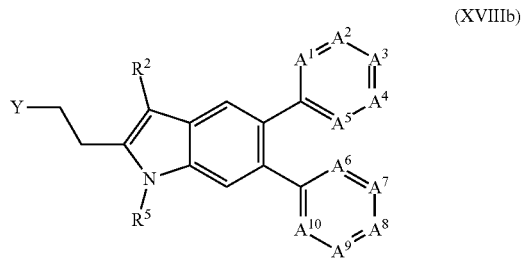
(XVIIIb)

including enantiomers, diastereomers, hydrates, solvates, pharmaceutically acceptable salts, and complexes thereof, wherein $R^2$, $R^5$ and Y are as defined for formula I;
$A^1$, $A^2$, $A^3$, $A^4$, $A^5$, $A^6$, $A^7$, $A^8$, $A^9$, and $A^{10}$ are selected from the group consisting of nitrogen and $CR^{10}$;
no more than two of $A^1$, $A^2$, $A^3$, $A^4$, and $A^5$ may be nitrogen;
no more than two of $A^6$, $A^7$, $A^8$, $A^9$, and $A^{10}$ may be nitrogen;
$R^{10}$ is selected from the group consisting of hydrogen, $C_{1-6}$ alkyl, $C_{1-6}$ haloalkyl, $C_{1-6}$ haloalkoxy, $C_{1-6}$ alkoxy, halogen, hydroxy, and $NHSO_2R^{11}$;

and R[11] is independently selected from the group consisting of hydrogen and $C_{1-6}$ alkyl.
2. A compound according to claim 1 wherein said compound is selected from the following structures:
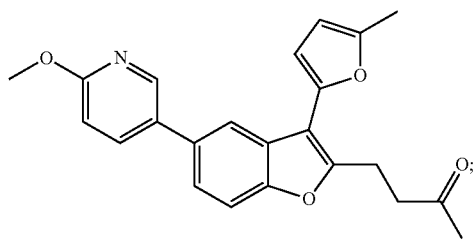
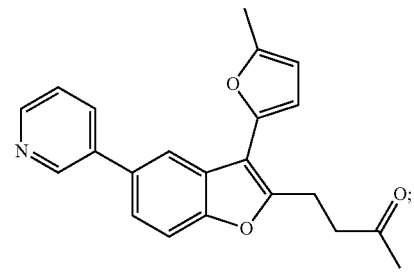
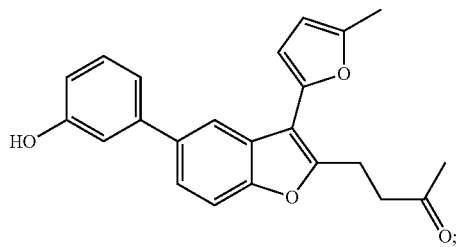
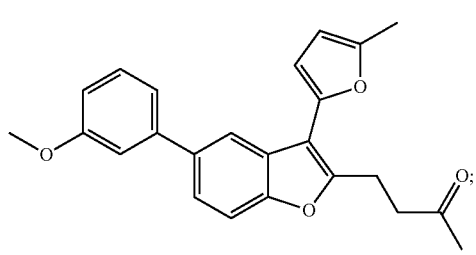
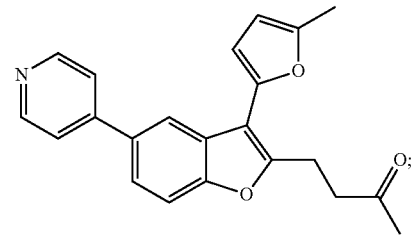
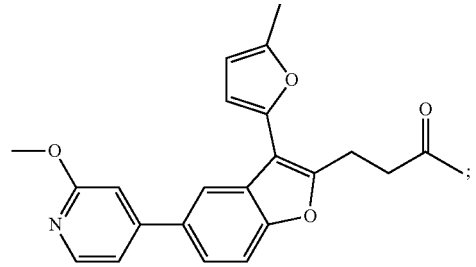
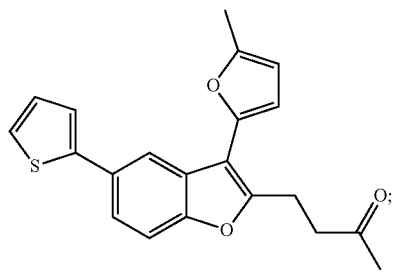 [SMILES: CC(=O)CCc1oc2ccc(-c3cccs3)cc2c1-c1ccc(C)o1]
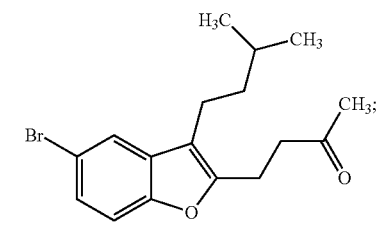
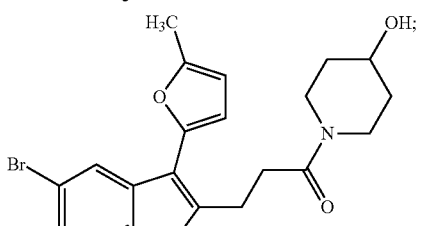
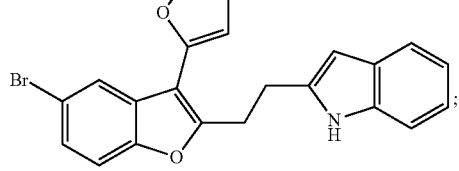
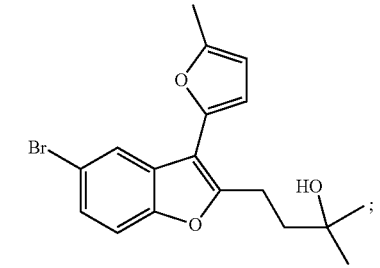
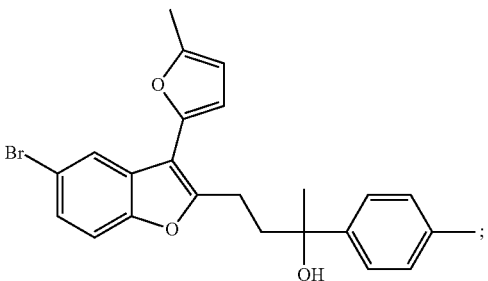

103
-continued
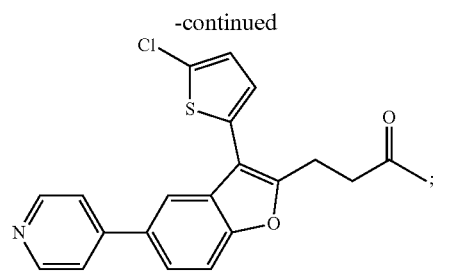
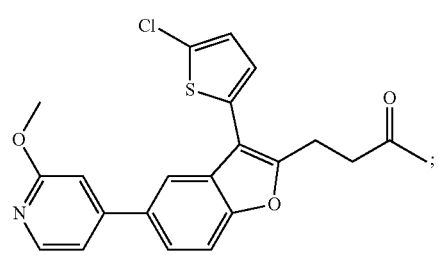
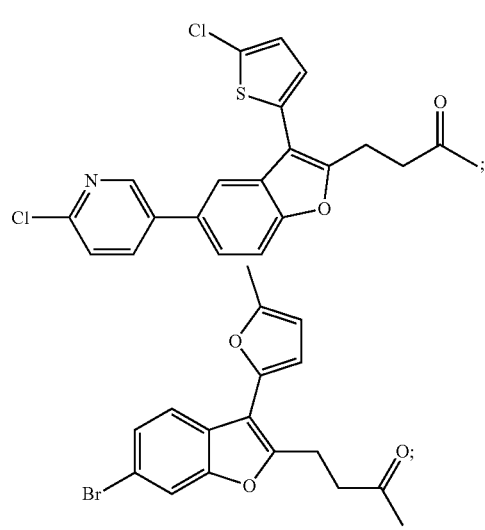
104
-continued
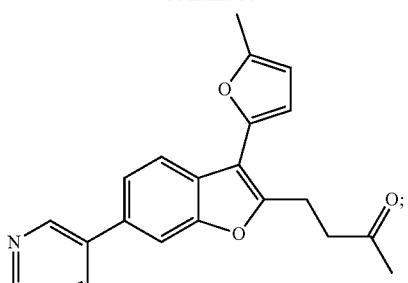
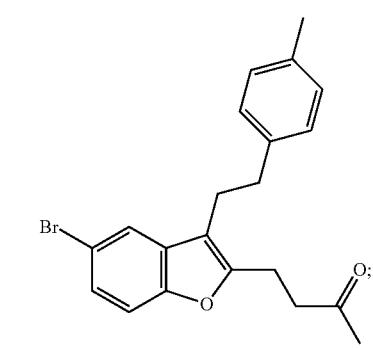
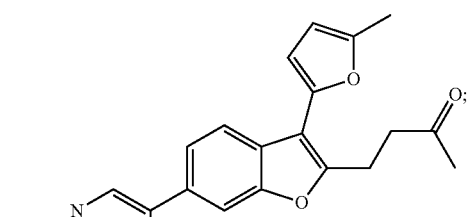
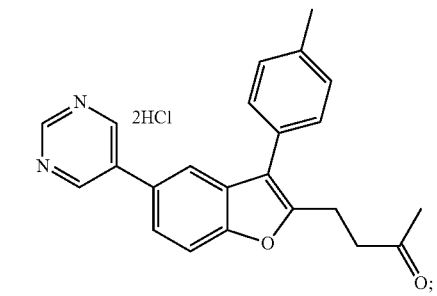
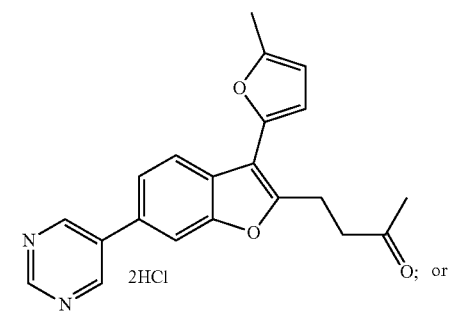

-continued

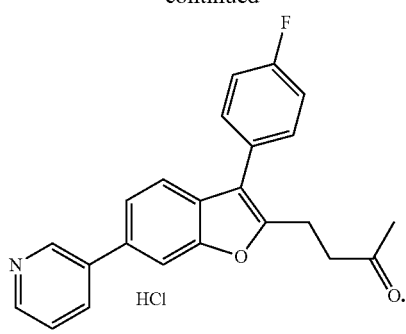

3. The compound from claim 2 wherein said compound has the following structure:

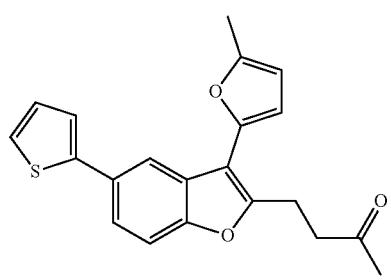

4. The compound from claim 2, wherein said compound has the following structure:

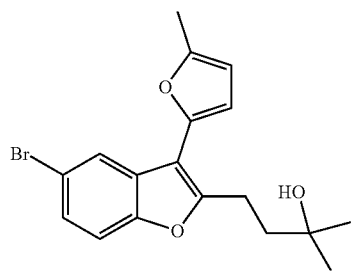

5. The compound from claim 2, wherein said compound has the following structure:

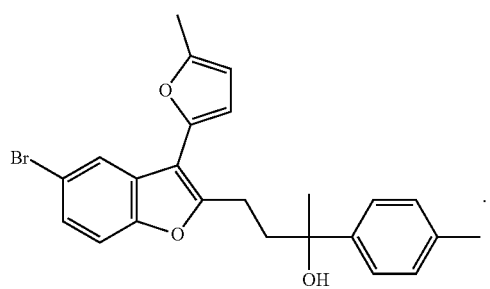 [SMILES: Cc1ccc(C(C)(O)CCc2oc3ccc(Br)cc3c2-c2ccc(C)o2)cc1]

6. The compound from claim 2, wherein said compound has the following structure:

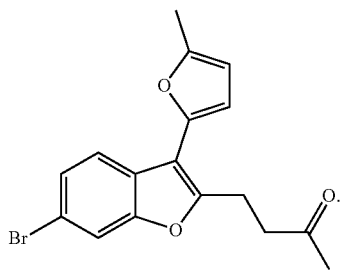 [SMILES: CC(=O)CCc1oc2cc(Br)ccc2c1-c1ccc(C)o1]

7. The compound from claim 2, wherein said compound has the following structure:

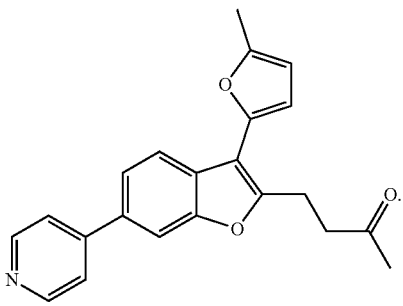 [SMILES: CC(=O)CCc1oc2cc(-c3ccncc3)ccc2c1-c1ccc(C)o1]

8. The compound from claim 2, wherein said compound has the following structure:

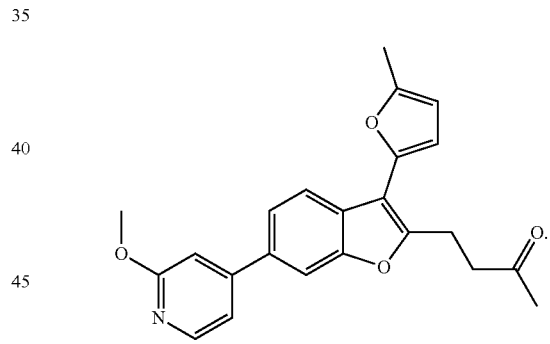

9. The compound from claim 2, wherein said compound has the following structure:

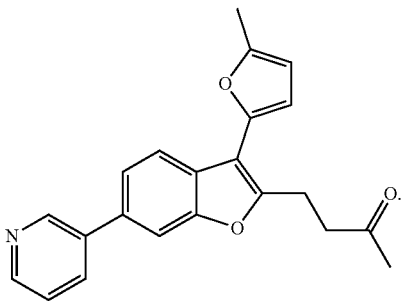 [SMILES: CC(=O)CCc1oc2cc(-c3cccnc3)ccc2c1-c1ccc(C)o1]

\* \* \* \* \*

SEQUENCE LISTING

<160> NUMBER OF SEQ ID NOS: 1

<210> SEQ ID NO 1
<211> LENGTH: 441
<212> TYPE: PRT
<213> ORGANISM: homo sapiens

<400> SEQUENCE: 1

Met Ala Glu Pro Arg Gln Glu Phe Glu Val Met Glu Asp His Ala Gly
1               5                   10                  15

Thr Tyr Gly Leu Gly Asp Arg Lys Asp Gln Gly Gly Tyr Thr Met His
            20                  25                  30

```
Gln Asp Gln Glu Gly Asp Thr Asp Ala Gly Leu Lys Glu Ser Pro Leu
     35                  40                  45

Gln Thr Pro Thr Glu Asp Gly Ser Glu Glu Pro Gly Ser Glu Thr Ser
 50                  55                  60

Asp Ala Lys Ser Thr Pro Thr Ala Glu Asp Val Thr Ala Pro Leu Val
 65                  70                  75                  80

Asp Glu Gly Ala Pro Gly Lys Gln Ala Ala Gln Pro His Thr Glu
                 85                  90                  95

Ile Pro Glu Gly Thr Thr Ala Glu Glu Ala Gly Ile Gly Asp Thr Pro
                100                 105                 110

Ser Leu Glu Asp Glu Ala Ala Gly His Val Thr Gln Ala Arg Met Val
            115                 120                 125

Ser Lys Ser Lys Asp Gly Thr Gly Ser Asp Asp Lys Lys Ala Lys Gly
        130                 135                 140

Ala Asp Gly Lys Thr Lys Ile Ala Thr Pro Arg Gly Ala Ala Pro Pro
145                 150                 155                 160

Gly Gln Lys Gly Gln Ala Asn Ala Thr Arg Ile Pro Ala Lys Thr Pro
                165                 170                 175

Pro Ala Pro Lys Thr Pro Pro Ser Ser Gly Glu Pro Pro Lys Ser Gly
            180                 185                 190

Asp Arg Ser Gly Tyr Ser Ser Pro Gly Ser Pro Gly Thr Pro Gly Ser
        195                 200                 205

Arg Ser Arg Thr Pro Ser Leu Pro Thr Pro Pro Thr Arg Glu Pro Lys
    210                 215                 220

Lys Val Ala Val Val Arg Thr Pro Pro Lys Ser Pro Ser Ser Ala Lys
225                 230                 235                 240

Ser Arg Leu Gln Thr Ala Pro Val Pro Met Pro Asp Leu Lys Asn Val
                245                 250                 255

Lys Ser Lys Ile Gly Ser Thr Glu Asn Leu Lys His Gln Pro Gly Gly
            260                 265                 270

Gly Lys Val Gln Ile Ile Asn Lys Lys Leu Asp Leu Ser Asn Val Gln
        275                 280                 285

Ser Lys Cys Gly Ser Lys Asp Asn Ile Lys His Val Pro Gly Gly Gly
    290                 295                 300

Ser Val Gln Ile Val Tyr Lys Pro Val Asp Leu Ser Lys Val Thr Ser
305                 310                 315                 320

Lys Cys Gly Ser Leu Gly Asn Ile His His Lys Pro Gly Gly Gly Gln
                325                 330                 335

Val Glu Val Lys Ser Glu Lys Leu Asp Phe Lys Asp Arg Val Gln Ser
            340                 345                 350

Lys Ile Gly Ser Leu Asp Asn Ile Thr His Val Pro Gly Gly Gly Asn
        355                 360                 365

Lys Lys Ile Glu Thr His Lys Leu Thr Phe Arg Glu Asn Ala Lys Ala
    370                 375                 380

Lys Thr Asp His Gly Ala Glu Ile Val Tyr Lys Ser Pro Val Val Ser
385                 390                 395                 400

Gly Asp Thr Ser Pro Arg His Leu Ser Asn Val Ser Ser Thr Gly Ser
                405                 410                 415

Ile Asp Met Val Asp Ser Pro Gln Leu Ala Thr Leu Ala Asp Glu Val
            420                 425                 430

Ser Ala Ser Leu Ala Lys Gln Gly Leu
        435                 440
```